(12) United States Patent
Lewis et al.

(10) Patent No.: US 8,187,340 B2
(45) Date of Patent: May 29, 2012

(54) COLORING AGENTS AND METHODS OF USE THEREOF

(75) Inventors: Jana Lewis, Medford, MA (US); Lorna Nagamoottoo-Casse, Boston, MA (US); David Puerta, Rockland, MA (US)

(73) Assignee: Living Proof, Inc., Cambridge, MA (US)

( * ) Notice: Subject to any disclaimer, the term of this patent is extended or adjusted under 35 U.S.C. 154(b) by 0 days.

(21) Appl. No.: 12/975,007

(22) Filed: Dec. 21, 2010

(65) Prior Publication Data

US 2011/0154583 A1 Jun. 30, 2011

Related U.S. Application Data

(60) Provisional application No. 61/288,668, filed on Dec. 21, 2009, provisional application No. 61/288,676, filed on Dec. 21, 2009, provisional application No. 61/415,251, filed on Nov. 18, 2010.

(51) Int. Cl.
*A61Q 5/10* (2006.01)

(52) U.S. Cl. ............. 8/405; 8/408; 8/409; 8/410; 8/415; 8/423

(58) Field of Classification Search ............... 8/405, 408, 8/409, 410, 415, 423
See application file for complete search history.

(56) References Cited

U.S. PATENT DOCUMENTS

| | | |
|---|---|---|
| 2,750,326 A | 6/1956 | Eckardt et al. |
| 3,632,582 A | 1/1972 | Bil |
| 3,665,036 A | 5/1972 | Kalopissis et al. |
| 3,867,456 A | 2/1975 | Kalopissis et al. |
| 3,904,690 A | 9/1975 | Kalopissis et al. |
| 3,944,612 A | 3/1976 | Bil |
| 4,797,129 A | 1/1989 | Junino et al. |
| 4,845,293 A | 7/1989 | Junino et al. |
| 5,891,200 A | 4/1999 | Lim et al. |
| 6,281,339 B1 | 8/2001 | Lehmann et al. |
| 6,447,554 B1 | 9/2002 | Brock et al. |
| 7,198,651 B2 | 4/2007 | Pratt et al. |
| 7,338,536 B2 * | 3/2008 | Sabelle et al. ............... 8/405 |
| 2006/0112502 A1 | 6/2006 | Cotteret et al. |

FOREIGN PATENT DOCUMENTS

| | | |
|---|---|---|
| EP | 2085434 | 8/2009 |
| FR | 2870727 | 12/2002 |
| GB | 1150445 | 4/1969 |
| GB | 1159557 | 7/1969 |
| GB | 1164824 | 9/1969 |
| GB | 1164825 | 9/1969 |
| JP | 7-35484 | 4/1995 |
| NL | 6610759 | 1/1967 |
| WO | WO2006/136516 | 12/2006 |
| WO | WO2009/037215 | 3/2009 |
| WO | WO2011/084803 | 7/2011 |

OTHER PUBLICATIONS

STIC Search Report dated May 10, 2011.*
International Search Report for PCT/US2010/061578 dated Sep. 30, 2011.

* cited by examiner

*Primary Examiner* — Eisa Elhilo

(74) *Attorney, Agent, or Firm* — McCarter & English LLP

(57) ABSTRACT

Dyes, compositions comprising dyes and methods for using the same are provided.

39 Claims, 2 Drawing Sheets

COLORING AGENTS AND METHODS OF USE THEREOF

RELATED APPLICATIONS

This application claims priority to U.S. Provisional Patent Application No. 61/288,668, filed on Dec. 21, 2009, 61/288,676, filed on Dec. 21, 2009 and U.S. Provisional Patent Application No. 61/415,251, filed on Nov. 18, 2010. The entire contents of the foregoing applications are hereby incorporated by reference.

BACKGROUND

According to the *International Cosmetic Ingredient Dictionary and Handbook*, Tenth Ed., 2004 (herein incorporated by reference in its entirety) hair colorants (e.g., materials which impart color to hair) are classified as temporary, semi-permanent, permanent or progressive.

Temporary hair colorants include color rinses, which provide color that lasts until the first shampooing. Ingredients which impart temporary color may have a fairly high molecular weight and are unable to penetrate the hair shaft. These materials are simply deposited onto the hair fiber and are removed by subsequent shampooing.

Direct dyes generally provide color through several shampooings. These materials are either low molecular weight pre-formed colored compounds that can penetrate the hair shaft to some extent or larger molecular weight colored compounds that interact with the surface of the hair fiber via non-covalent interactions.

Oxidative dyes are considered permanent hair coloring preparations as they provide color that is not substantially removed by shampooing. Oxidative coloration involves the deposition of an essentially colorless intermediate and of a coupling agent inside the hair fiber. In the presence of an oxidizing agent, usually hydrogen peroxide, these chemicals form a series of complex colored dyestuffs inside the hair fiber. Progressive hair coloring preparations are oxidative hair colors which develop color gradually by repeated applications.

While oxidative dyes may be preferred due to their long-lasting coloration, they have some disadvantages to direct coloring preparations. For example, direct dyes are more vibrant and provide a more "pure" color than do the oxidative dyes. It will be appreciated by those skilled in the art that the "pure" color of direct dyes is due to generally higher extinction coefficients and narrower peak widths at half height than oxidative dyes. Oxidative dyes can also participate in side reactions during the application process that can affect the final hair color and perform less well on damaged hair. Therefore, it would be desirable to develop non-oxidative dyes with the color and vibrancy of a direct dye and the long lasting color fastness of an oxidative dye that optionally performs better on damaged hair than on non-damaged hair.

SUMMARY OF THE INVENTION

The present invention is based, at least in part, on the discovery that certain functionalized, non-oxidative dyes exhibit an enhanced color fastness and vibrancy compared to other dyes (e.g., oxidative dyes and/or direct dyes). Therefore, it is an object of the present invention to provide such dyes and compositions thereof, as well as methods of using such dyes and kits comprising the same.

Accordingly, in one aspect, the present invention provides a functionalized dye comprising at least one chromophore and a color fastness moiety, wherein the chromophore is bound to the color fastness moiety by a linker, wherein said functionalized dye has an enhanced color fastness compared to a non-functionalized direct dye.

In some embodiments, the dye is a compound of formula Ia:

wherein
C is a chromophore;
L is a linker; and
F is a color fastness moiety, or a cosmetically acceptable salt thereof.

In some embodiments, color fastness moiety comprises at least one hydrogen bond donor and at least one hydrogen bond acceptor.

In some embodiments, the linker and the color fastness moiety comprise two or more hydrogen bond donors and at least one hydrogen bond acceptor.

In some embodiments, the hydrogen bond acceptor is a tertiary amine.

In some embodiments, the hydrogen bond donor is a secondary amine.

In some embodiments, C is of formula IIz:

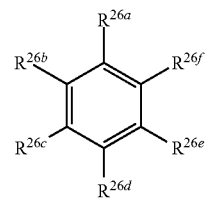

wherein
$R^{26a}$ is attached to linker L; and
$R^{26b}$, $R^{26c}$, $R^{26d}$, $R^{26e}$ and $R^{26f}$ are each independently hydrogen, hydroxy, amino, alkoxy, alkyl, halogen, $NO_2$, $CF_3$, $SO_3H$, CN, aminocarbonyl, carbonyl, alkoxycarbonyl or an aryldiazene moiety.

In some embodiments, $R^{26b}$ is $-NO_2$; $R^{26c}$, $R^{26e}$ and $R^{26f}$ are hydrogen; $R^{26d}$ is hydrogen or $NH_2$.

In some embodiments, L is of formula (III):

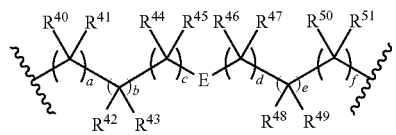

wherein
L covalently link the chromophore C via the left hand side of formula III to the color fastness moiety F via the right hand side of formula III;
a, b, c, d, e, and f are each independently an integer from 0-2, provided that at least one of a, b, c, d, e and f is not 0;
$R^{40}$, $R^{41}$, $R^{42}$, $R^{43}$, $R^{44}$, $R^{45}$, $R^{46}$, $R^{47}$, $R^{48}$, $R^{49}$, $R^{50}$ and $R^{51}$ are each independently absent or hydrogen;
E is $NR^{52}$ or $NR^{53}C=O$;
$R^{52}$ and $R^{53}$ are each independently hydrogen or alkyl.

In some embodiments, a, b, c and d are each 0, e and f are each 1; E is $NR^{52}$; and $R^{52}$ is hydrogen.

In some embodiments, the color fastness moiety is of formula (V):

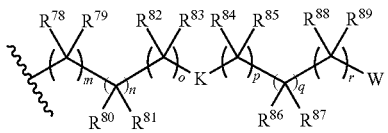

(V)

wherein m, n, o, p, q and r are each independently an integer from 0-2, provided that at least one of m, n, o, p, q and r is not 0;
$R^{78}$, $R^{79}$, $R^{80}$, $R^{81}$, $R^{82}$, $R^{83}$, $R^{84}$, $R^{85}$, $R^{87}$, $R^{88}$ and $R^{89}$ are each independently hydrogen or absent;
$R^{86}$ is absent, hydrogen or hydroxyl;
K is $NR^{90}$, $C(=O)NR^{92}$ or $OC=O$;
W is $NR^{95}R^{96}$, $CR^{97}R^{98}R^{99}$ or $OR^{100}$;
$R^{90}$ and $R^{92}$ are each independently hydrogen or alkyl;
$R^{95}$ is alkyl and $R^{96}$ is hydrogen or alkyl, or $R^{95}$ and $R^{96}$, together with the nitrogen to which they are attached are linked to form a 4-8-membered heterocyclic ring comprising 1-3 heteroatoms;
$R^{97}$, $R^{98}$ and $R^{99}$ are hydrogen, alkyl, alkoxy or heteroaryl; and
$R^{100}$ is hydrogen or alkyl, or a cosmetically acceptable salt thereof;
provided that when m, n, o and p are 0; q and r are 1, $R^{86}$, $R^{87}$, $R^{88}$ and $R^{89}$ are each hydrogen; W is $OR^{100}$, K is $NR^{90}$ and $R^{100}$ is hydrogen, then $R^{90}$ is not methyl.

In some embodiments, m, n and o are 0; p, q and r are each 1; $R^{84}$, $R^{85}$, $R^{86}$, $R^{87}$, $R^{88}$ and $R^{89}$ are each hydrogen; K is $NR^{90}$; $R^{90}$ is hydrogen; W is $NR^{95}NR^{96}$, and $R^{95}$ and $R^{96}$ are each alkyl.

In some embodiments, the dye is a compound of formula Xa:

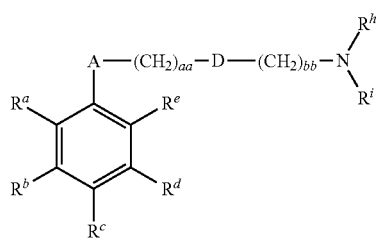

(Xa)

wherein $R^a$, $R^b$, $R^c$, $R^d$ and $R^e$ are each independently hydrogen, hydroxy, amino, alkoxy, alkyl, halogen, $NO_2$, $CF_3$, $SO_3H$, CN, aminocarbonyl, carbonyl, alkoxycarbonyl or an aryldiazene moiety;
aa and bb are each an integer from 1-5;
A is $NR^f$ or $NR^fCO$;
D is $O(CO)$, $NR^g$ or $CONR^g$;
$R^f$, $R^g$ and $R^h$ are each independently hydrogen or alkyl;
$R^i$ is alkyl; or $R^h$ and $R^i$ are linked together with the atom to which they are attached form a 4-8 membered heterocyclic ring with 1-3 heteroatoms; or a cosmetically acceptable salt thereof.

In some embodiments, $R^a$ is $-NO_2$; $R^b$, $R^d$ and $R^e$ are each hydrogen; $R^c$ is hydrogen or $NH_2$; A is $NR^f$; D is $NR^g$; $R^f$ and $R^g$ are each hydrogen; and $R^h$ and $R^i$ are each alkyl. In some embodiments, the alkyl is methyl, ethyl or hydroxyethyl.

In some embodiments, $R^a$ is $-NO_2$; $R^b$, $R^d$ and $R^e$ are each hydrogen; $R^c$ is hydrogen or $NH_2$; A is $NR^f$; D is $NR^g$; $R^f$ and $R^g$ are each hydrogen; and $R^h$ and $R^i$ are linked to form a 6-membered heterocyclic ring. In some embodiments, the ring is a piperidine or morpholine ring.

In some embodiments, the dye is a compound of formula (XIa):

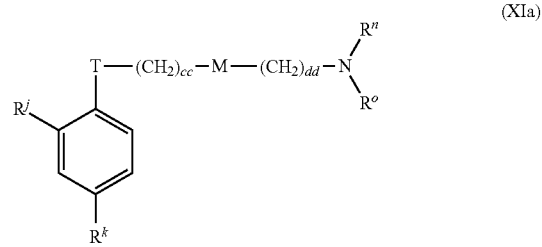

(XIa)

$R^j$ and $R^k$ are each independently hydrogen, hydroxy, amino, alkoxy, alkyl, halogen, $NO_2$, $CF_3$, $SO_3H$, CN, aminocarbonyl, carbonyl, alkoxycarbonyl or an aryldiazene moiety;
cc and dd are each an integer from 1-5;
T is $NR^l$ or $NR^lCO$;
M is $NR^m$ or $CONR^m$;
Q is $NR^nR^o$;
$R^l$, $R^m$ and $R^n$ are each independently hydrogen or alkyl;
$R^o$ is alkyl; or $R^n$ and $R^o$ are linked together with the atom to which they are attached form a 4-8 membered heterocyclic ring with 1-3 heteroatoms; and cosmetically acceptable salts thereof.

In some embodiments, T is $NR^l$; M is $NR^m$; $R^l$ and $R^m$ are each hydrogen; cc is 2 and dd is 3; $R^j$ is $NO_2$; $R^k$ is hydrogen or $NH_2$; $R^n$ and $R^o$ are each alkyl. In some embodiments, the alkyl is methyl, ethyl or hydroxyethyl.

In some embodiments, T is $NR^l$; M is $NR^m$; $R^l$ and $R^m$ are each hydrogen; cc is 2 and dd is 3; $R^j$ is $NO_2$; $R^k$ is hydrogen or $NH_2$; $R^n$ and $R^o$ are linked to form a 6-membered heterocyclic ring. In some embodiments, the ring is a piperidine or a morpholine ring.

In some embodiments, the dye is a compound of formula XII:

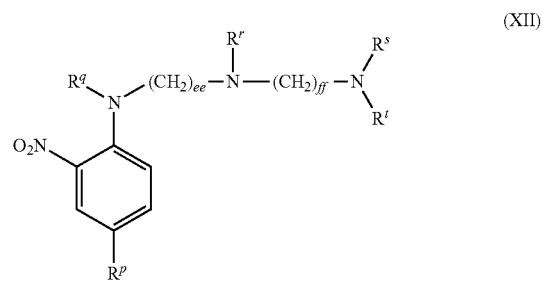

(XII)

wherein $R^p$ is hydrogen or amino;
$R^q$ and $R^r$ are each independently hydrogen or alkyl;
ee and ff are each independently an integer from 1-5; and
$R^s$ and $R^t$ are each alkyl or together with the atom to which they are attached form a 4-8 membered heterocyclic ring with 1 or 2 heteroatoms, and cosmetically acceptable salts thereof.

In some embodiments, $R^q$ and $R^r$ are each hydrogen; ee is 2 and ff is 3; and $R^s$ and $R^t$ are each alkyl. In some embodiments, the alkyl is methyl, ethyl or hydroxyethyl. In some embodiments, $R^p$ is hydrogen or $NH_2$ In some embodiments, $R^q$ and $R^r$ are each hydrogen; ee is 2 and ff is 3; and $R^s$ and $R^t$ are linked to form a 6-membered heterocyclic ring. In some embodiments, the ring is a piperidine or morpholine ring. In some embodiments, $R^p$ is hydrogen or $NH_2$.

In some embodiments, the dye is a compound of formula XIII:

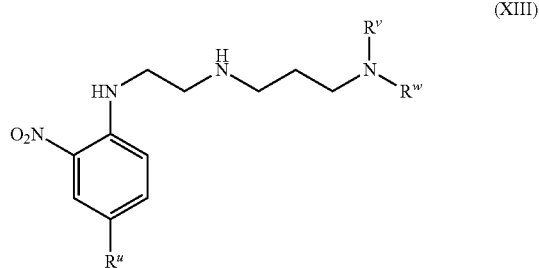

(XIII)

wherein $R^u$ is hydrogen or $NH_2$ and $R^v$ and $R^w$ are alkyl, and cosmetically acceptable salts thereof.

In some embodiments, $R^v$ and $R^w$ are each methyl, ethyl or hydroxyethyl.

In some embodiments, the dye is a compound selected from Table 2 or a cosmetically acceptable salt thereof.

In some aspects, the present invention provides a dye composition comprising at least one dye disclosed herein and a medium suitable for dyeing keratin fibers.

In some embodiments, the medium further includes one or more of surfactants, thickeners, direct dyes, fragrances, sequestering agents, UV-screening agents, waxes, silicones, preserving agents, couplers, primary intermediates, alkalizing agents, ceramides, oils, vitamins, provitamins, opacifiers, reducing agents, antioxidants, emulsifiers, chelating agents, color retardants, solvents and buffers.

In some aspects, the invention provides methods for coloring hair comprising applying to said hair a dye composition comprising at least one dye disclosed herein, or a cosmetically acceptable salt thereof.

In some embodiments, the coloring hair is highlighting hair or touching up roots.

In some aspects, the present invention provides a kit comprising a dye composition comprising at least one dye disclosed herein and instructions for use.

In some embodiments, the kit further comprises at least one or more direct dyes, a developer bottle, gloves or a conditioning rinse.

DETAILED DESCRIPTION OF THE INVENTION

Figure 1:
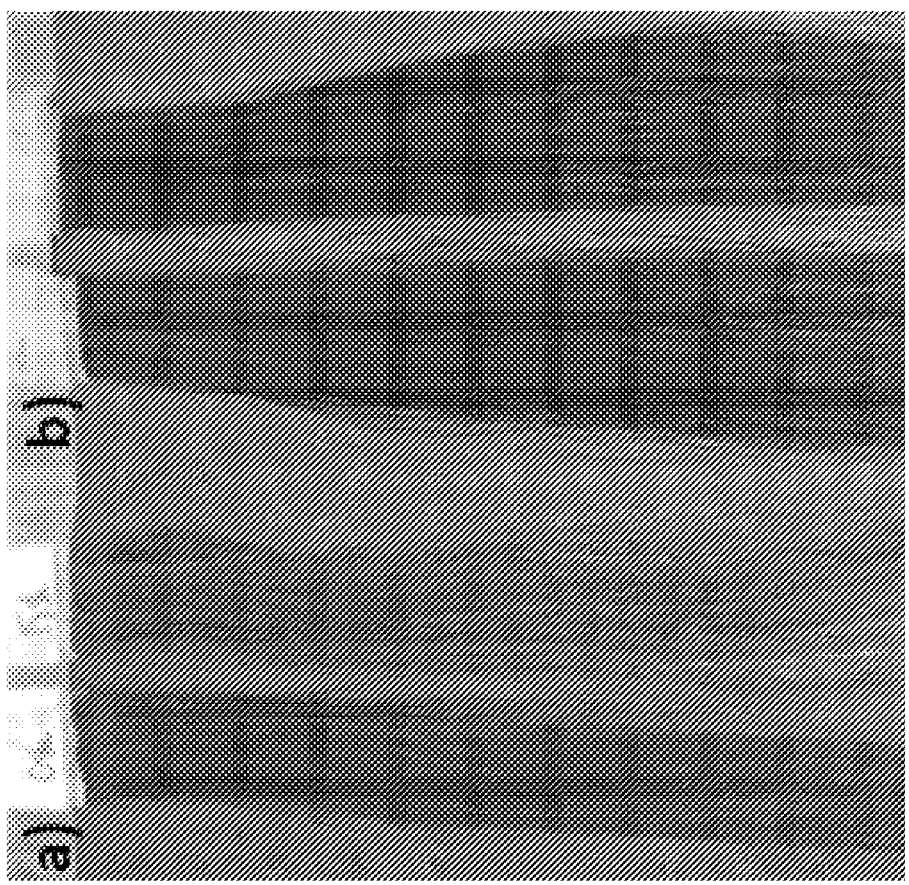
FIGS. 1a and 1b compare the color fastness of a commercially available red dye (FIG. 1a) with the color fastness of compound A (FIG. 1b) immediately after application to hair (1a and 1b; left tresses) and after 15 shampoo cycles (1a and 1b; right tresses).

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

I. Dyes

It should be noted that the terma "dye" and "compound" may be used interchangeably.

In some aspects, the present invention provides functionalized dyes. The language "functionalized dye" includes dyes having at least one chromophore that has been chemically modified. The language "non-functionalized dye" includes dyes that have at least one chromophore that has not been chemically modified. In some embodiments, the non-functionalized dye is a chromophore, C, as defined below.

In other aspects, the present invention provides damage selective dyes. The language "damage selective dye" includes dyes that perform better on damaged hair than normal hair (e.g., undamaged hair). The term "damaged hair" includes hair that is more porous than normal hair due to chemical exposure (e.g., bleaching or overdying hair, exposure to chemicals in swimming pools or minerals in groundwater), prolonged or repeated heat exposure (e.g., through the use of heat styling tools or excessive sun exposure), prolonged UV exposure, excessive perming and straightening of hair or a genetic predisposition to having more porous hair. In one embodiment, damaged hair includes hair with split ends. The language "normal hair" includes hair that is of normal porosity (e.g., undamaged hair) and may include unbleached or uncolored hair.

In some aspects, invention provides non-oxidative dyes. The language "non-oxidative dye" includes dyes that are pre-formed before application on the hair and do not require a coupling agent or an oxidizing agent to form the dye after deposition on the hair. In contrast, the language "oxidative dye" includes dyes that are formed by the application of an intermediate, a coupling agent and an oxidizing agent onto the hair such that the intermediate and coupling agent penetrate the hair and undergo a chemical reaction to form a colored dye within the hair.

In some embodiments, the dyes of the invention have a greater color fastness than a semi-permanent dye (e.g., a level 2 dye or a dye that lasts for about 5-8 shampoos). In some embodiments, the dyes of the invention have a greater color fastness than a permanent (e.g., a level 3 dye or a dye that last for about 9 or more shampoos). The language "greater color fastness" includes the ability of the dye to have an improved resistance to color change or color fading after application to hair when compared to a direct dye or an oxidative dye of substantially the same color.

In some embodiments, the dye is retained and imparts color on hair after application to the hair. The language "retained and imparts color" includes the ability of the dye to remain on the hair and provide the desired color with substantially no change in color or fading of color after a period of time compared to a direct dye or an oxidative dye of substantially the same color and after substantially the same period of time, as measured by the visual inspection assay described in Example 4. In some embodiments, the dye is retained and imparts color on hair after application to the hair at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% longer than a direct dye or an oxidative dye of substantially the same color.

In other embodiments, the dye has greater vibrancy after application to hair. The language "greater vibrancy" includes the ability of the dye to provide a brighter color after application to hair compared to an oxidative dye, as measured, for example, by the visual inspection assay described in Example 4 or by a colorimeter. In some embodiments, the dye provides vibrancy that is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% greater than an oxidative dye of substantially the same color.

In other embodiments, the dye maintains its vibrancy after application to hair. The language "maintains vibrancy" includes the ability of the dye to retain its brightness after a period of time compared to an oxidative dye of substantially the same color after substantially the same period of time, as measured by the visual inspection assay described in Example 4. In some embodiments, the dye maintains its vibrancy by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% longer than an oxidative dye of substantially the same color.

In some embodiments, the dyes of the invention are non-ionic (e.g., the dyes do not have a positive charge (e.g., non-cationic) or negative charge (e.g., non-anionic)). Examples of anionic and cationic dyes include, but are not limited to, those in Table 1.

In some embodiments, the dye is fluorescent.

In other embodiments, the dye is a non-natural dye (e.g., a dye obtained from a natural source, for example, a plant, animal or mineral). Examples of dyes obtained from natural sources include, for example, indigo, carminic acid, lawsone (e.g., henna), lycopene, madder, monascus derivatives, santalin, annatto, apigenin, canthaxanthin, capsanthin, capsorubin, carotenes, carthamin, crocin, crocetin, curcumin, lutein, luteolin, pratol, caramel, cocoa, chlorophyll and indigo.

In still other embodiments and without being bound by theory, the dye interacts with hair by non-covalent interactions after application to the hair. Examples of non-covalent interactions include, for example, hydrogen bonding, pi stacking, van der Waals interactions, hydrophobic interactions and dipole-dipole interactions.

In some embodiments, the dye is a functionalized oxidative dye precursor or intermediate that is capable of further reactive chemistry inside the hair fiber typical of oxidative dyes (e.g., functionalized para-phenylene diamine) such that the final reacted dye has longer lasting color than the non-functionalized dye.

In one embodiment, the dye is of formula Ia:

C-L-F                                                    (Ia)

wherein

C is a chromophore,

L is a linker and;

F is a color fastness moiety and cosmetically acceptable salts thereof.

In other embodiments, the dye is of formula Ib:

C-L-F-L*-C*                                              (Ib)

wherein

C and C* are each the same or a different chromophores;

L and L* are linkers; and

F is a color fastness moiety, and cosmetically acceptable salts thereof.

The term "chromophore" includes chemical moieties that are capable of providing color to the dyes of the invention. In some embodiments, the chromophore is a colored moiety prior to being covalently linked to L and/or L* and/or F. In other embodiments, the dye resulting from covalently linking L and/or L* and/or F to C or C* when C or C* is a colored moiety provides a molecule with the same or a different color than C or C*. In some embodiments, when C or C* are non-colored molecules, the covalent bonding of C or C* to L and/or L* and/or F result in a colored molecule.

In some embodiments, the chromophore (e.g., C or C*) is selected from the group consisting of an anthraquinone chromophore, an arylmethane chromophore, a diarylmethane chromophore, a diphenyl methane chromophore, a triarylmethane chromophore, an azo chromophore, a cyanine chromophore, a diazonium chromophore, a nitro chromophore, a nitroso chromophore, a phthalocyanine chromophore, a quinone-imine chromophore, an azin chromophore, an eurhodin chromophore, a safranin chromophore, an indamin chromophore, an indophenol chromophore, an oxazin chromophore, an oxazone chromophore, a thiazin chromophore, a thiazole chromophore, a xanthene chromophore, a fluorine chromophore, a pyronin chromophore, a fluorine chromophore, a rhodamine chromophore, a substituted benzene or a derivative or a cosmetically acceptable salts thereof. Examples of the foregoing chromophores include, but are not limited to, those compounds found in Table 1.

In at least one embodiment, the present invention includes dyes wherein the "C" or "C*" substituent of formulae Ia and Ib is a known chromophore, e.g., including, but not limited to, a chromophore listed in Table 1, below. In this embodiment, the dyes of the invention include an "L" or "L*"substituent and/or and "F" substituent, which are defined above, in addition to the chromophores. In another embodiment, the dye of the invention is not a compound of Table 1.

In other embodiments, the chromophore is a compound of formula IIa:

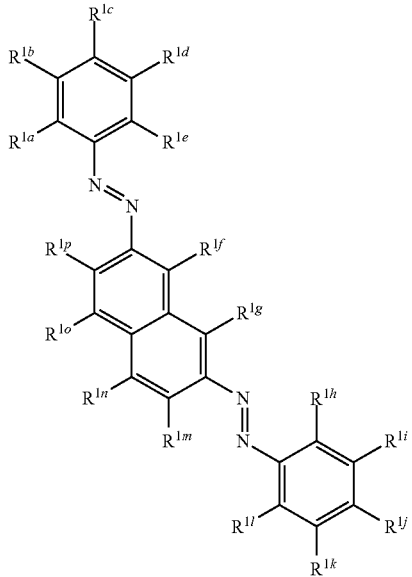

(IIa)

wherein
$R^{1a}$, $R^{1b}$, $R^{1c}$, $R^{1d}$, $R^{1e}$, $R^{1f}$, $R^{1g}$, $R^{1h}$, $R^{1i}$, $R^{1j}$, $R^{1k}$, $R^{1l}$, $R^{1m}$, $R^{1n}$, $R^{1o}$ and $R^{1p}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIb:

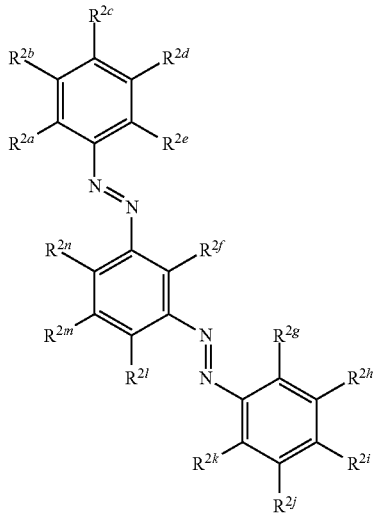

(IIb)

wherein
$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, $R^{2l}$, $R^{2m}$ and $R^{2n}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to the linker L or L*, and cosmetically acceptable salts thereof.

In other embodiments, the chromophore is a compound of formula IIc:

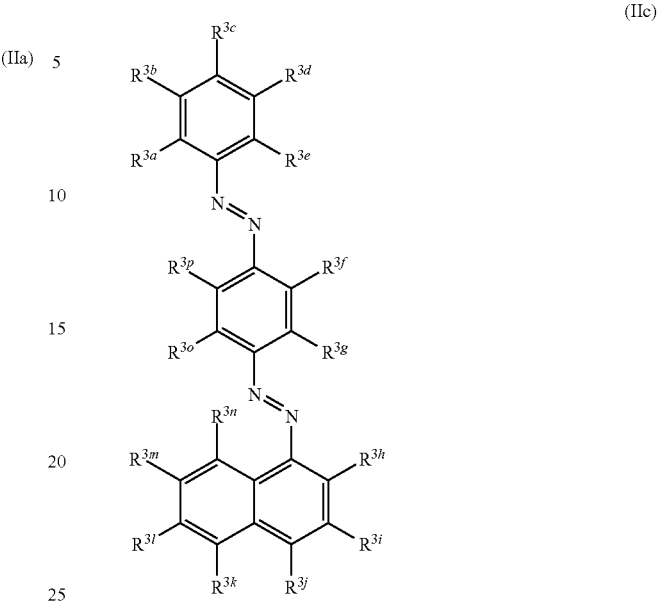

(IIc)

wherein
$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3l}$, $R^{3m}$, $R^{3n}$, $R^{3o}$ and $R^{3p}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IId:

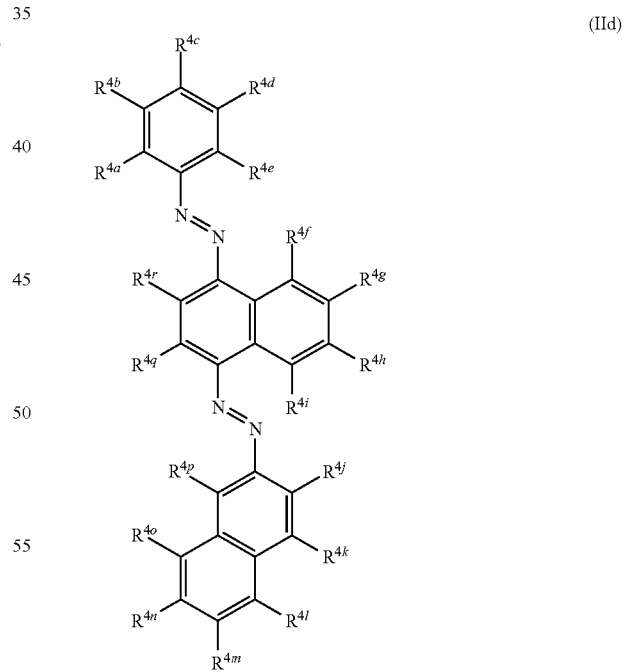

(IId)

wherein
$R^{4a}$, $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, $R^{4l}$, $R^{4m}$, $R^{4n}$, $R^{4o}$, $R^{4p}$, $R^{4q}$ and $R^{4r}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIe:

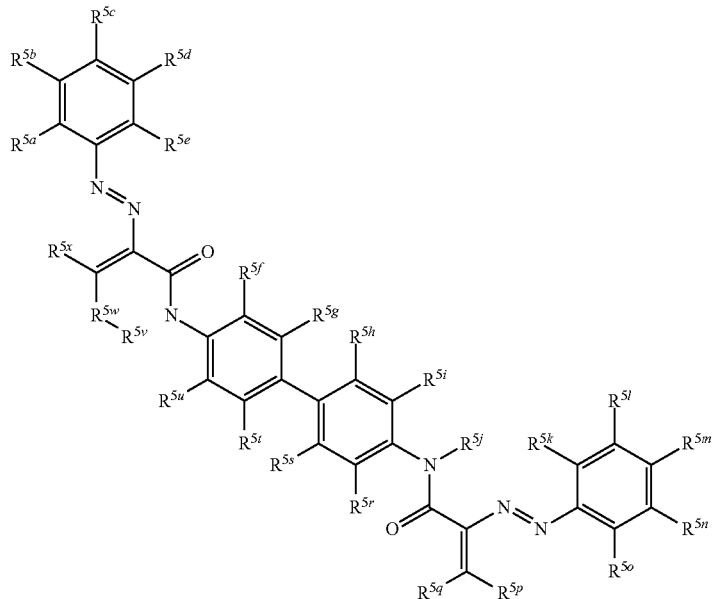

(IIe)

wherein
$R^{5a}, R^{5b}, R^{5c}, R^{5d}, R^{5e}, R^{5f}, R^{5g}, R^{5h}, R^{5i}, R^{5k}, R^{5l}, R^{5m}, R^{5n}, R^{5o}, R^{5p}, R^{5q}, R^{5r}, R^{5s}, R^{5t}, R^{5u}, R^{5w}$ and $R^{5x}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*; and $R^{5j}$ and $R^{5v}$ are each independently hydrogen, hydroxyl, alkoxy, alkyl, alkenyl, alkynyl, aryl, carbonyl, carboxy, acyl or are attached to the linker L or L*, and cosmetically acceptable salts thereof.

In other embodiments, the chromophore is a compound of formula IIf:

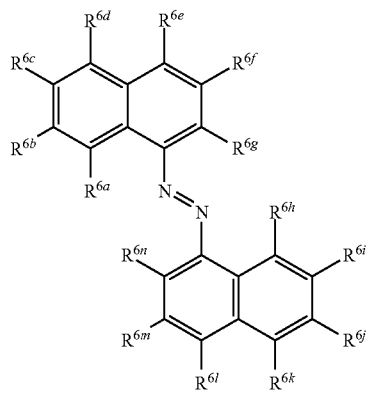

(IIf)

wherein
$R^{6a}, R^{6b}, R^{6c}, R^{6d}, R^{6e}, R^{6f}, R^{6g}, R^{6h}, R^{6i}, R^{6j}, R^{6k}, R^{6l}, R^{6m}$ and $R^{6n}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIg:

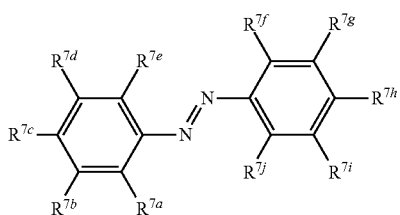

(IIg)

wherein
$R^{7a}, R^{7b}, R^{7c}, R^{7d}, R^{7e}, R^{7f}, R^{7g}, R^{7h}, R^{7i}$ and $R^{7j}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIh:

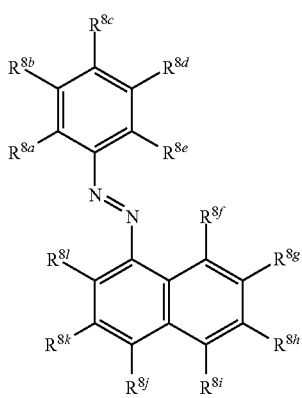

(IIh)

wherein $R^{8a}$, $R^{8b}$, $R^{8c}$, $R^{8d}$, $R^{8e}$, $R^{8f}$, $R^{8g}$, $R^{8h}$, $R^{8i}$, $R^{8j}$, $R^{8k}$ and $R^{8l}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*, and cosmetically acceptable salts thereof.

In other embodiments, the chromophore is a compound of formula IIi:

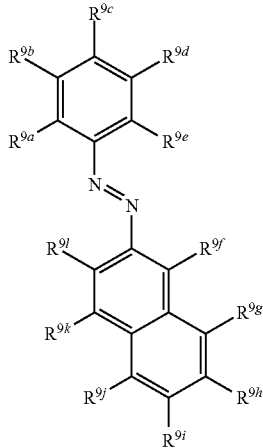

(IIi)

wherein $R^{9a}$, $R^{9b}$, $R^{9c}$, $R^{9d}$, $R^{9e}$, $R^{9f}$, $R^{9g}$, $R^{9h}$, $R^{9i}$, $R^{9j}$, $R^{9k}$ and $R^{9l}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*, and cosmetically acceptable salts thereof.

In other embodiments, the chromophore is a compound of formula IIj:

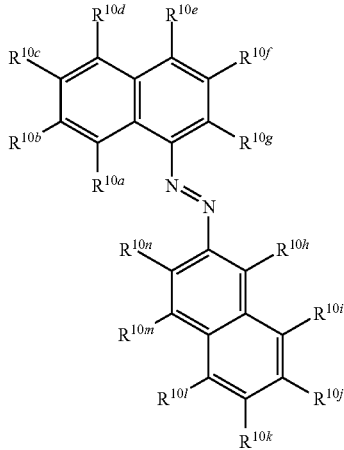

(IIj)

wherein $R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{10k}$, $R^{10l}$, $R^{10m}$ and $R^{10n}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*, and cosmetically acceptable salts thereof.

In other embodiments, the chromophore is a compound of formula IIk:

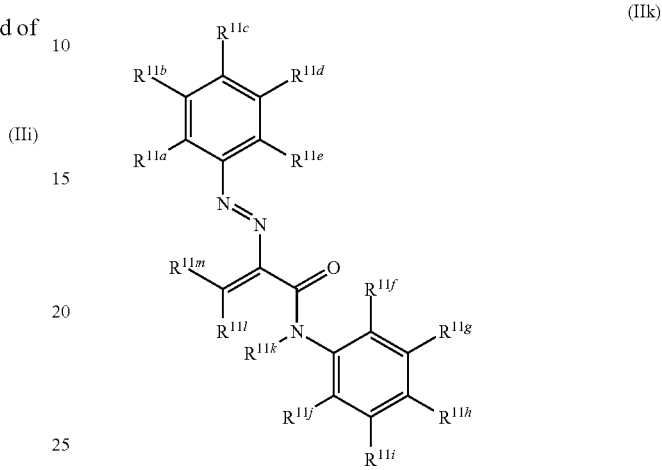

(IIk)

wherein $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11l}$ and $R^{11m}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*; and $R^{11k}$ is hydrogen, hydroxyl, alkoxy, alkyl, alkenyl, alkynyl, aryl, carbonyl, carboxy, acyl or is attached to linker L or L*, and cosmetically acceptable salts thereof.

In other embodiments, the chromophore is a compound of formula IIl:

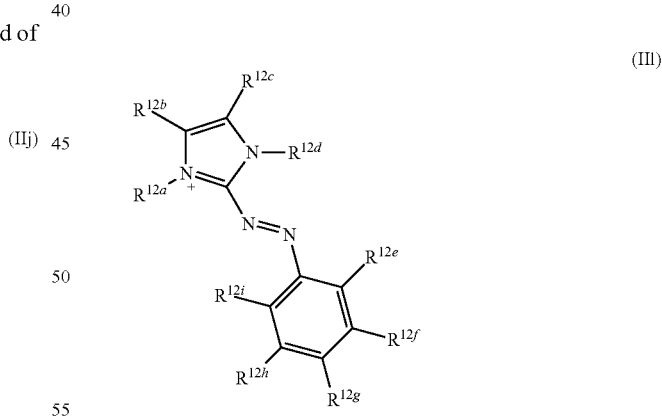

(IIl)

wherein $R^{12b}$, $R^{12c}$, $R^{12e}$, $R^{12f}$, $R^{12g}$, $R^{12h}$ and $R^{12i}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*; and $R^{12a}$ and $R^{12d}$ are each independently hydrogen, hydroxyl, alkoxy, alkyl, alkenyl, alkynyl, aryl, carbonyl, carboxy, acyl or are attached to linker L or L*, and cosmetically acceptable salts thereof.

In other embodiments, the chromophore is a compound of formula IIm:

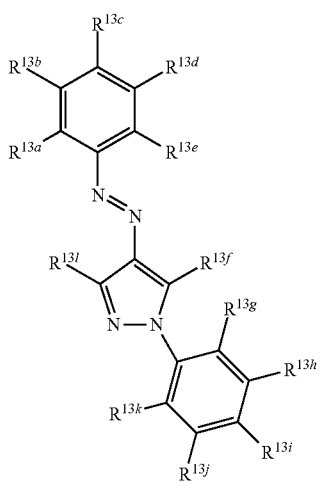

(IIm)

wherein $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, $R^{13k}$ and $R^{13l}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIn:

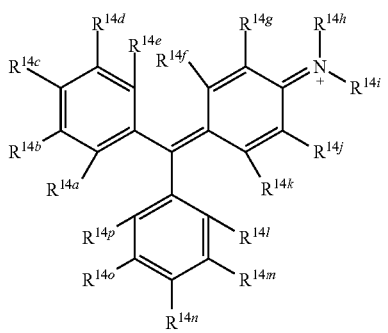

(IIn)

wherein $R^{14a}$, $R^{14b}$, $R^{14c}$, $R^{14d}$, $R^{14e}$, $R^{14f}$, $R^{14g}$, $R^{14j}$, $R^{14k}$, $R^{14l}$, $R^{14m}$, $R^{14n}$, $R^{14o}$ and $R^{14p}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*; and $R^{14h}$ and $R^{14i}$ are each independently hydrogen, hydroxyl, alkoxy, alkyl, alkenyl, alkynyl, aryl, carbonyl, carboxy, acyl or are attached to linker L or L*, and cosmetically acceptable salts thereof.

In other embodiments, the chromophore is a compound of formula IIo:

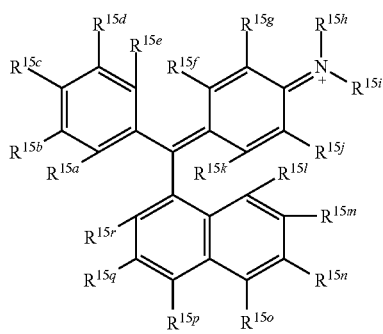

(IIo)

wherein $R^{15a}$, $R^{15b}$, $R^{15c}$, $R^{15d}$, $R^{15e}$, $R^{15f}$, $R^{15g}$, $R^{15j}$, $R^{15k}$, $R^{15l}$, $R^{15m}$, $R^{15n}$, $R^{15o}$, $R^{15p}$, $R^{15q}$ and $R^{15r}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*; and $R^{15h}$ and $R^{15i}$ are each independently hydrogen, hydroxyl, alkoxy, alkyl, alkenyl, alkynyl, aryl, carbonyl, carboxy, acyl or are attached to linker L or L*, and cosmetically acceptable salts thereof.

In other embodiments, the chromophore is a compound of formula IIp:

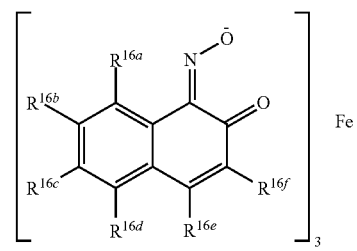

(IIp)

wherein $R^{16a}$, $R^{16b}$, $R^{16c}$, $R^{16d}$, $R^{16e}$ and $R^{16f}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*, and cosmetically acceptable salts thereof.

In other embodiments, the chromophore is a compound of formula IIq:

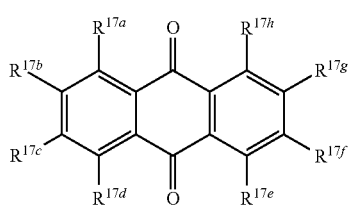

(IIq)

wherein $R^{17a}$, $R^{17b}$, $R^{17c}$, $R^{17d}$, $R^{17e}$, $R^{17f}$, $R^{17g}$ and $R^{17h}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to the linker L or L*, and cosmetically acceptable salts thereof.

In other embodiments, the chromophore is a compound of formula IIr:

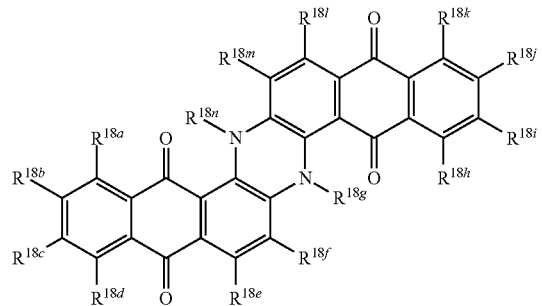

(IIr)

wherein $R^{18a}$, $R^{18b}$, $R^{18c}$, $R^{18d}$, $R^{18e}$, $R^{18h}$, $R^{18i}$, $R^{18j}$, $R^{18k}$, $R^{18l}$ and $R^{18m}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*; and $R^{18g}$ and $R^{18n}$ are each independently hydrogen, hydroxyl, alkoxy, alkyl, alkenyl, alkynyl, aryl, carbonyl, carboxy, acyl or are attached linker L or L*, and cosmetically acceptable salts thereof.

In other embodiments, the chromophore is a compound of formula IIs:

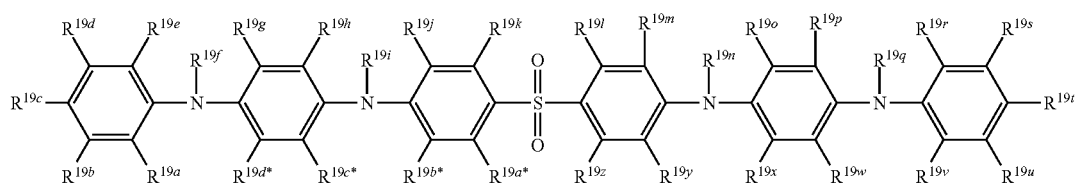

(IIs)

wherein $R^{19a}$, $R^{19b}$, $R^{19c}$, $R^{19d}$, $R^{19e}$, $R^{19g}$, $R^{19h}$, $R^{19j}$, $R^{19k}$, $R^{19l}$, $R^{19m}$, $R^{19o}$, $R^{19p}$, $R^{19r}$, $R^{19s}$, $R^{19t}$, $R^{19u}$, $R^{19v}$, $R^{19w}$, $R^{19x}$, $R^{19y}$, $R^{19z}$, $R^{19a*}$, $R^{19b*}$, $R^{19c*}$ and $R^{19d*}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*; and $R^{19f}$, $R^{19i}$, $R^{19n}$ and $R^{19q}$ are each independently hydrogen, hydroxyl, alkoxy, alkyl, alkenyl, alkynyl, aryl, carbonyl, carboxy, acyl or are attached to linker L or L*, and cosmetically acceptable salts thereof.

In other embodiments, the chromophore is a compound of formula IIt:

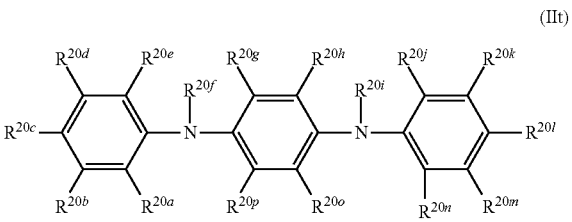

(IIt)

wherein $R^{20a}$, $R^{20b}$, $R^{20c}$, $R^{20d}$, $R^{20e}$, $R^{20g}$, $R^{20h}$, $R^{20j}$, $R^{20k}$, $R^{20l}$, $R^{20m}$, $R^{20n}$, $R^{20o}$ and $R^{20p}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*; and $R^{20f}$ and $R^{20i}$ are each independently hydrogen, hydroxyl, alkoxy, alkyl, alkenyl, alkynyl, aryl, carbonyl, carboxy, acyl or are attached to linker L or L*, and cosmetically acceptable salts thereof.

In other embodiments, the chromophore is a compound of formula IIu:

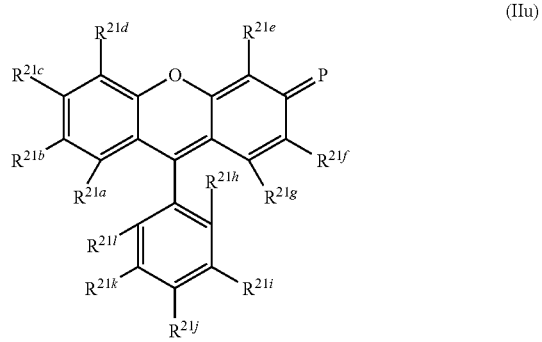

(IIu)

wherein $R^{21a}$, $R^{21b}$, $R^{21c}$, $R^{21d}$, $R^{21e}$, $R^{21f}$, $R^{21g}$, $R^{21h}$, $R^{21i}$, $R^{21j}$, $R^{21k}$ and $R^{21l}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —NO$_2$, —CN, a heterocyclic moiety or thioether or are attached to linker L or L*;

P is O or NR$^{21m}$; and $R^{21m}$ is hydrogen, hydroxyl, alkoxy, alkyl, alkenyl, alkynyl, aryl, carbonyl, carboxy, acyl or is attached to linker L or L*, and cosmetically acceptable salts thereof.

In other embodiments, the chromophore is a compound of formula IIv:

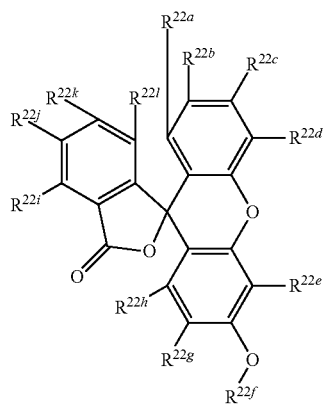

(IIv)

wherein $R^{22a}$, $R^{22b}$, $R^{22c}$, $R^{22d}$, $R^{22e}$, $R^{22g}$, $R^{22h}$, $R^{22i}$, $R^{22j}$, $R^{22k}$ and $R^{22l}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*; and $R^{22f}$ is hydrogen, alkyl, alkenyl, alkynyl, aryl, carbonyl, acyl or a heterocyclic moiety or is attached to L or L*, and cosmetically acceptable salts thereof.

In other embodiments, the chromophore is a compound of formula IIw:

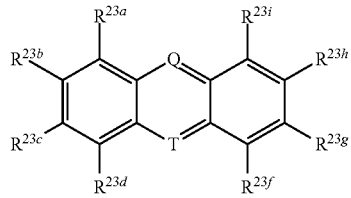

(IIw)

wherein $R^{23a}$, $R^{23b}$, $R^{23c}$, $R^{23d}$, $R^{23f}$, $R^{23g}$, $R^{23h}$ and $R^{23i}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*;

Q is S, O or N;

T is $N^+R^{23e}$ or N when $R^{23e}$ is absent; and $R^{23e}$ is absent, hydrogen, hydroxyl, alkoxy, alkyl, alkenyl, alkynyl, aryl, carbonyl, carboxy, acyl or is attached to linker L or L*, and cosmetically acceptable salts thereof.

In other embodiments, the chromophore is a compound of formula IIx:

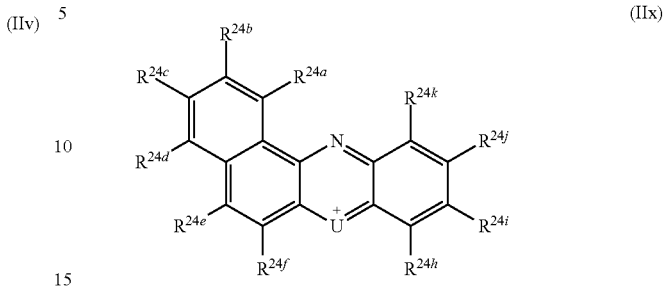

(IIx)

wherein $R^{24a}$, $R^{24b}$, $R^{24c}$, $R^{24d}$, $R^{24e}$, $R^{24f}$, $R^{24h}$, $R^{24i}$, $R^{24j}$ and $R^{24k}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to linker L or L*;

U is $N^+R^{24g}$ or O when $R^{24g}$ is absent; and $R^{24g}$ is absent, hydrogen, hydroxy, alkoxy, alkyl, alkenyl, alkynyl, aryl, carbonyl, carboxy, acyl or is attached to linker L or L*, and cosmetically acceptable salts thereof.

In other embodiments, the chromophore is a compound of formula IIy:

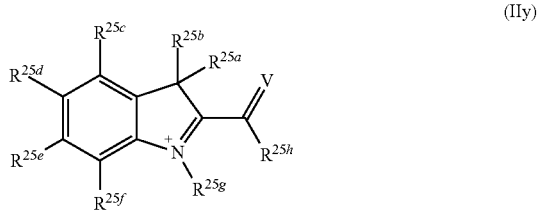

(IIy)

wherein $R^{25a}$, $R^{25b}$, $R^{25c}$, $R^{25d}$, $R^{25e}$, $R^{25f}$, $R^{25h}$, $R^{25i}$ and $R^{25j}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether or are attached to the linker L or L*;

V is $CR^{25i}R^{25j}$ or $NR^{25k}$; and $R^{25g}$ and $R^{25k}$ are each independently hydrogen, hydroxyl, alkoxy, alkyl, alkenyl, alkynyl, aryl, carbonyl, carboxy, acyl or attached to L or L*, and cosmetically acceptable salts thereof.

In other embodiments, the chromophore is a compound of formula IIz:

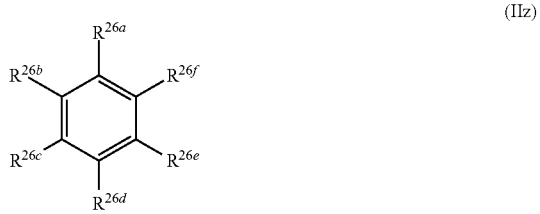

(IIz)

wherein $R^{26a}$, $R^{26b}$, $R^{26c}$, $R^{26d}$, $R^{26e}$ and $R^{26f}$ are each independently hydrogen, hydroxyl, alkyl, alkenyl, alkynyl, aryl, amino, alkylammonium, sulfonyl, sulfonic acid, carbonyl, carboxy, alkoxy, aryloxy, halogen, acyl, oximyl, hydrazinyl, —$NO_2$, —CN, —$CF_3$, $SO_3H$, aminocarbonyl, alkoxycarbonyl, a heterocyclic moiety, a diazene or thioether or are attached to the linker L or L*, and cosmetically acceptable salts thereof.

In some embodiments, the C is of formula IIz:

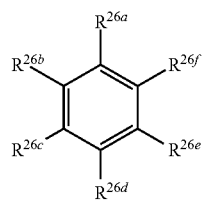

(IIz)

wherein $R^{26a}$ is attached to linker L; and $R^{26b}$, $R^{26c}$, $R^{26d}$, $R^{26e}$ and $R^{26f}$ are each independently hydrogen, hydroxy, amino, alkoxy, alkyl, $CF_3$, CN, halogen, $NO_2$, $SO_3H$, aminocarbonyl, carbonyl, alkoxycarbonyl or an aryldiazene moiety.

In some embodiments, $R^{26b}$ is —$NO_2$.

In some embodiments, $R^{26c}$, $R^{26e}$ and $R^{26f}$ are hydrogen.

In some embodiments, $R^{26d}$ is hydrogen or $NH_2$.

In yet other embodiments, the chromophore (e.g., C or C*) includes, but is not limited to, Acid Blue 1, Acid Blue 3, Acid Blue 5, Acid Blue 7, Acid Blue 9, Acid Blue 62, Acid Blue 104, Acid Brown 13, Acid Orange 3, Acid Orange 6, Acid Orange 7, Acid Orange 10, Acid Orange 11, Acid Orange 20, Acid Orange 24, Acid Red 14, Acid Red 33, Acid Red 35, Acid Red 41, Acid Red 50, Acid Red 51, Acid Red 52, Acid Red 87, Acid Red 92, Acid Red 94, Acid Red 95, Acid Red 98, Acid Red 184, Acid Green 1, Acid Green 9, Acid Green 22, Acid Green 25, Acid Green 50, Acid Yellow 1, Acid Yellow 9, Acid Yellow 73, Acid Violet 9, Acid violet 50, Basic Blue 3, Basic Blue 6, Basic Blue 7, Basic Blue 9, Basic Blue 26, Basic Blue 41, Basic Blue 47, Basic Blue 99, Basic Brown 4, Basic Brown 16, Basic Brown 17, Basic Green 1, Basic Green 4, Basic Orange 1, Basic Orange 2, Basic Orange 31, Basic Red 1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11, Basic Violet 14, Basic Violet 16, Basic Yellow 11, Basic Yellow 28, Basic Yellow 40, Basic Yellow 57, Basic Yellow 87, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 72, Disperse Brown 1, Disperse Orange 3, Disperse Red 1, Disperse Red 3, Disperse Red 11, Disperse Red 13, Disperse Red 14, Disperse Red 15, Disperse Red 17, Disperse Red 19, Disperse Violet 1, Disperse Violet 4, Disperse Violet 15, Disperse Violet 27, HC Blue 2, HC Blue 4, HC Blue 5, HC Blue 6, HC Blue 8, HC Blue 9, HC Blue 10, HC Blue 11, HC Blue 12, HC Blue 13, HC Blue 14, HC Blue 15, HC Brown 1, HC Brown 2, HC Green 1, HC Orange 1, HC Orange 2, HC Orange 3, HC Orange 5, HC Red 1, HC Red 3, HC Red 7, HC Red 8, HC Red 9, HC Red 10, HC Red 11, HC Red 13, HC Red 14, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, Disperse Red 3, Disperse Red 19, Acid Black 1, Acid Red 1, Acid Red 73, Solvent Red 23, Scarlet Red, Brilliant Black 1, Brown 1, CI 20040, CI 21100, CI 21108, CI 21230, CI 27755, CI 28440, Acid Black 52, Acid Red 18, Acid Red 27, Lithol Rubin B, Betanine, Lithol Red, CI 15800, CI 15880, Hansa Red B, CI 12085, Pigment Red 22, CI 15865:2, CI 16155, Acid Red 26, CI 14700, Solvent Orange 7, Acid Red 88, CI 11680, CI 11710, CI 11725, CI 11920, CI 12010, CI 12085, CI 12120, CI 12150, CI 12370, CI 12420, CI 12480, CI 12490, Acid Yellow 23, Acid Red 195, CI 12700, CI 14700, CI 14815, CI 15525, CI 15580, CI 15630, CI 15850, CI 15980, CI 15985, CI 16035, Acid Red 155, Acid Yellow 121, Acid Red 180, Acid Yellow 11, CI 12075, CI 12100, CI 42053, Acid Violet 43, CI 69825, Solvent Blue 63, CI 58000, CI 61565, Acid Blue 80, CI 69800, CI 10006, Rhodamine B, Japan Red 104, Japan Red 223, Acid Yellow 73, CI 45396, CI 45410, CI 45370, CI 51319 and a compound disclosed of Table 1, and/or derivatives and cosmetically acceptable salts thereof.

TABLE 1

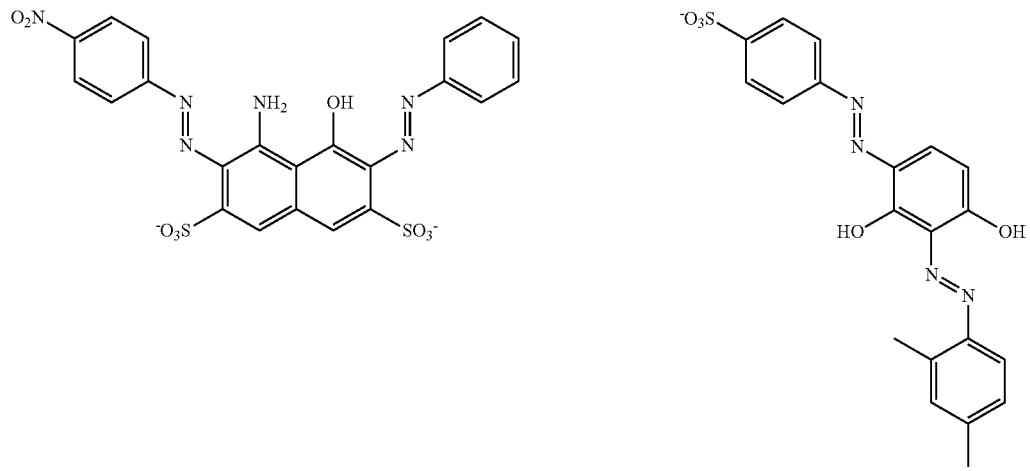

TABLE 1-continued
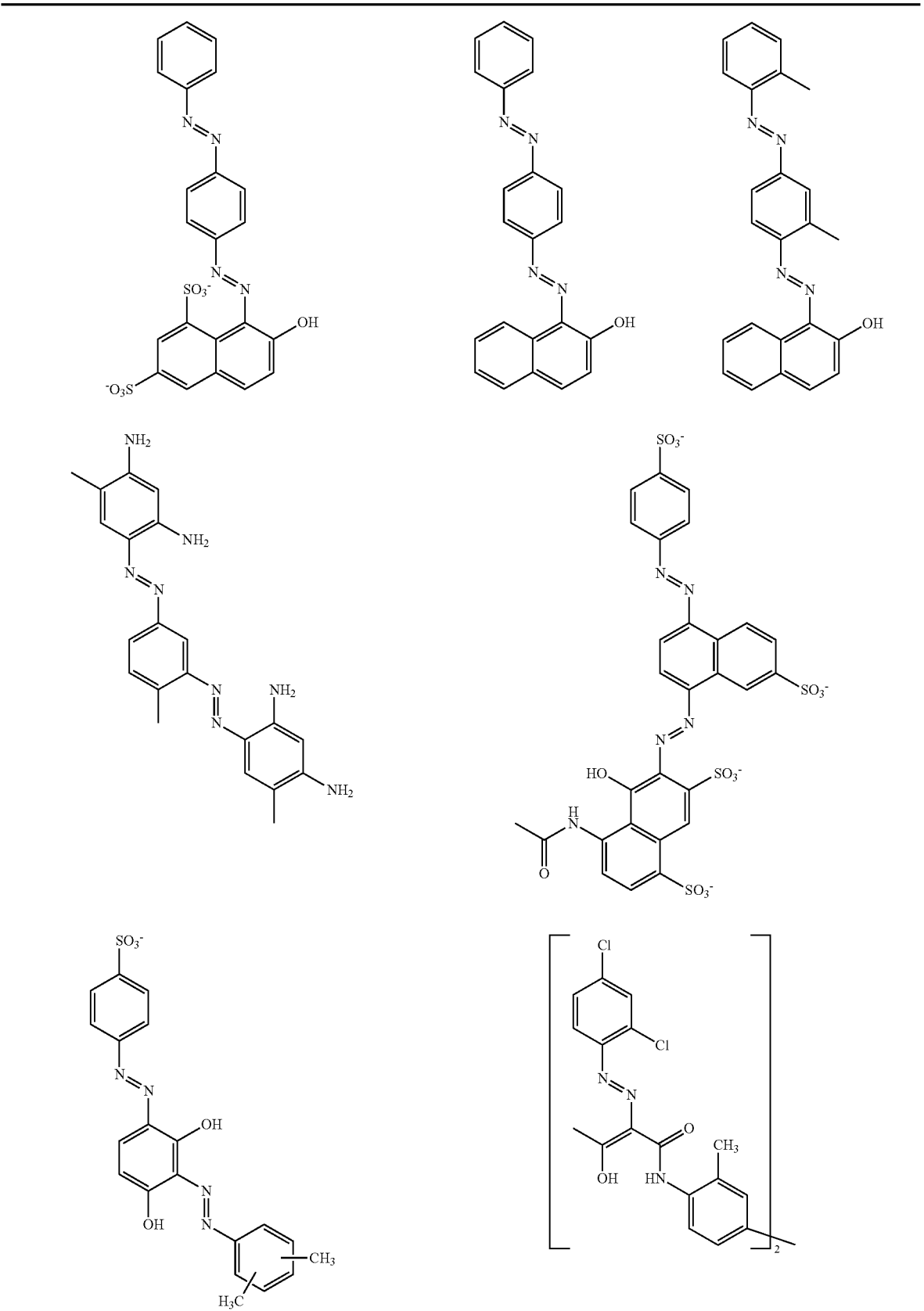

TABLE 1-continued
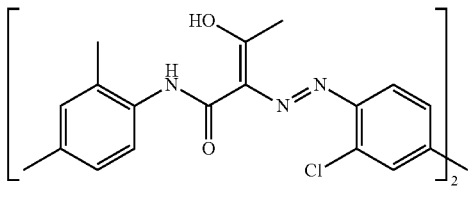
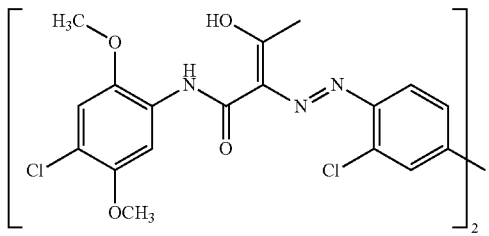
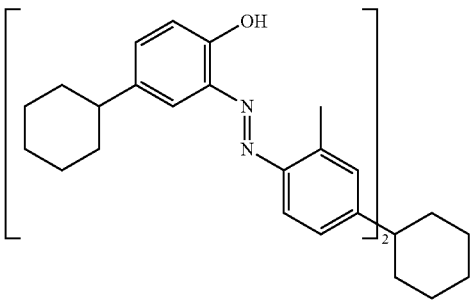
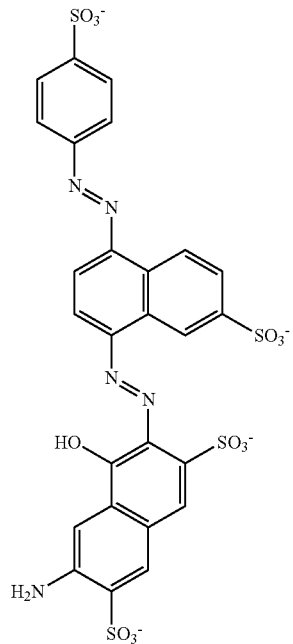
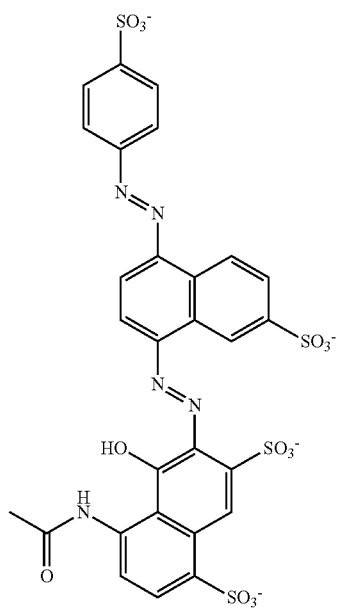
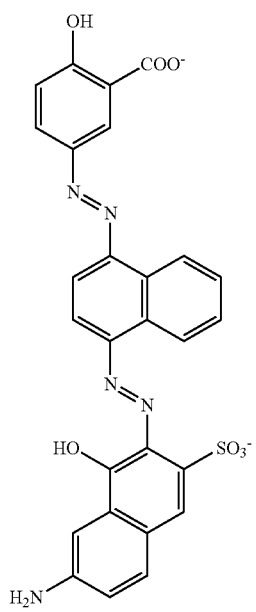

TABLE 1-continued
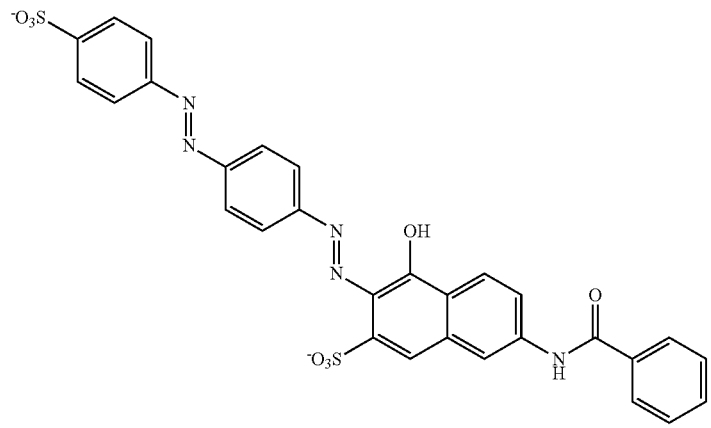
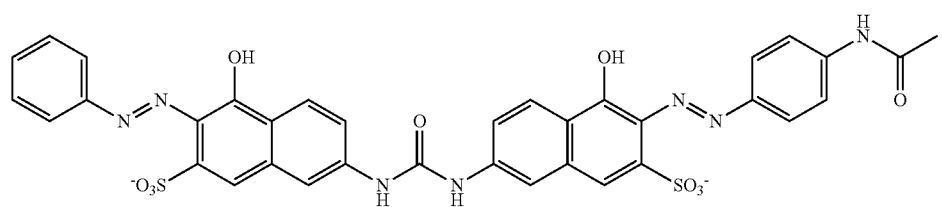
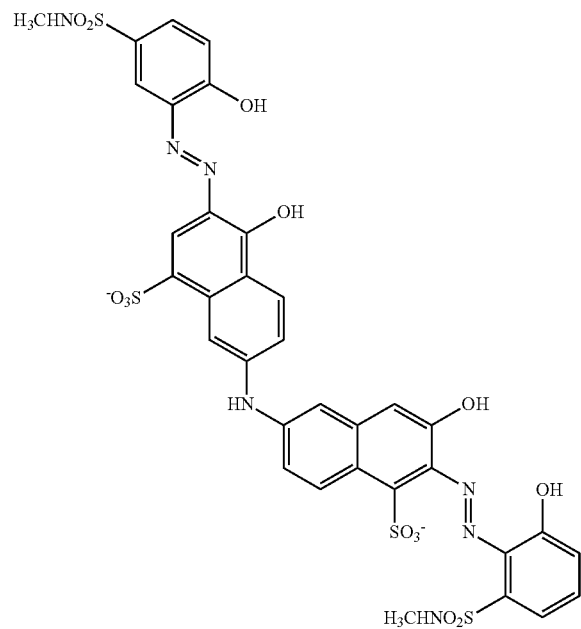

TABLE 1-continued
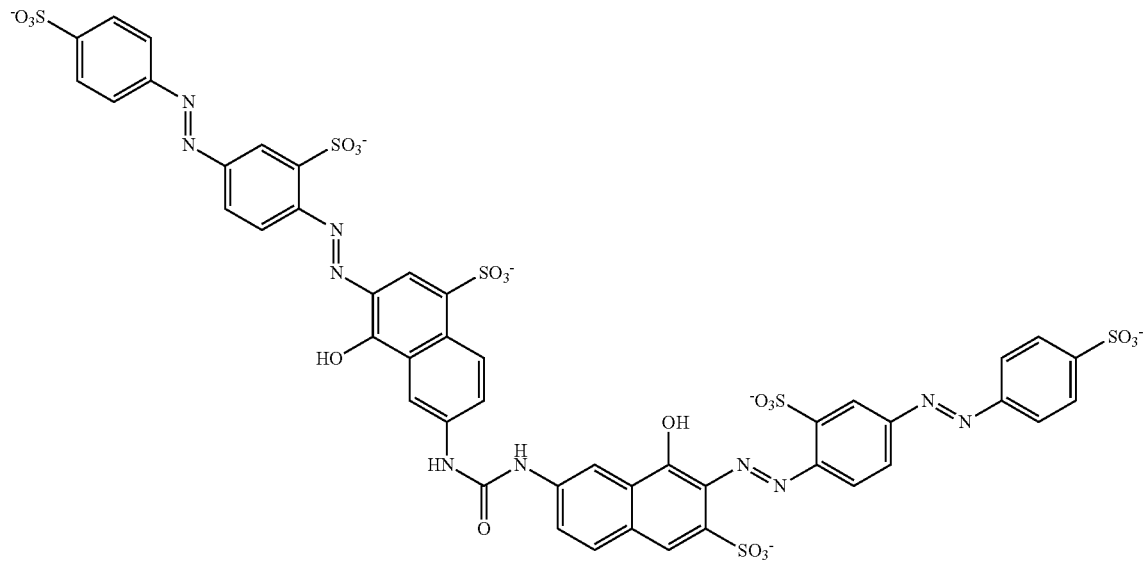
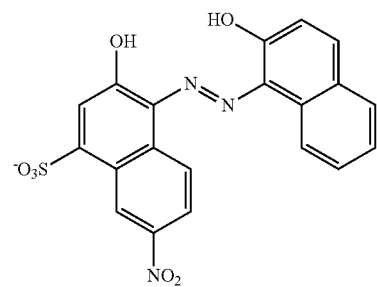
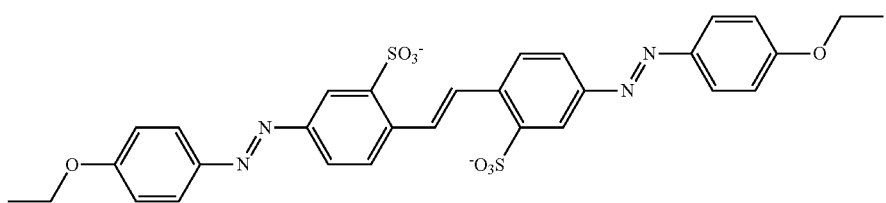
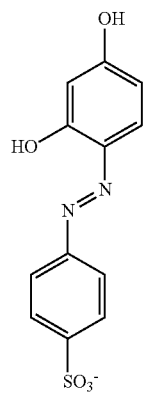
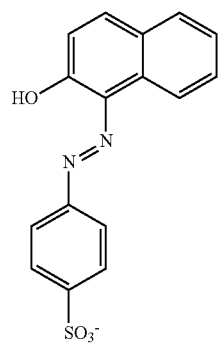
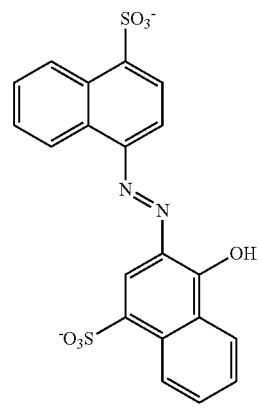

TABLE 1-continued
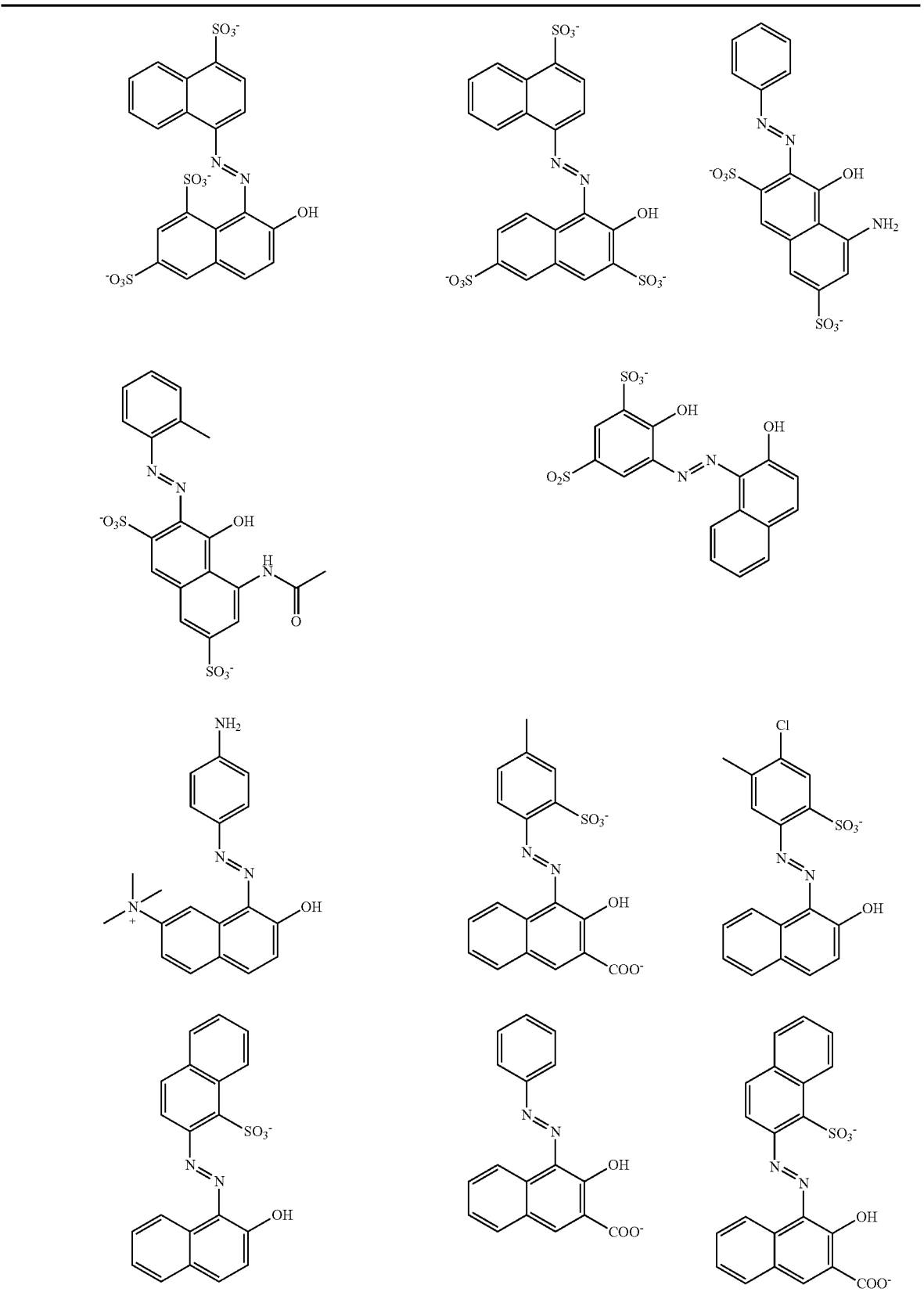

TABLE 1-continued
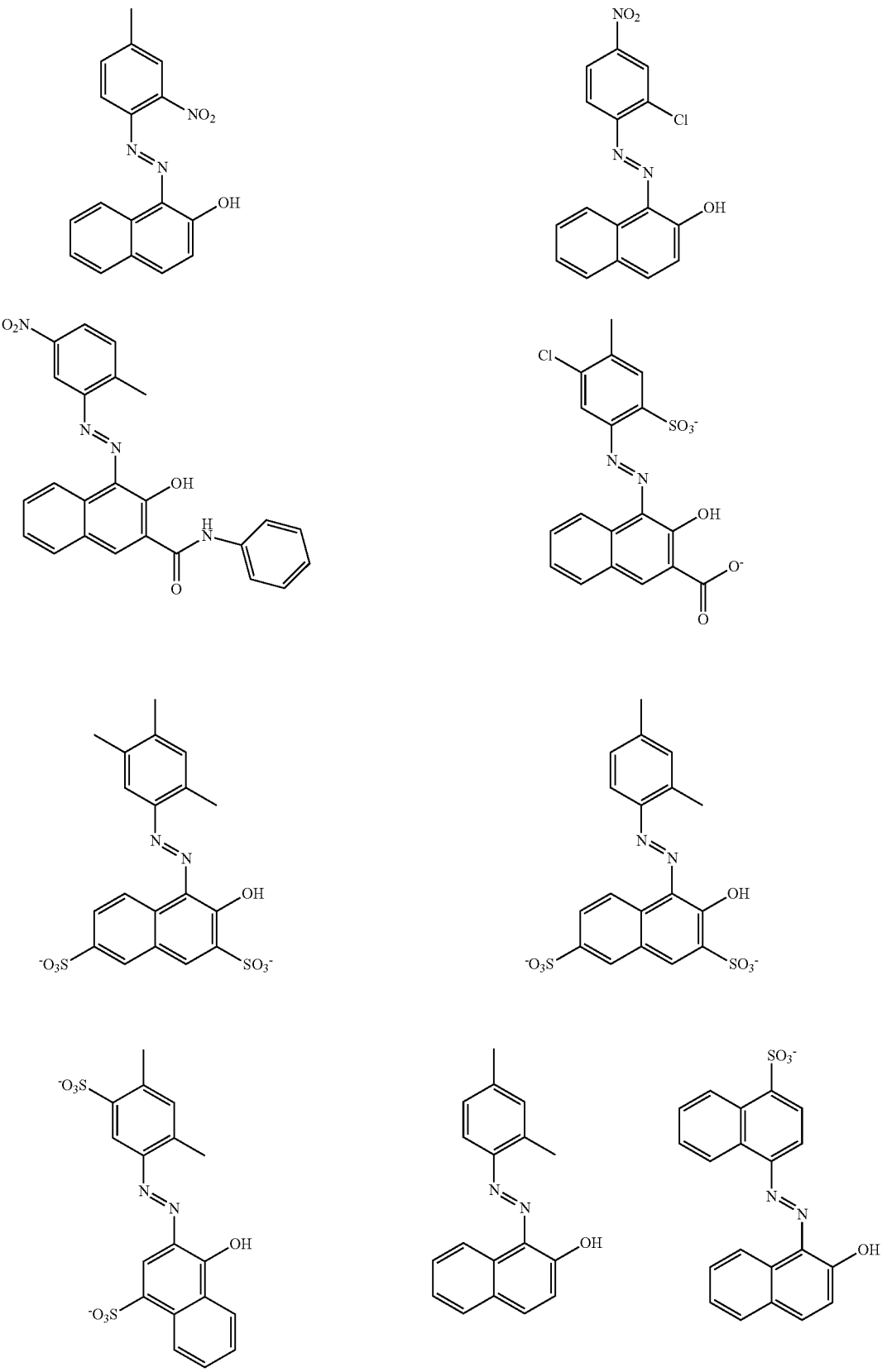

TABLE 1-continued
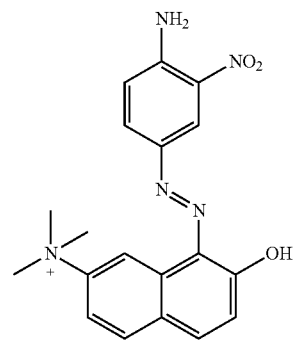 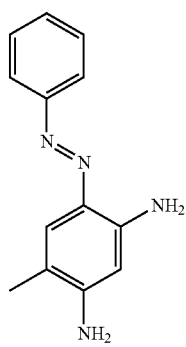 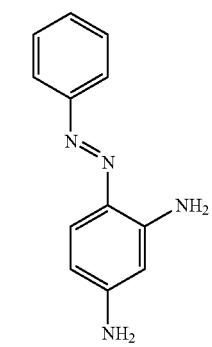
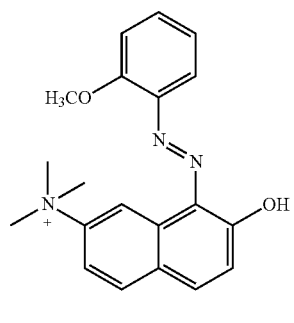 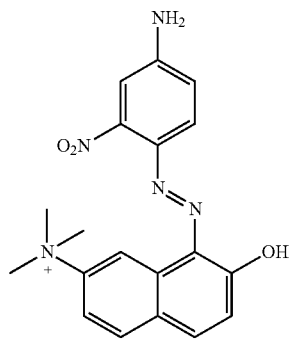 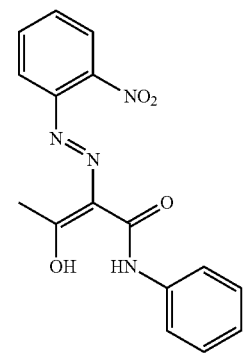
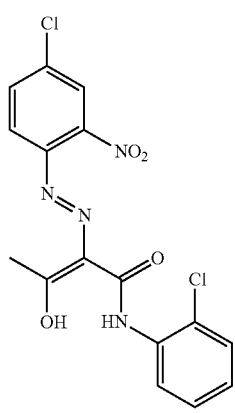 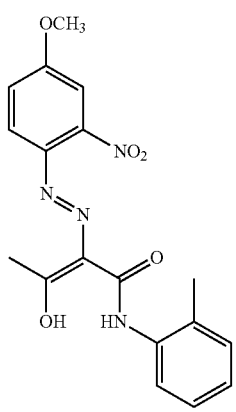 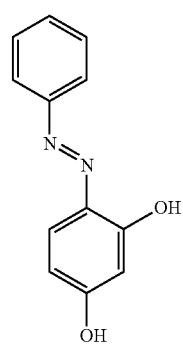
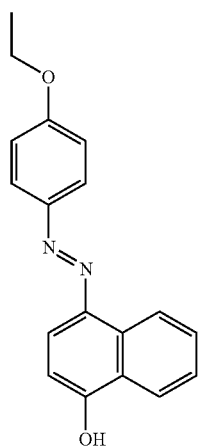 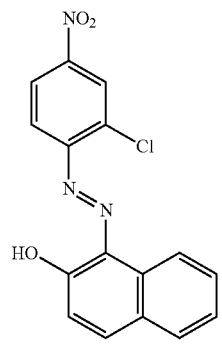 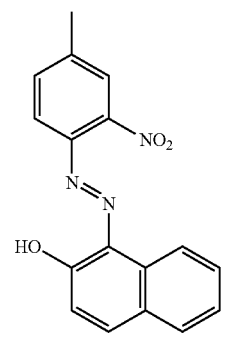

TABLE 1-continued
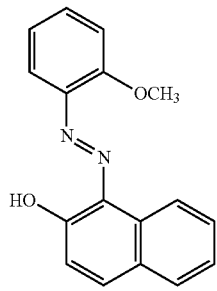 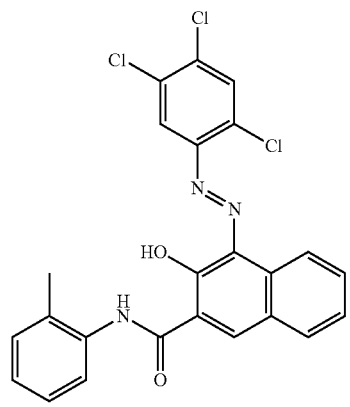
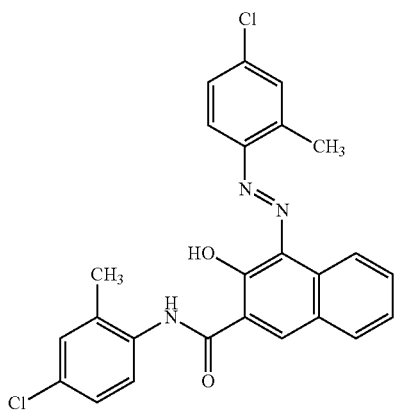 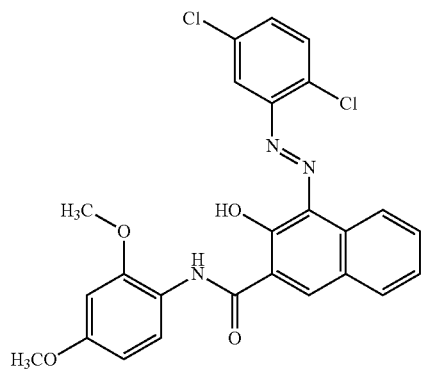
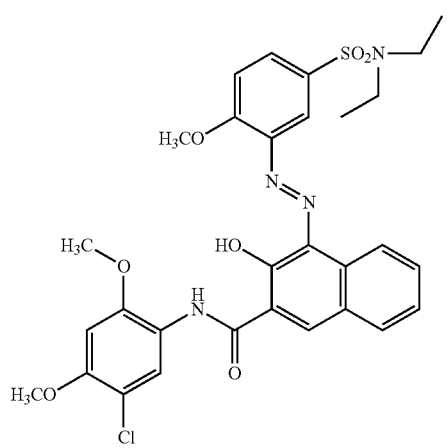 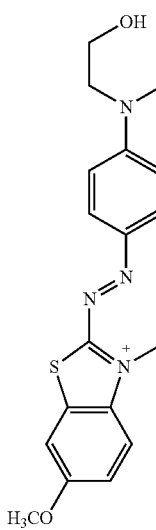 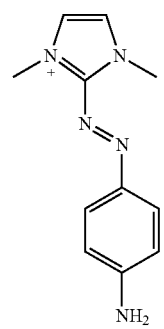

TABLE 1-continued
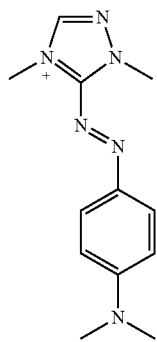 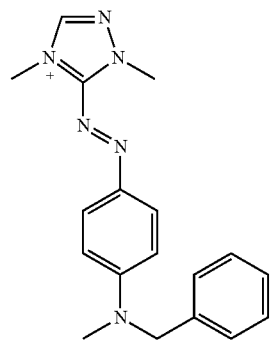
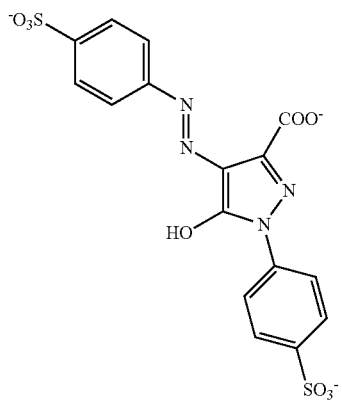 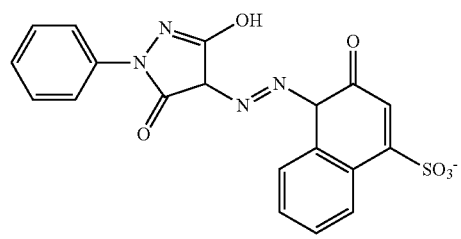
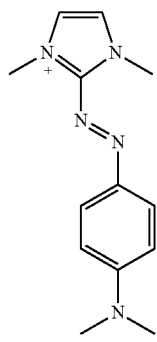 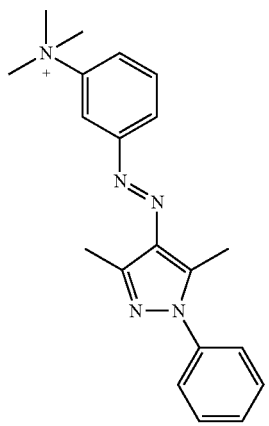 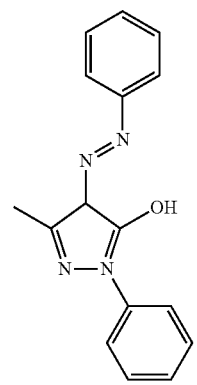
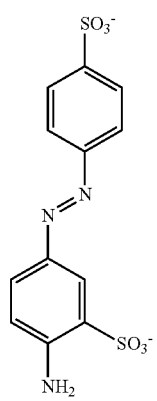 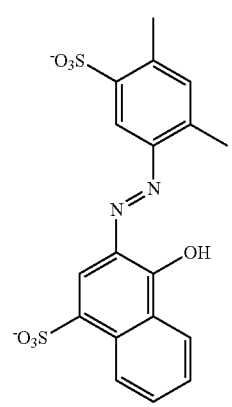

TABLE 1-continued
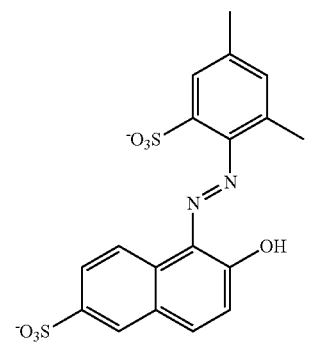 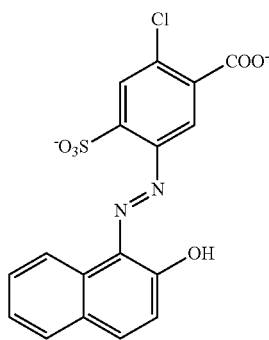 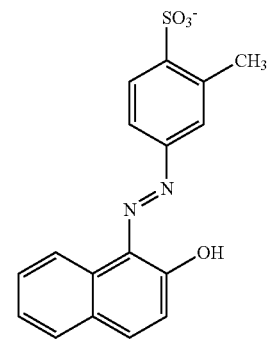
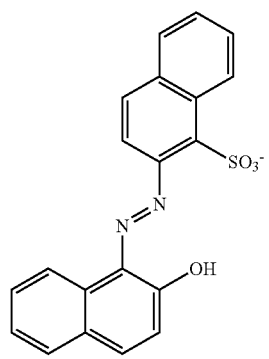 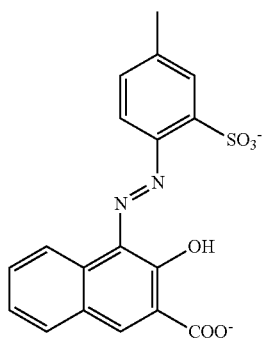
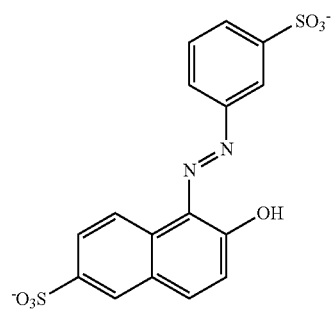 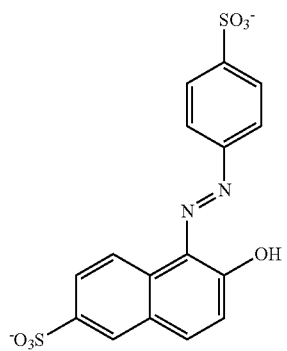
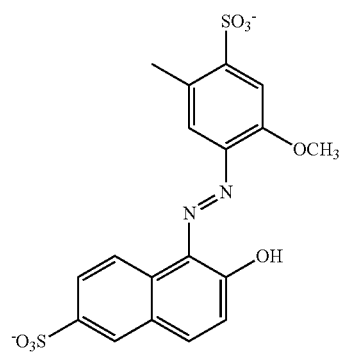 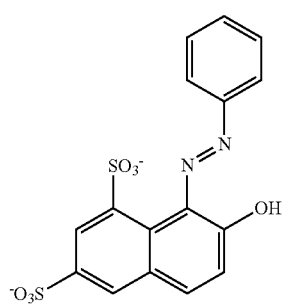

TABLE 1-continued
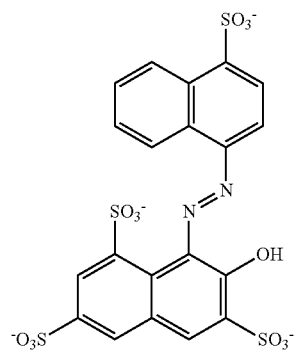 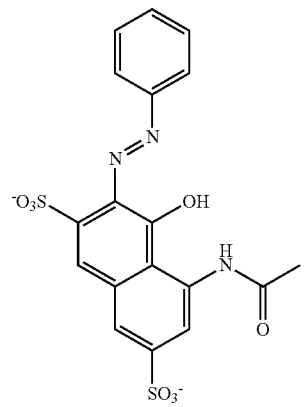
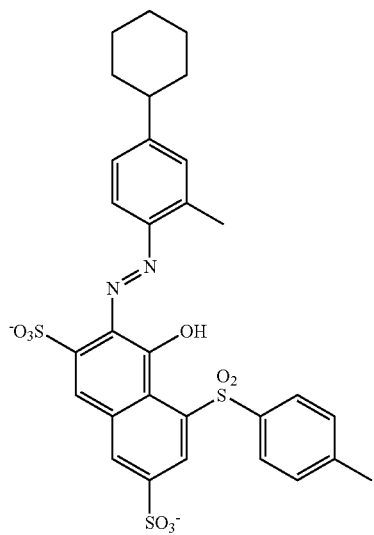 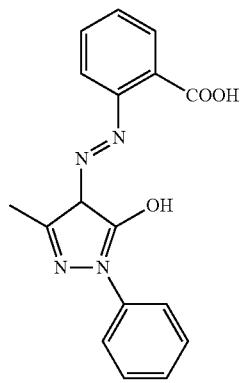 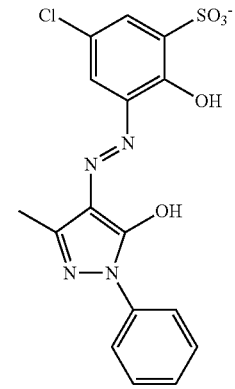
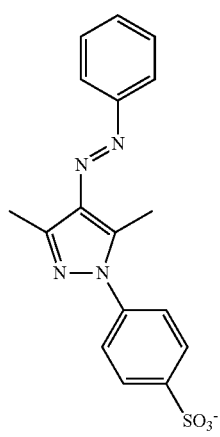 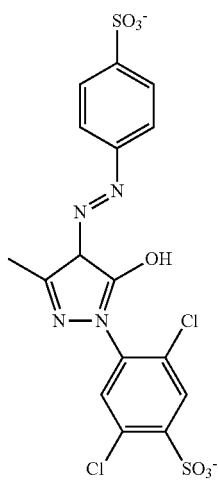 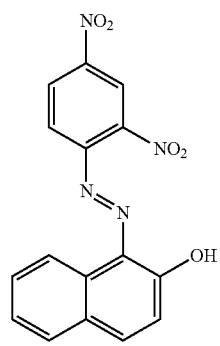

TABLE 1-continued
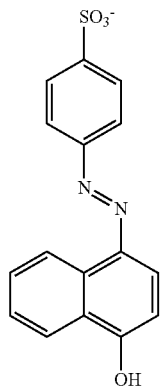 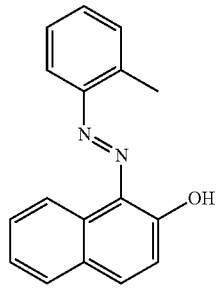 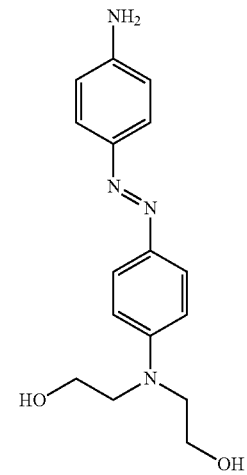
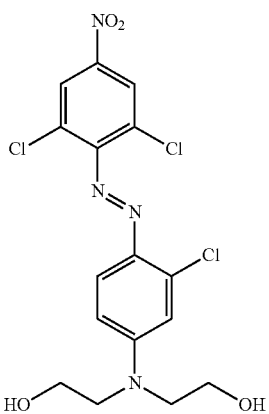 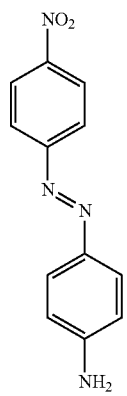 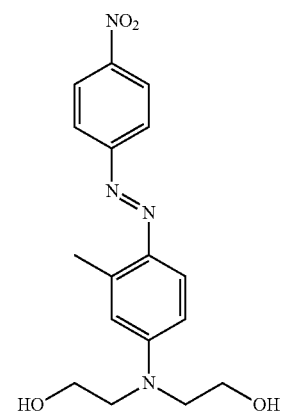
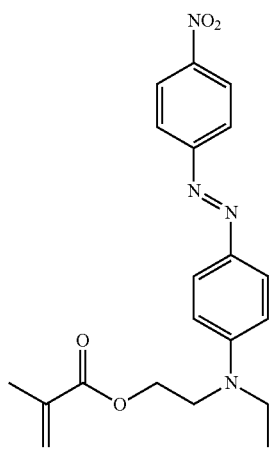 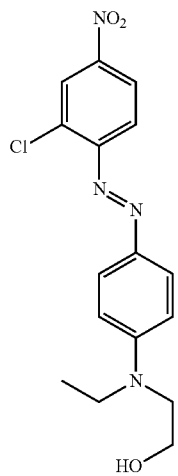

TABLE 1-continued
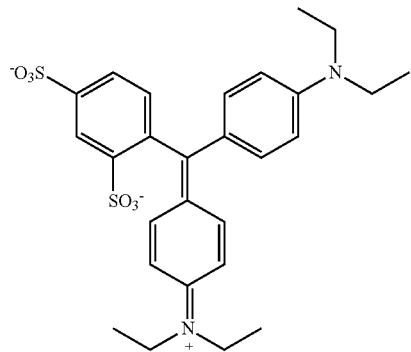
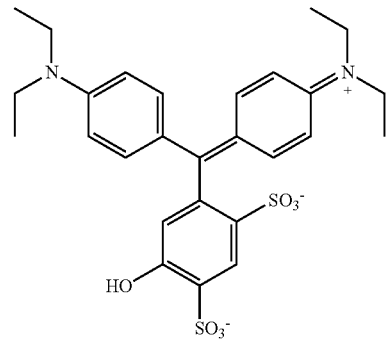
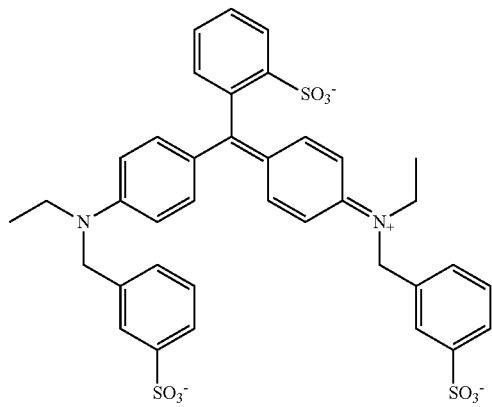
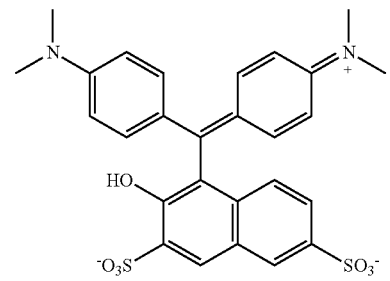
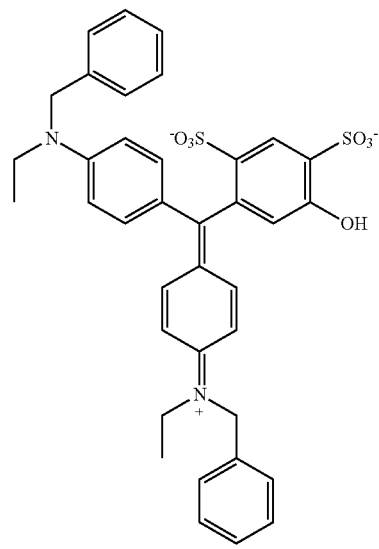
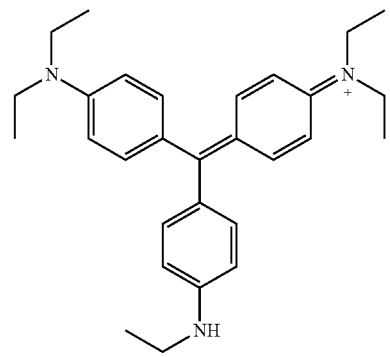

TABLE 1-continued
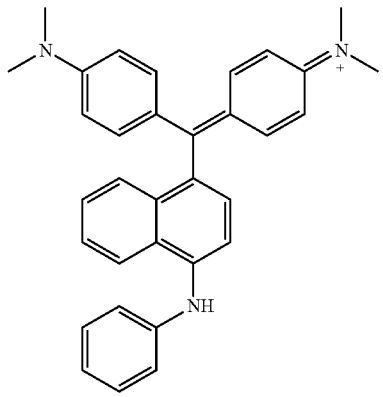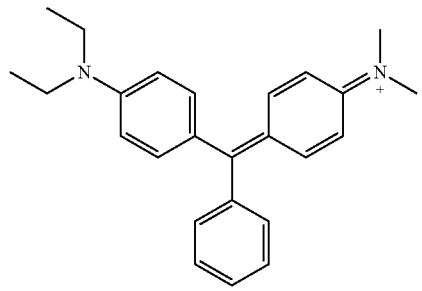
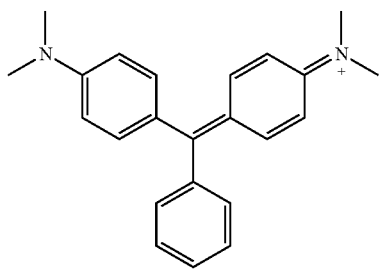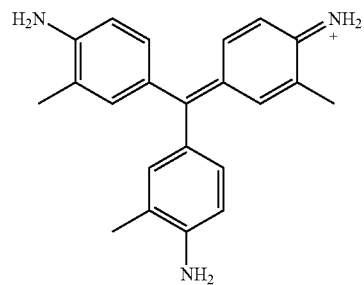
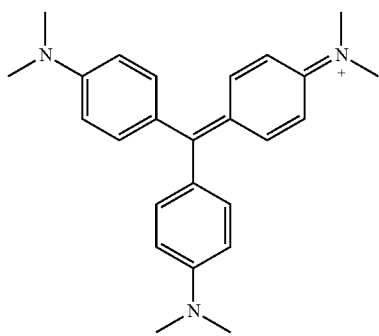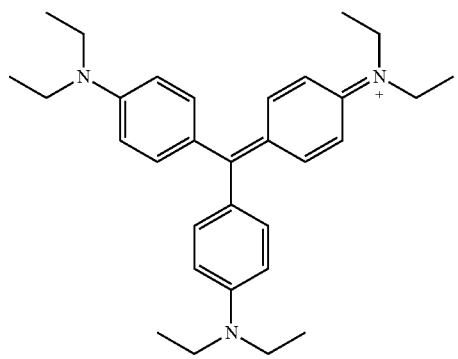
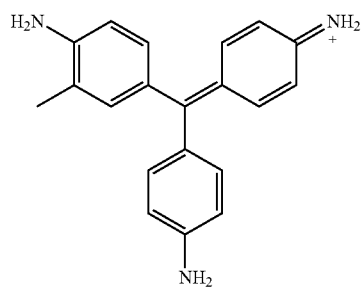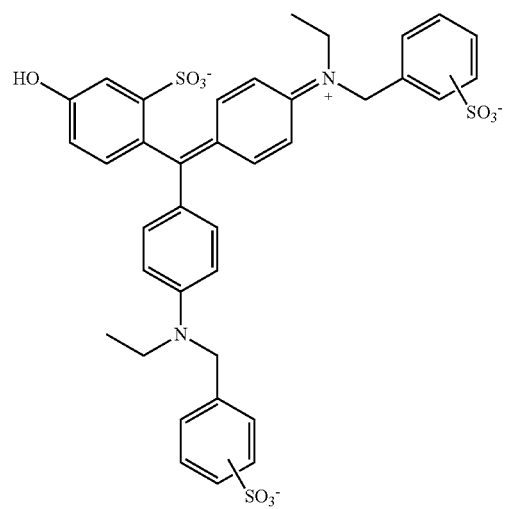

TABLE 1-continued
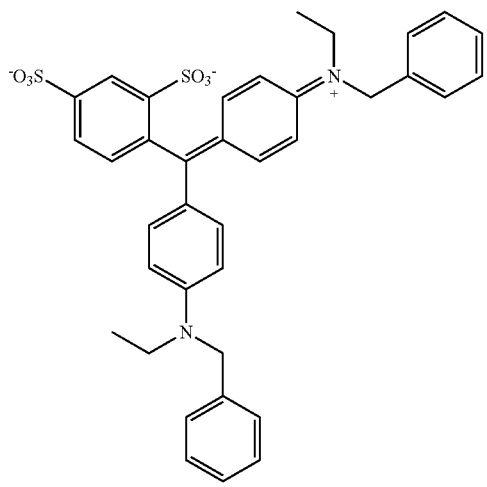
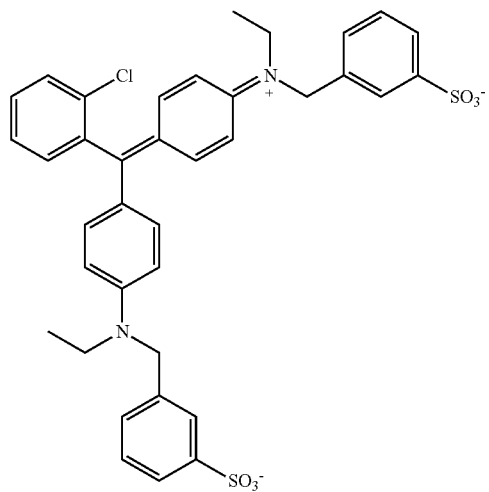
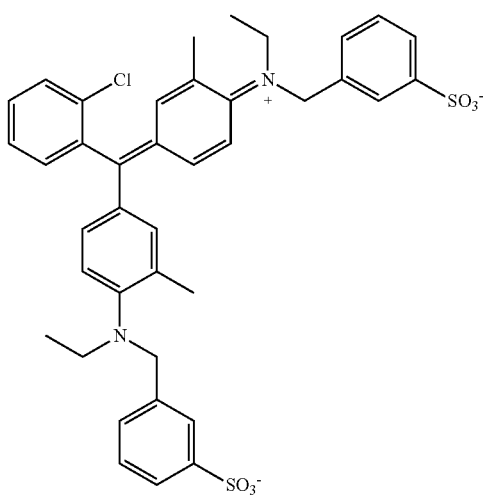
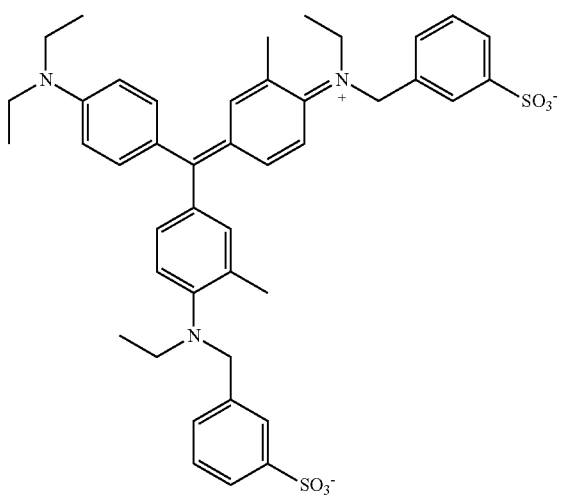
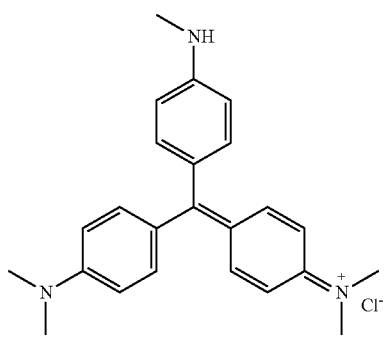
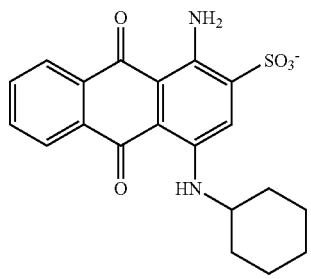

TABLE 1-continued
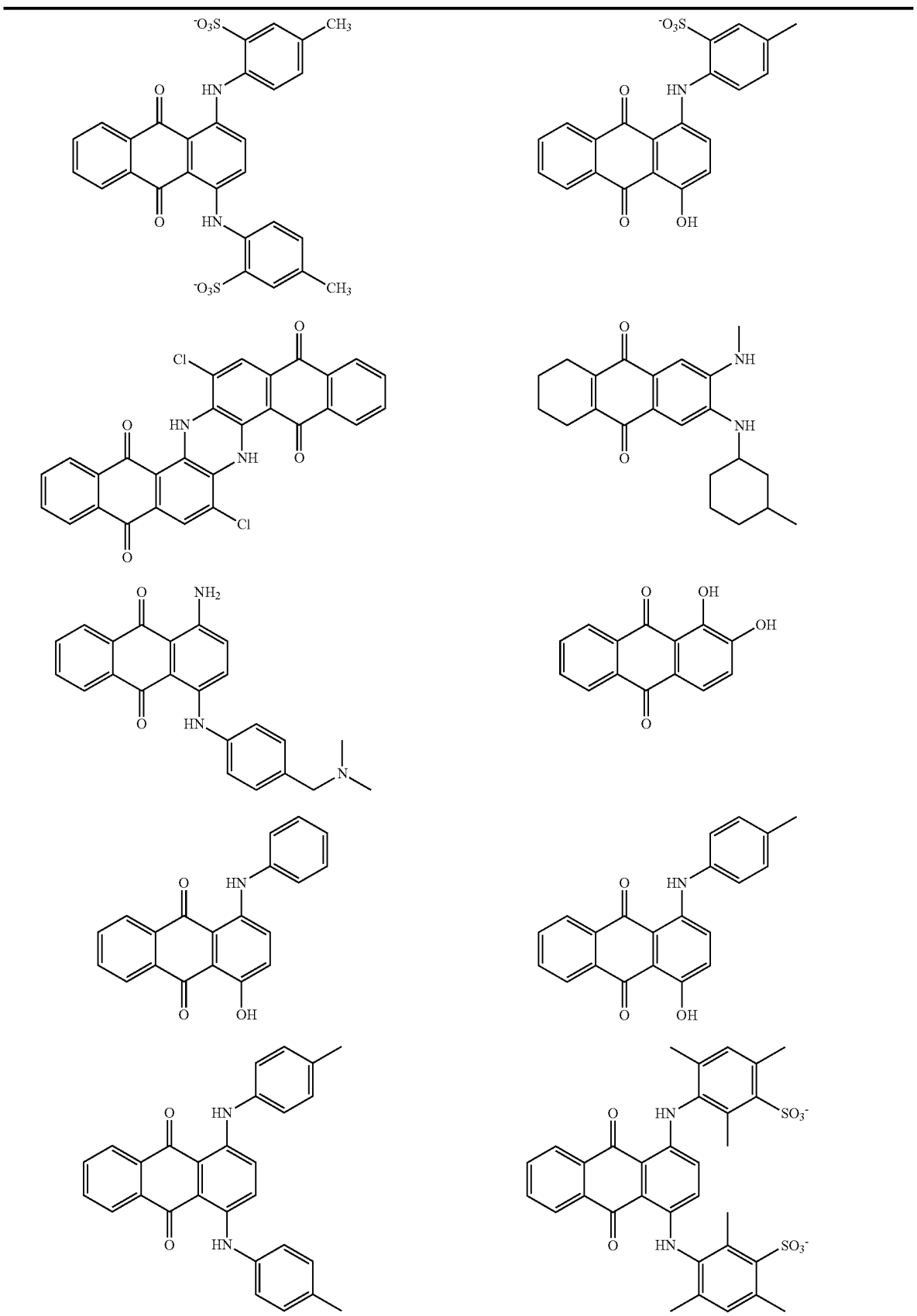

TABLE 1-continued
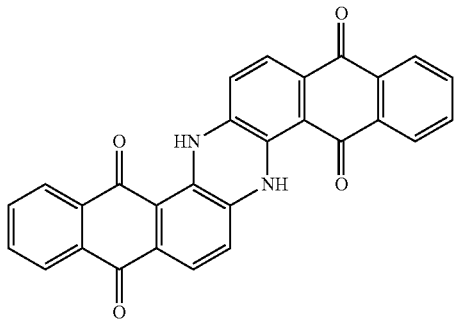 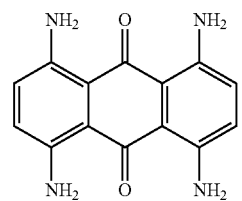
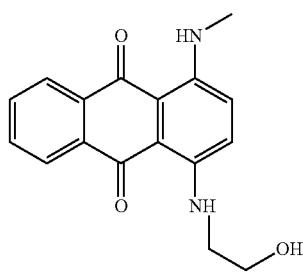 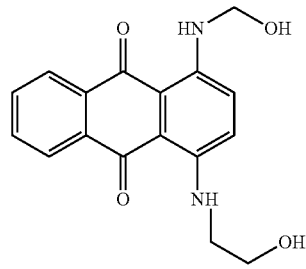
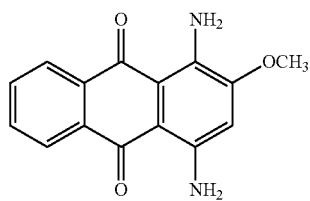 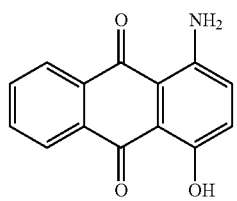 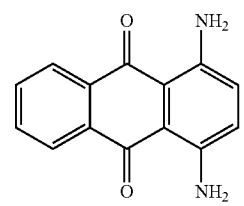
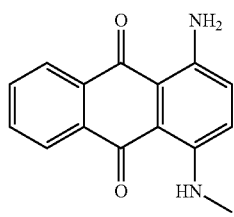 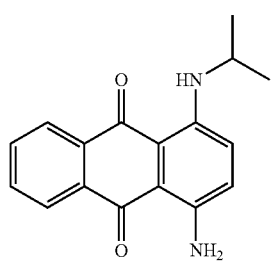
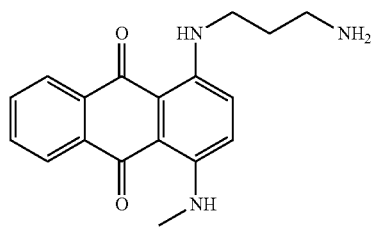 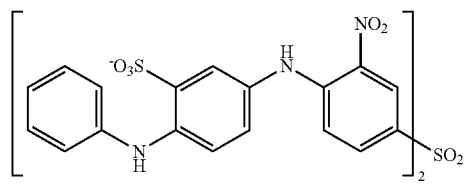

TABLE 1-continued
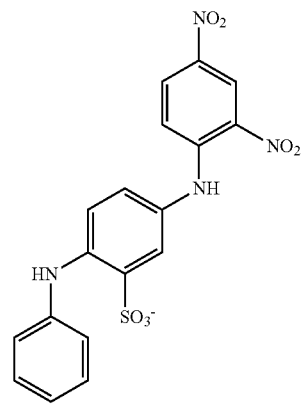 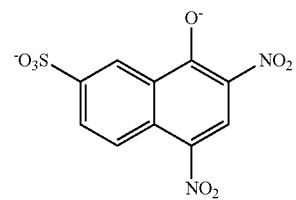
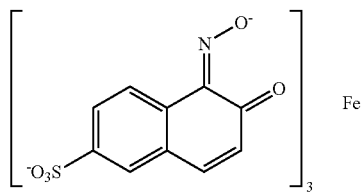 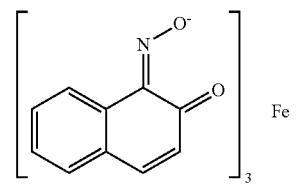
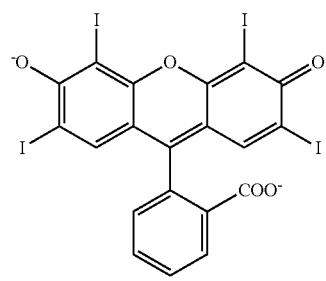 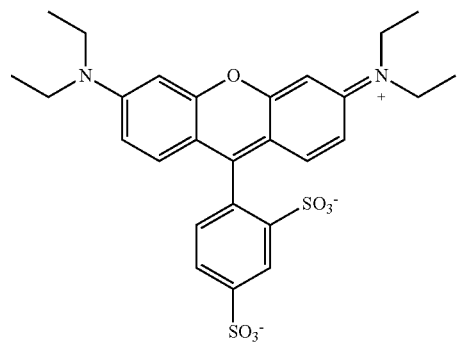
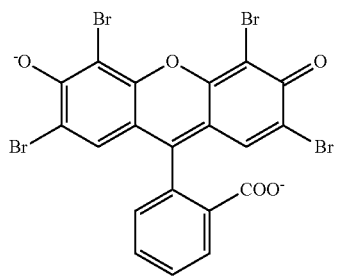 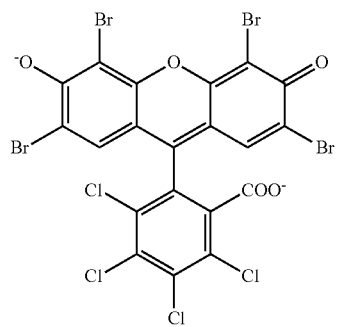

TABLE 1-continued
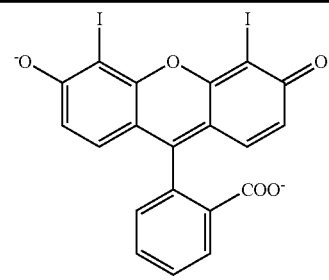 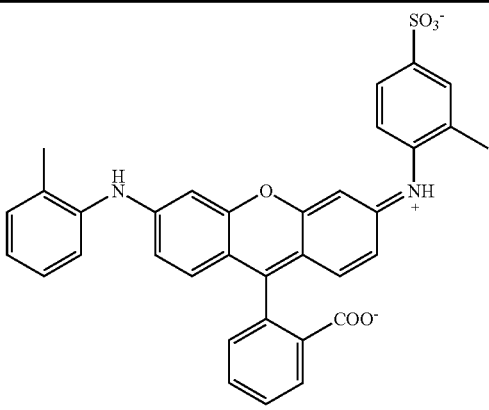
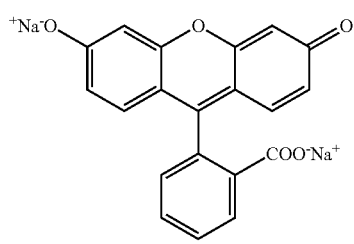 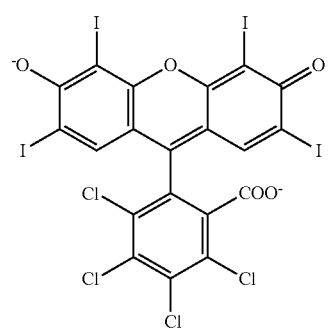
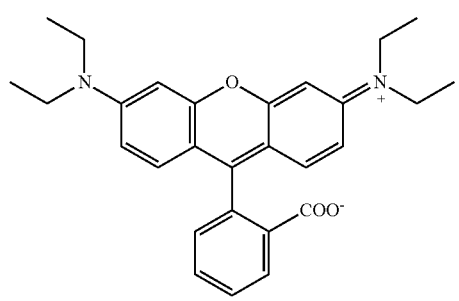 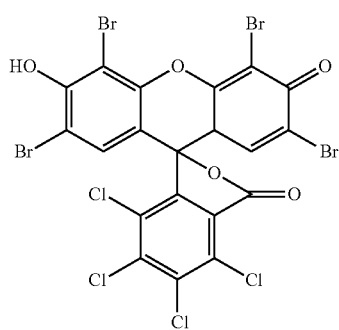
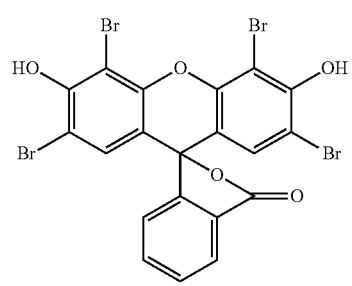 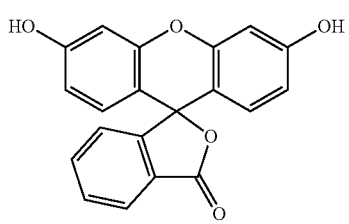
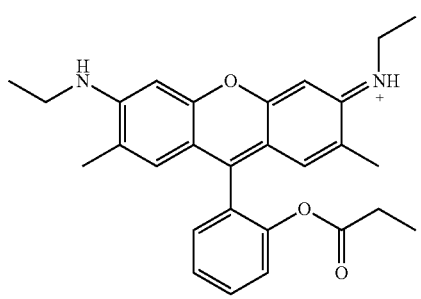 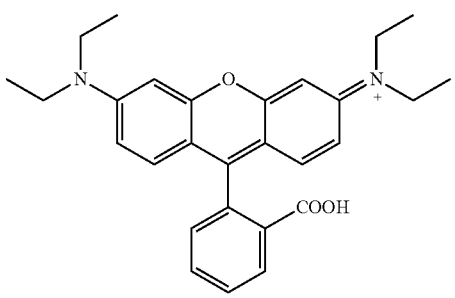

TABLE 1-continued
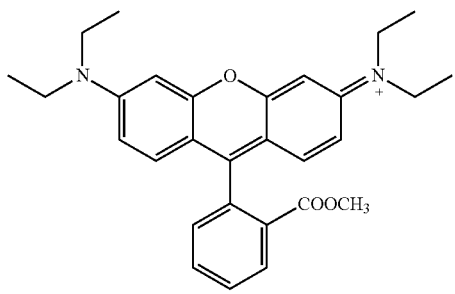
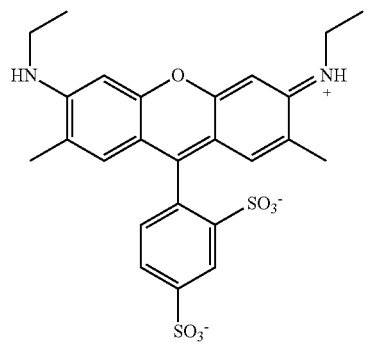
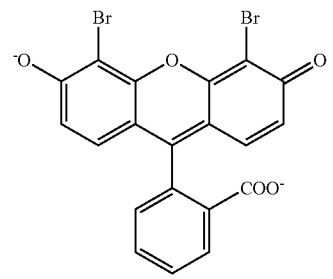
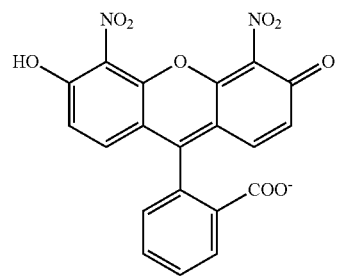
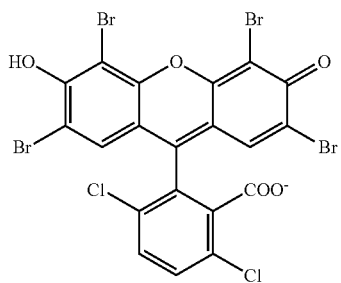
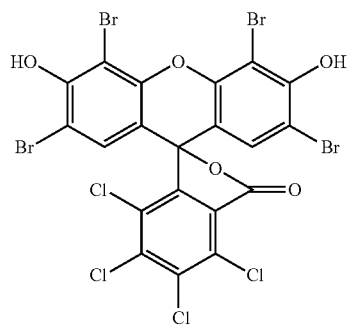
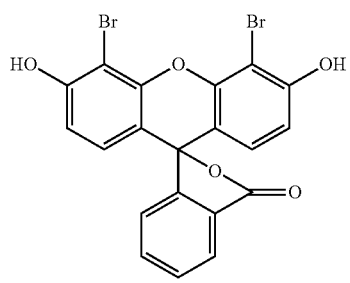
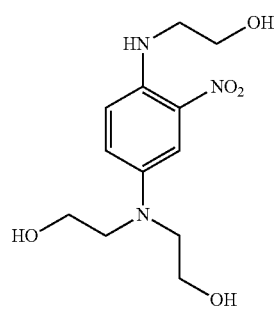
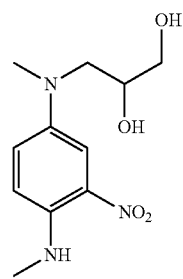
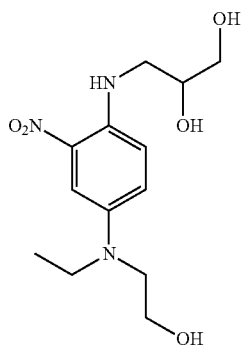
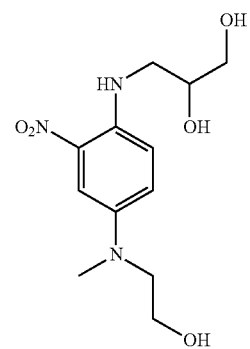

TABLE 1-continued
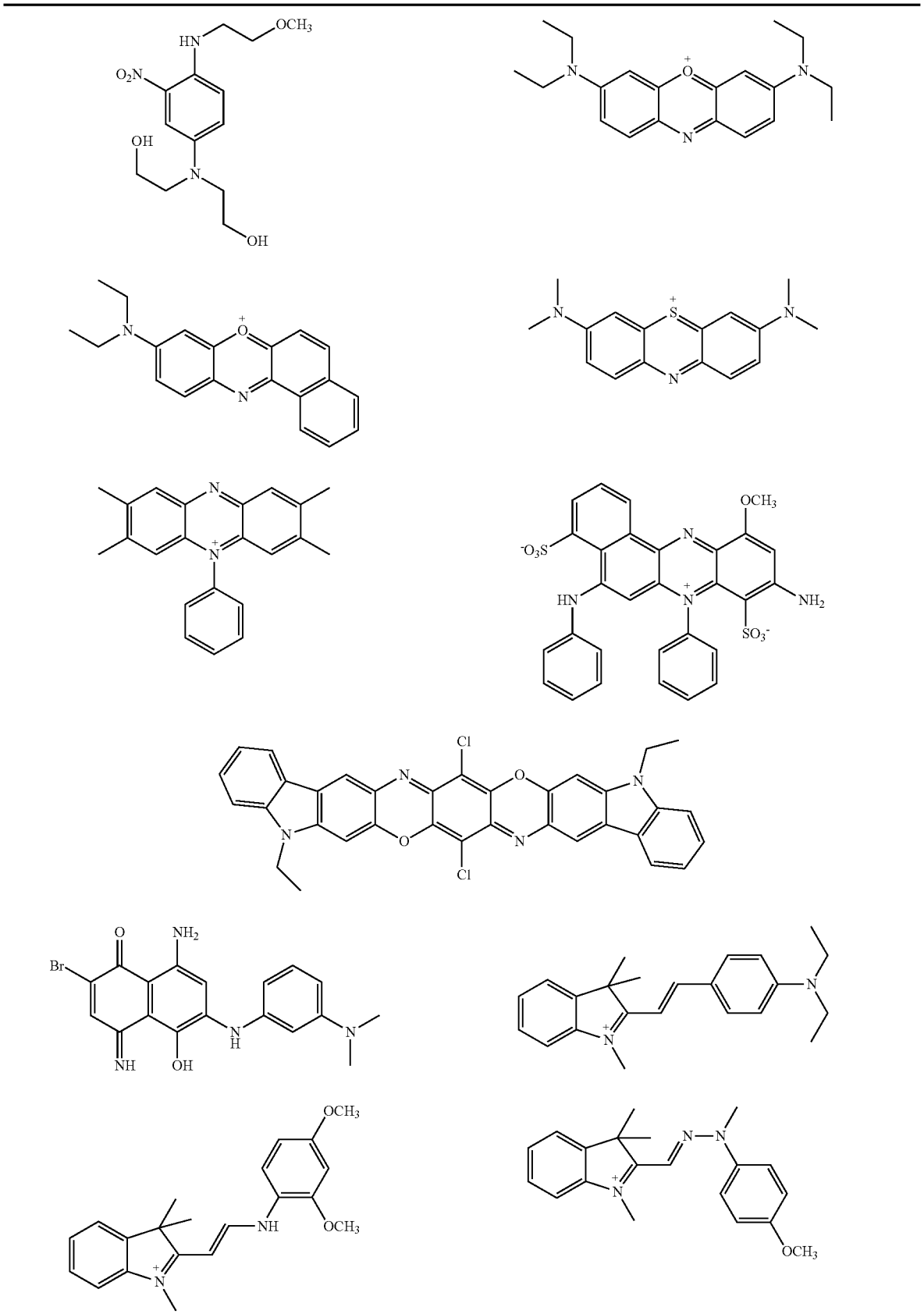

TABLE 1-continued
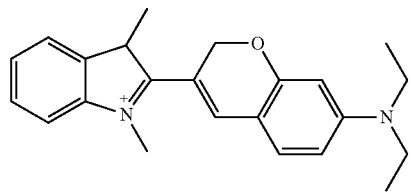
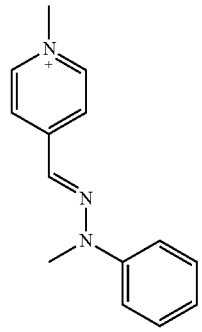
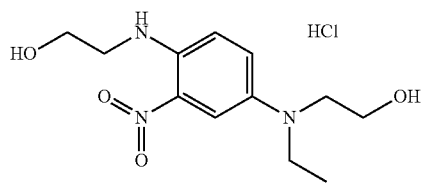
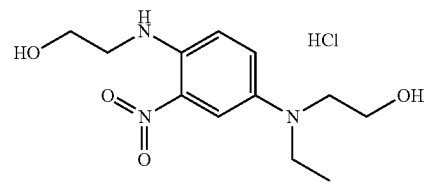
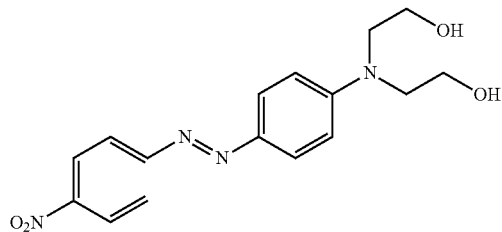
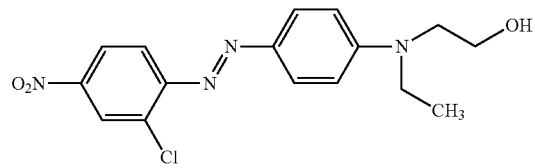
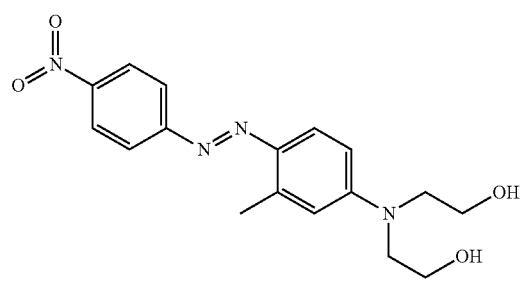
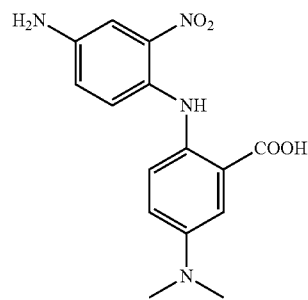
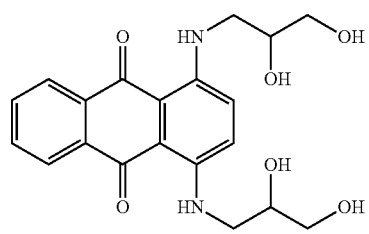
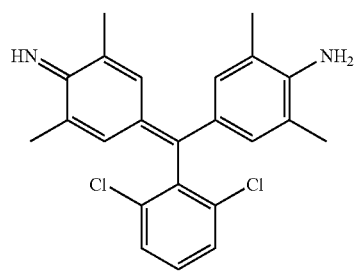

TABLE 1-continued
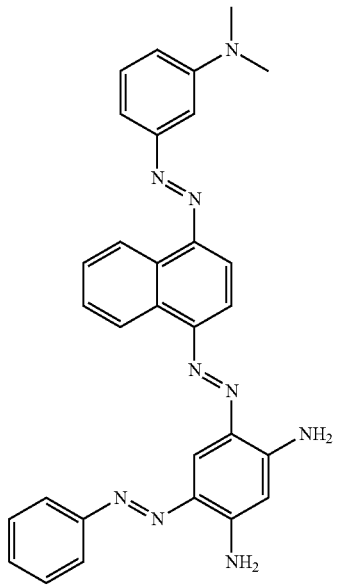
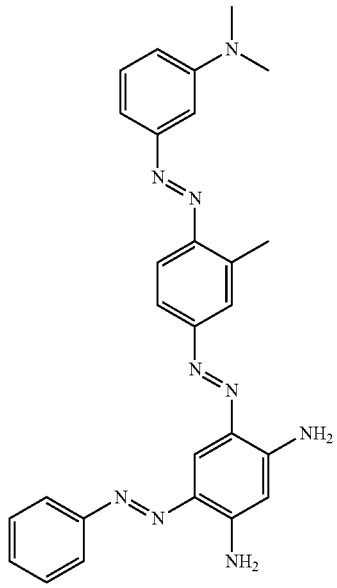
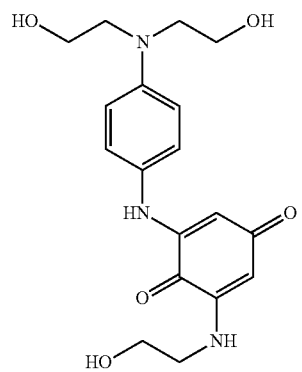
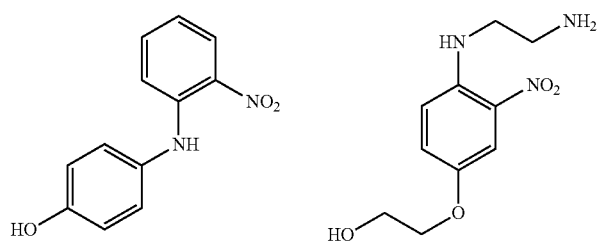
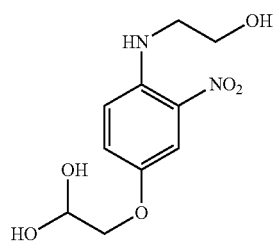
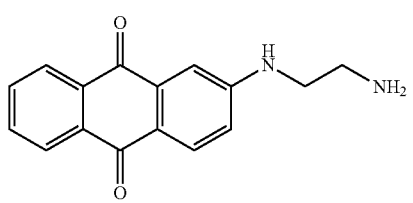
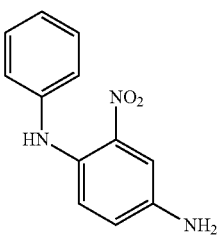
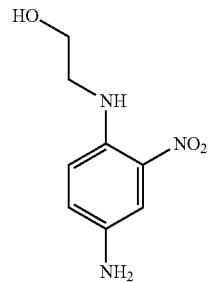
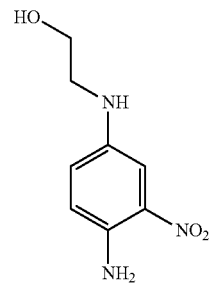

TABLE 1-continued
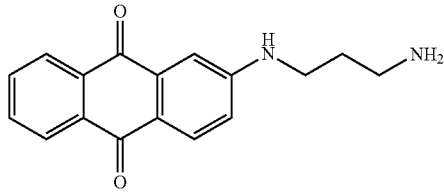
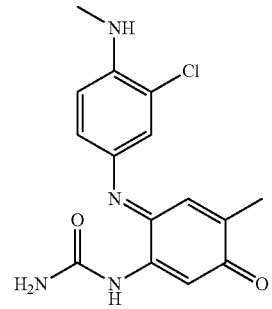
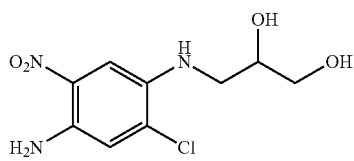
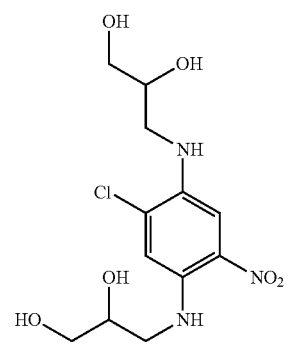
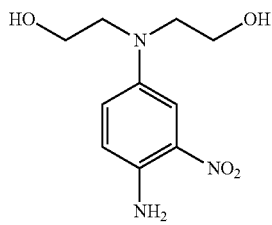
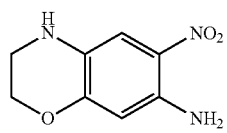
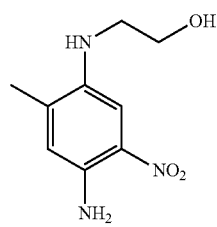
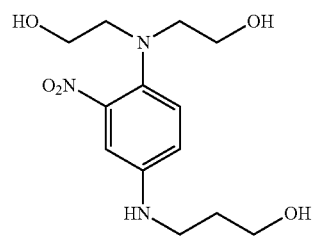
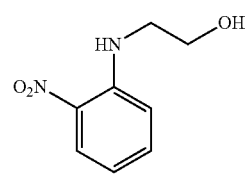
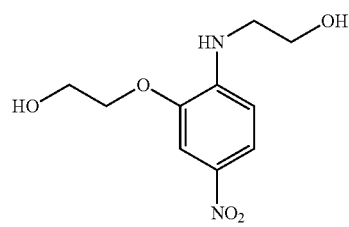
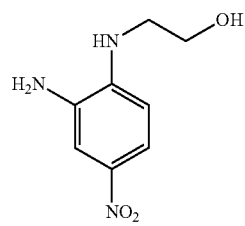
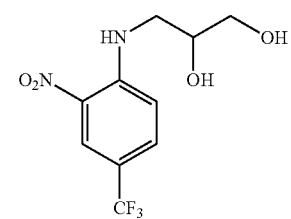

TABLE 1-continued

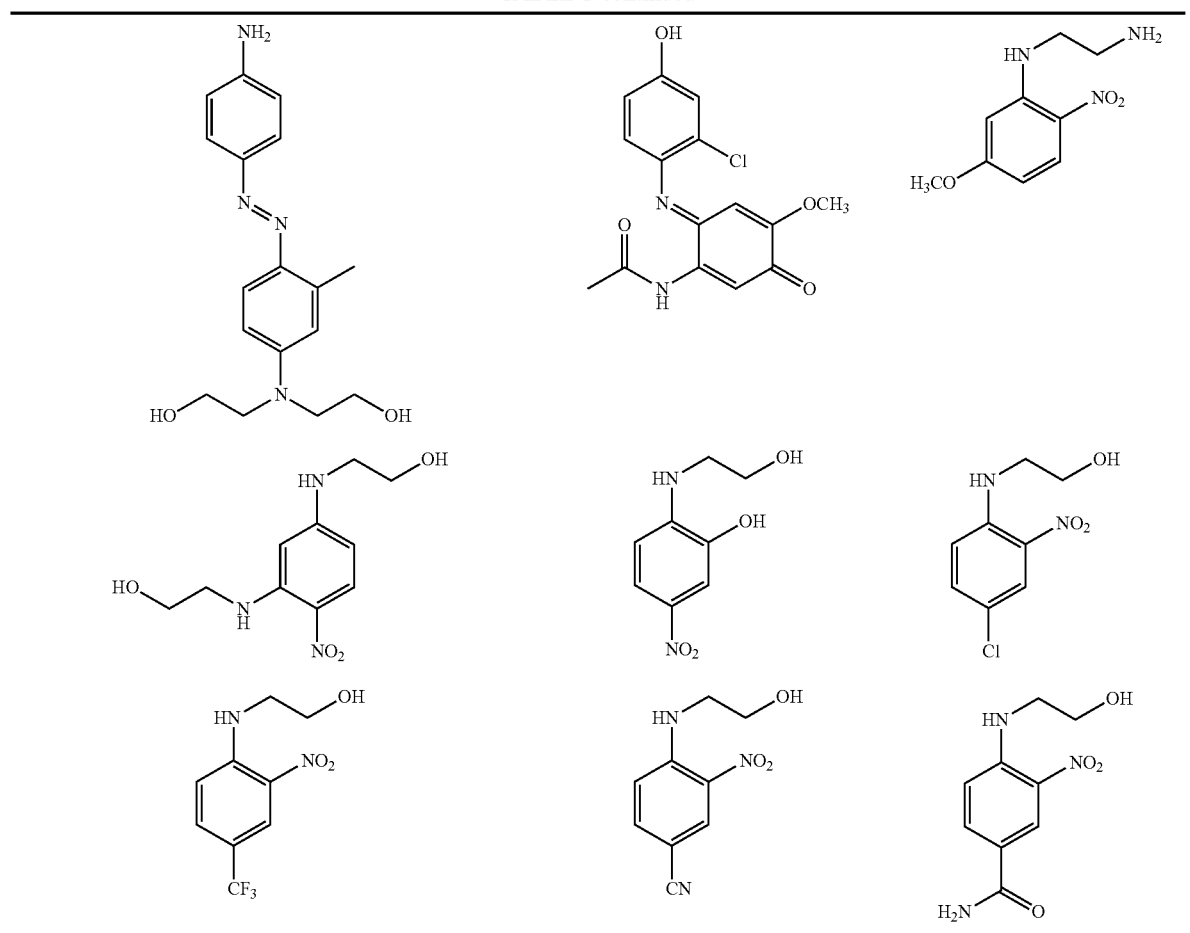

and cosmetically acceptable salts thereof.

In one embodiment, the color fastness moiety (e.g., F) of formulae Ia and Ib is linked (e.g., covalently bound) to the chromophore (e.g., C and C*) via a linker (e.g., L and L*, respectively). The term "linker" includes chemical moieties that are capable of linking (e.g., by a covalent bond) the chromophore to the color fastness moiety.

In some embodiments, the linker has at least one hydrogen bond donor moiety. In some embodiments, the color fastness moiety has at least one hydrogen bond donor moiety and at least one hydrogen bond acceptor moiety. In some embodiments, the color fastness moiety together with the linker comprise at least one hydrogen bond donor and at least one hydrogen bond acceptor. In some embodiments, the color fastness moiety together with the linker comprise at least 2 hydrogen bond donors and at least one hydrogen bond acceptor.

The language "hydrogen bond donor moiety" includes those chemical groups that have a hydrogen covalently bonded to an electronegative atom, for example, oxygen, nitrogen, fluorine, and the like. In some embodiments, the hydrogen bond donor moiety is a hydroxyl or a primary (e.g., —NH$_2$) or secondary amino moiety (e.g., —NHR).

The language "hydrogen bond acceptor moiety" includes electronegative atoms that have lone pair of electrons with which to interact non-covalently with the hydrogen of the hydrogen bond donor. Examples of hydrogen bond acceptor moieties include oxygen, nitrogen and fluorine. In some embodiments, the hydrogen bond acceptor moiety is a primary, secondary or tertiary amino moiety (e.g., —NR$_2$), a hydroxyl moiety, an ether moiety (e.g., —R—O—R) or CF$_3$.

In some embodiments, the linker and the colorfastness moiety together have at least three amino moieties. In some embodiments, at least one of the amino moieties is a tertiary amine.

In other embodiments, linker L is of formula III:

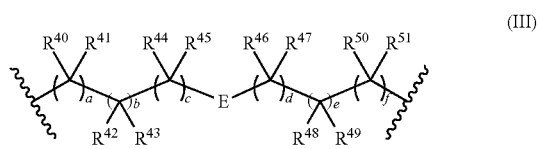

(III)

wherein

L covalently links C via the left hand portion of formula III to F via the right hand side of formula III;

E is NR$^{52}$, O, S, SO$_2$, SO$_3$, C=A, NR$^{53}$C=A, C(=A)NR$^{54}$, NR$^{55}$C(=A)NR$^{56}$, (C=A)O, OC=A or

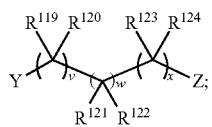

A, A* and A** are each independently oxygen or sulfur;

Y is $NR^{125}$, O, S, $SO_2$, $SO_3$, C=A*, $NR^{126}C=A*$, $C(=A*)NR^{127}$, $NR^{128}C(=A*)NR^{129}$, (C=A*)O or OC=A*;

Z is $NR^{130}$, O, S, $SO_2$, $SO_3$, C=A, $NR^{131}C=A$, $C(=A)NR^{132}$, $NR^{133}C(=A)NR^{134}$, (C=A)O or OC=A;

a, b, c, d, e, f, v, w and x are each independently an integer between 0 and 5, provided that at least one of a, b, c, d, e, f, v, w and x is not 0;

$R^{40}$ and $R^{41}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{40}$ and $R^{41}$ are absent when a is 0;

$R^{42}$ and $R^{43}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{42}$ and $R^{43}$ are absent when b is 0;

$R^{44}$ and $R^{45}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{44}$ and $R^{45}$ are absent when c is 0;

$R^{46}$ and $R^{47}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{46}$ and $R^{47}$ are absent when d is 0;

$R^{48}$ and $R^{49}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{48}$ and $R^{49}$ are absent when e is 0;

$R^{50}$ and $R^{51}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{50}$ and $R^{51}$ are absent when f is 0;

$R^{119}$ and $R^{120}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{119}$ and $R^{120}$ are absent when v is 0;

$R^{121}$ and $R^{122}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{121}$ and $R^{122}$ are absent when w is 0;

$R^{123}$ and $R^{124}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{123}$ and $R^{124}$ are absent when x is 0; or $R^{40}$ and $R^{41}$ or $R^{41}$ and $R^{42}$ or $R^{42}$ and $R^{43}$ or $R^{43}$ and $R^{44}$ or $R^{44}$ and $R^{45}$ or $R^{45}$ and $R^{46}$ or $R^{46}$ and $R^{47}$ or $R^{47}$ and $R^{48}$ or $R^{48}$ and $R^{49}$ or $R^{49}$ and $R^{50}$ or $R^{50}$ and $R^{51}$ or $R^{119}$ and $R^{120}$ or $R^{120}$ and $R^{121}$ or $R^{121}$ and $R^{122}$ or $R^{123}$ and $R^{124}$, together with the carbon atoms to which they are attached are linked to form a 3 to 10-membered carbocyclic or heterocyclic ring;

$R^{52}$, $R^{53}$, $R^{54}$, $R^{55}$, $R^{56}$, $R^{125}$, $R^{126}$, $R^{127}$, $R^{128}$; $R^{129}$; $R^{130}$, $R^{131}$, $R^{132}$, $R^{133}$ and $R^{134}$ are each independently hydrogen, hydroxy, alkoxy, alkyl, alkenyl, alkynyl, aryl, carbonyl, carboxy, acyl or $NR^{57}R^{58}$; and $R^{57}$ and $R^{58}$ are each independently hydrogen, alkyl, alkenyl, alkynyl, aryl, a heterocyclic moiety or carbonyl.

In some embodiments, the linker L is of formula IIIa:

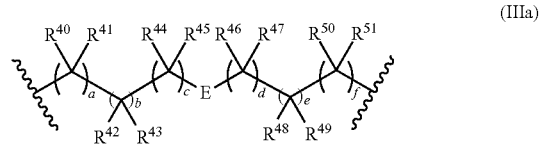

(IIIa)

wherein

L covalently links C via the left hand side of formula IIIa to F via the right hand side of formula IIIa;

a, b, c, d, e, and f are each independently an integer from 0-2, provided that at least one of a, b, c, d, e and f is not 0;

$R^{40}$, $R^{41}$, $R^{42}$, $R^{43}$, $R^{44}$, $R^{45}$, $R^{46}$, $R^{47}$, $R^{48}$, $R^{49}$, $R^{50}$ and $R^{51}$ are each independently absent or hydrogen;

E is $NR^{52}$ or $NR^{53}C=O$;

$R^{52}$ and $R^{53}$ are each independently hydrogen or alkyl.

In some embodiments, a, b, c and d are each 0.
In some embodiments, e and f are each 1.
In some embodiments, E is $NR^{52}$.
In some embodiments, $R^{52}$ is hydrogen.
In some embodiments, $R^{52}$ is alkyl (e.g., ethyl).
In other embodiments, L* is of formula IV:

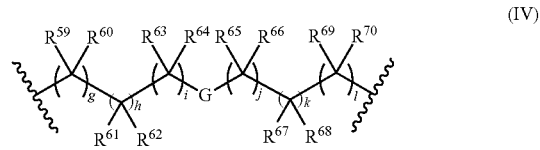

(IV)

wherein

L* is covalently bound to C* via the left hand side of formula IV;

G is $NR^{71}$, O, S, $SO_2$, $SO_3$, C=J, $NR^{72}C=J$, $C(=J)NR^{73}$, $NR^{74}C(=J)NR^{75}$, (C=J)O, OC=J or

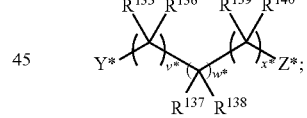

J, J* and J** is oxygen or sulfur;

Y* is $NR^{141}$, O, S, $SO_2$, $SO_3$, C=J*, $NR^{142}C=J*$, $C(=J*)NR^{143}$, $NR^{144}C(=J*)NR^{145}$, (C=J*)O or OC=J*;

Z* is $NR^{146}$, O, S, $SO_2$, $SO_3$, C=J, $NR^{147}C=J$, $C(=J)NR^{148}$, $NR^{149}C(=J)NR^{150}$, (C=J)O, OC=J or g, h, i, j, k, l, v*, w* and x* are each independently an integer between 0 and 5, provided that at least one of g, h, I, j, k, l, v*, w* and x* is not 0;

$R^{59}$ and $R^{60}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{59}$ and $R^{60}$ are absent when g is 0;

$R^{61}$ and $R^{62}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{61}$ and $R^{62}$ are absent when h is 0;

$R^{63}$ and $R^{64}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{63}$ and $R^{64}$ are absent when i is 0;

$R^{65}$ and $R^{66}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{65}$ and $R^{66}$ are absent when j is 0;

$R^{67}$ and $R^{68}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{67}$ and $R^{68}$ are absent when k is 0;

$R^{69}$ and $R^{70}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{69}$ and $R^{70}$ are absent when l is 0;

$R^{135}$ and $R^{136}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{135}$ and $R^{136}$ are absent when v* is 0;

$R^{137}$ and $R^{138}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{137}$ and $R^{138}$ are absent when w* is 0;

$R^{139}$ and $R^{140}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{139}$ and $R^{140}$ are absent when x* is 0; or $R^{59}$ and $R^{60}$ or $R^{60}$ and $R^{61}$ or $R^{61}$ and $R^{62}$ or $R^{62}$ and $R^{63}$ or $R^{63}$ and $R^{64}$ or $R^{64}$ and $R^{65}$ or $R^{65}$ and $R^{66}$ or $R^{66}$ and $R^{67}$ or $R^{67}$ and $R^{68}$ or $R^{68}$ and $R^{69}$ or $R^{69}$ and $R^{70}$ or $R^{135}$ and $R^{136}$ or $R^{136}$ and $R^{137}$ or $R^{137}$ and $R^{138}$ or $R^{138}$ and $R^{139}$ or $R^{139}$ and $R^{140}$, together with the carbon atoms to which they are attached are linked to form a 3 to 10-membered carbocyclic or heterocyclic ring;

$R^{71}$, $R^{72}$, $R^{73}$, $R^{74}$, $R^{75}$, $R^{141}$, $R^{142}$, $R^{143}$, $R^{144}$, $R^{145}$, $R^{146}$ $R^{147}$, $R^{148}$, $R^{149}$ and $R^{150}$ are each independently hydrogen, hydroxy, alkoxy, alkyl, alkenyl, alkynyl, aryl, carbonyl, carboxy, acyl or $NR^{76}R^{77}$; and $R^{76}$ and $R^{77}$ are each independently hydrogen, alkyl, alkenyl, alkynyl, aryl, a heterocyclic moiety or carbonyl.

The language, "color fastness moiety" includes chemical groups that enable the dye to resist color change, e.g., a chemical group that enhances the retention and/or stability of the dye on/in the substance to which it is applied.

In one embodiment, the color fastness moiety is of formula V:

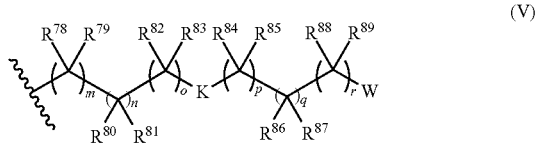

(V)

wherein

K is $NR^{90}$, O, S, $SO_2$, $SO_3$, C=M, $NR^{91}$C=M, C(=M)$NR^{92}$, $NR^{93}$C(=M)$NR^{94}$ or (C=M)O, OC=M when the dye is of formula Ia; or K is NL*, NL*C=M, C(=M)NL*, NL*C(=M)$NR^{94}$ or $NR^{93}$C(=M)NL* when the dye is of formula Ib;

W is $NR^{95}R^{96}$, $CR^{97}R^{98}R^{99}$, $OR^{100}$, $SR^{101}$ or halogen,

M is oxygen or sulfur m, n, o, p, q and r are independently an integer between 0 and 5, provided at least one of m, n, o, p, q, and r is not 0;

$R^{78}$ and $R^{79}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{78}$ and $R^{79}$ are absent when m is 0;

$R^{80}$ and $R^{81}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{80}$ and $R^{81}$ are absent when n is 0;

$R^{82}$ and $R^{83}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{82}$ and $R^{83}$ are absent when o is 0;

$R^{84}$ and $R^{85}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{84}$ and $R^{85}$ are absent when p is 0;

$R^{86}$ and $R^{87}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{86}$ and $R^{87}$ are absent when q is 0;

$R^{88}$ and $R^{89}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{88}$ and $R^{89}$ are absent when r is 0; or $R^{78}$ and $R^{79}$ or $R^{79}$ and $R^{80}$ or $R^{80}$ and $R^{81}$ or $R^{81}$ and $R^{82}$ or $R^{82}$ and $R^{83}$ or $R^{83}$ and $R^{84}$ or $R^{84}$ and $R^{85}$ or $R^{85}$ and $R^{86}$ or $R^{86}$ and $R^{87}$ or $R^{87}$ and $R^{88}$ or $R^{88}$ and $R^{89}$, together with the carbon atoms to which they are attached are linked to form a 3 to 10-membered carbocyclic or heterocyclic ring;

$R^{90}$, $R^{91}$, $R^{92}$, $R^{93}$ and $R^{94}$ are each independently hydrogen, hydroxy, alkoxy, alkyl, alkenyl, alkynyl, aryl, carbonyl, carboxy or acyl;

$R^{95}$ and $R^{96}$ are each independently hydrogen, hydroxy, alkoxy, alkyl, alkenyl, alkynyl, aryl, carbonyl, carboxy, acyl or $NR^{102}R^{103}$, or $R^{95}$ and $R^{96}$ together with the nitrogen to which they are attached are linked to form a 3-10 membered aliphatic, heterocyclic or aromatic ring;

$R^{97}$, $R^{98}$ and $R^{99}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{97}$ and $R^{98}$ together with the carbon to which they are attached are linked to form a 3-10 membered carbocyclic or heterocyclic ring; or $R^{99}$ is absent and $R^{97}$ and $R^{98}$ together with the carbon to which they are attached are linked to form a 4 to 10 membered aromatic ring;

$R^{100}$ and $R^{101}$ are each independently hydrogen, alkyl, alkenyl, alkynyl, aryl, carbonyl, acyl or a heterocyclic moiety; and $R^{102}$ and $R^{103}$ are each independently hydrogen, hydroxy, alkoxy, alkyl, alkenyl, alkynyl, aryl, carbonyl, carboxy or acyl, or $R^{102}$ and $R^{103}$ together with the nitrogen to which they are attached are linked to form a 3-10 membered aliphatic, heterocyclic or aromatic ring.

In some embodiments, color fastness moiety is of formula (Va):

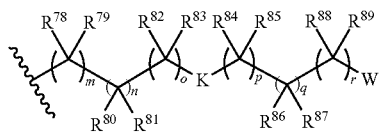

wherein m, n, o, p, q and r are each independently an integer from 0-2, provided that at least one of m, n, o, p. q and r is not 0;
$R^{78}$, $R^{79}$, $R^{80}$, $R^{81}$, $R^{82}$, $R^{83}$, $R^{84}$, $R^{85}$, $R^{86}$, $R^{87}$, $R^{88}$ and $R^{89}$ are each independently hydrogen or absent;
$R^{86}$ is absent, hydrogen or hydroxyl;
K is $NR^{90}$, C(=O)$NR^{92}$ or OC=O;
W is $NR^{95}R^{96}$, $CR^{97}R^{98}R^{99}$ or $OR^{100}$;
$R^{90}$ and $R^{92}$ are each independently hydrogen or alkyl;
$R^{95}$ is alkyl and $R^{96}$ is hydrogen or alkyl, or $R^{95}$ and $R^{96}$, together with the nitrogen to which they are attached are linked to form a 4-8-membered heterocyclic ring comprising 1-3 heteroatoms;
$R^{97}$, $R^{98}$ and $R^{99}$ are hydrogen, alkyl, alkoxy or heteroaryl; and
$R^{100}$ is hydrogen or alkyl,
provided that when m, n, o and p are 0; q and r are 1, $R^{86}$, $R^{87}$, $R^{88}$ and $R^{89}$ are each hydrogen; W is $OR^{100}$, K is $NR^{90}$ and $R^{100}$ is hydrogen, then $R^{90}$ is not methyl.

In some embodiments, m, n and o are 0.
In some embodiments, p, q and r are each 1.
In some embodiments, $R^{84}$, $R^{85}$, $R^{86}$, $R^{87}$; $R^{88}$ and $R^{89}$ are each hydrogen.
In some embodiments, K is $NR^{90}$.
In some embodiments, $R^{90}$ is hydrogen.
In some embodiments, W is $NR^{95}NR^{96}$, and $R^{95}$ and $R^{96}$ are each alkyl.

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c, d and e are each 0; E is $NR^{52}$; $R^{52}$ is alkyl (e.g., ethyl); f is 1; $R^{50}$ and $R^{51}$ are each hydrogen; m, n and o are each 0; K is C(=M)$NR^{92}$; M is oxygen; p, q and r are each 1; $R^{84}$, $R^{85}$, $R^{86}$, $R^{87}$, $R^{88}$, $R^{89}$ and $R^{92}$ are each hydrogen; W is $NR^{95}R^{96}$; $R^{95}$ and $R^{96}$ are each alkyl (e.g., substituted or unsubstituted alkyl, for example, ethyl or hydroxyl substituted alkyl, such as hydroxyethyl).

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c, d and e are each 0; E is $NR^{52}$; $R^{52}$ is alkyl (e.g., ethyl); f is 1; $R^{50}$ and $R^{51}$ are each hydrogen; m, n and o are each 0; K is C(=M)$NR^{92}$; M is oxygen; p, q and r are each 1; $R^{84}$, $R^{85}$, $R^{86}$, $R^{87}$, $R^{88}$, $R^{89}$ and $R^{92}$ are each hydrogen; W is $NR^{95}R^{96}$; $R^{95}$ and $R^{96}$ are linked to form a ring (e.g., a 6-membered heterocyclic ring, for example, a morpholinyl ring).

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c, d and e are each 0; E is $NR^{52}$; $R^{52}$ is alkyl (e.g., ethyl); f is 1; $R^{50}$ and $R^{51}$ are each hydrogen; m, n and o are each 0; K is C(=M)$NR^{92}$; M is oxygen; p, q and r are each 1; $R^{84}$, $R^{85}$, $R^{86}$, $R^{87}$, $R^{88}$, $R^{89}$ and $R^{92}$ are each hydrogen; W is $CR^{97}R^{98}R^{99}$; $R^{97}$ is hydrogen and $R^{98}$ and $R^{99}$ are each alkoxy (e.g., ethoxy).

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c, d and e are each 0; E is $NR^{52}$; $R^{52}$ is alkyl (e.g., ethyl); f is 1; $R^{50}$ and $R^{51}$ are each hydrogen; m, n and o are each 0; K is C(=M)$NR^{92}$; M is oxygen; p, q and r are each 1; $R^{84}$, $R^{85}$, $R^{87}$, $R^{88}$, $R^{89}$ and $R^{92}$ are each hydrogen; $R^{86}$ is hydroxyl; W is $OR^{100}$ and $R^{100}$ is hydrogen.

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c and d are each 0; E is

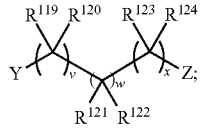

Y is $NR^{125}$, $R^{125}$ is alkyl (e.g., ethyl); v and w are each 1; x is 0; $R^{119}$, $R^{120}$, $R^{121}$ and $R^{122}$ are each hydrogen; Z is OC=$A^{}$; $A^{}$ is oxygen; e and f are each 1; $R^{48}$, $R^{49}$, $R^{50}$ and $R^{51}$ are each hydrogen; m, n and o are each 0; K is $NR^{90}$; p, q and r are each 1; $R^{84}$, $R^{85}$, $R^{86}$, $R^{87}$, $R^{88}$, $R^{89}$ and $R^{90}$ are each hydrogen; W is $NR^{95}R^{96}$; $R^{95}$ and $R^{96}$ are each alkyl (e.g., substituted or unsubstituted alkyl, for example ethyl or hydroxyl substituted alkyl, such as hydroxyethyl).

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c and d are each 0; E is

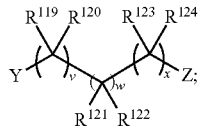

Y is $NR^{125}$, $R^{125}$ is alkyl (e.g., ethyl); v and w are each 1; x is 0; $R^{119}$, $R^{120}$, $R^{121}$ and $R^{122}$ are each hydrogen; Z is OC=$A^{}$; $A^{}$ is oxygen; e and f are each 1; $R^{48}$, $R^{49}$, $R^{50}$ and $R^{51}$ are each hydrogen; m, n and o are each 0; K is $NR^{90}$; p, q and r are each 1; $R^{84}$, $R^{85}$, $R^{87}$, $R^{88}$, $R^{89}$ and $R^{90}$ are each hydrogen; $R^{86}$ is hydroxyl; W is $OR^{100}$; and $R^{100}$ is hydrogen.

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c and d are each 0; E is

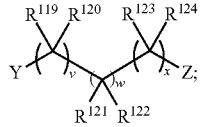

Y is $NR^{125}$, $R^{125}$ is alkyl (e.g., ethyl); v and w are each 1; x is 0; $R^{119}$, $R^{120}$, $R^{121}$ and $R^{122}$ are each hydrogen; Z is OC=A; A is oxygen; e and f are each 1; $R^{48}$, $R^{49}$, $R^{50}$ and $R^{51}$ are each hydrogen; m, n and o are each 0; K is $NR^{90}$; p is 1; q is 1; r is 0; $R^{84}$, $R^{85}$, $R^{86}$, $R^{87}$ and $R^{90}$ are each hydrogen; W is $NR^{95}R^{96}$; $R^{95}$ and $R^{96}$ are each hydrogen.

In one embodiment, the dye is of formula Ia, and C is an azo dye. In yet another embodiment, C is of formula IIg; $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine) and $R^{7c}$ is attached to L; a, b, c and d are each 0; E is

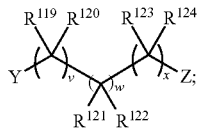

Y is $NR^{125}$, $R^{125}$ is alkyl (e.g., ethyl); v and w are each 1; x is 0; $R^{119}$, $R^{120}$, $R^{121}$ and $R^{122}$ are each hydrogen; Z is OC=A; A is oxygen; e and f are each 1; $R^{48}$, $R^{49}$, $R^{50}$ and $R^{51}$ are each hydrogen; m, n and o are each 0; K is $NR^{90}$; p, q and r are each 1; $R^{84}$, $R^{85}$, $R^{86}$, $R^{87}$, $R^{88}$, $R^{89}$ and $R^{90}$ are each hydrogen; W is $CR^{97}R^{98}R^{99}$; $R^{97}$ is hydrogen and $R^{98}$ and $R^{99}$ are each alkoxy (e.g., ethoxy).

In one embodiment, the dye is of formula Ib in which C and C* are the same chromophore; C is of formula IIg, $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); $R^{7c}$ is attached to linker L; a, b and c are 0; E is

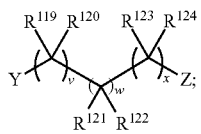

Y is $NR^{125}$; $R^{125}$ is alkyl (e.g., ethyl); v and w are each 1; x is 0; $R^{119}$, $R^{120}$, $R^{121}$ and $R^{122}$ are each hydrogen; Z is oxygen; d, e and f are each 1; $R^{46}$, $R^{47}$, $R^{48}$, $R^{50}$ and $R^{51}$ are each hydrogen; $R^{49}$ is hydroxyl; m, n and o are each 0; K is NL*; g, h and i are each 1; $R^{59}$, $R^{60}$, $R^{61}$, $R^{63}$ and $R^{64}$ are each hydrogen; $R^{62}$ is hydroxyl; G is

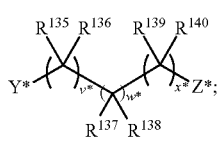

Y* is oxygen; v* is 1; w* is 1; x* is 0; $R^{135}$, $R^{136}$, $R^{137}$ and $R^{138}$ are each hydrogen; Z* is $NR^{146}$; $R^{146}$ is alkyl (e.g., ethyl); j, k and l are each 0; C* is of formula IIg in which $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); $R^{7c}$ is attached to linker L*; p, q and r are each 1; $R^{84}$, $R^{85}$, $R^{86}$, $R^{87}$, $R^{88}$ and $R^{89}$ are each hydrogen; W is $NR^{95}R^{96}$; and $R^{95}$ and $R^{96}$ are each alkyl (e.g., hydroxyl substituted alkyl, for example, hydroxyethyl).

In one embodiment, the dye is of formula Ib in which C and C* are the same chromophore; C is of formula IIg, $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); $R^{7c}$ is attached to linker L; a, b and c are 0; E is

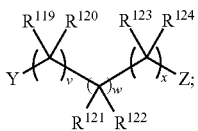

v is 1; w is 1; x is 0; $R^{119}$, $R^{120}$, $R^{121}$ and $R^{122}$ are each hydrogen; Y is $NR^{125}$; $R^{125}$ is alkyl (e.g., ethyl); Z is oxygen; d, e and f are each 1; $R^{46}$, $R^{47}$, $R^{48}$, $R^{50}$ and $R^{51}$ are each hydrogen; $R^{49}$ is hydroxyl; m, n and o are each 0; K is NL*; g, h and i are each 1; $R^{59}$, $R^{60}$, $R^{61}$, $R^{63}$ and $R^{64}$ are each hydrogen; $R^{62}$ is hydroxyl; G is

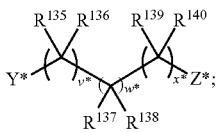

Y* is oxygen; v* is 1; w* is 1; x* is 0; $R^{135}$, $R^{136}$, $R^{137}$ and $R^{138}$ are each hydrogen; Z* is $NR^{146}$; $R^{146}$ is alkyl (e.g., ethyl); j, k and l are each 0; C* is of formula IIg in which $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); $R^{7c}$ is attached to linker L*; p, q and r are each 1; $R^{84}$, $R^{85}$, $R^{86}$, $R^{88}$ and $R^{89}$ are each hydrogen; $R^{87}$ is hydroxyl; W is $OR^{100}$ and $R^{100}$ is hydrogen.

In one embodiment, the dye is of formula Ib in which C and C* are the same chromophore; C is of formula IIg, $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); $R^{7c}$ is attached to linker L; a, b, c and d are 0; E is

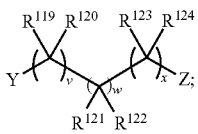

v is 1; w is 1; x is 0; $R^{119}$, $R^{120}$, $R^{121}$ and $R^{122}$ are each hydrogen; Y is $NR^{125}$; $R^{125}$ is alkyl (e.g., ethyl); Z is OC=A; A is oxygen; e and f are each 1; $R^{48}$, $R^{49}$, $R^{50}$ and $R^{51}$ are each hydrogen; m, n and o are each 0; K is NL*; g, and h are each 1; i is 0; $R^{59}$, $R^{60}$, $R^{61}$ and $R^{62}$, are each hydrogen; G is

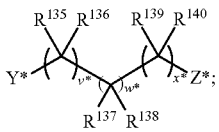

Y* is (C=J*)O; J* is oxygen; v* is 1; w* is 1; x* is 0; $R^{135}$, $R^{136}$, $R^{137}$ and $R^{138}$ are each hydrogen; Z* is $NR^{146}$; $R^{146}$ is alkyl (e.g., ethyl); j, k and l are each 0; C* is of formula IIg in which $R^{7a}$, $R^{7b}$, $R^{7d}$, $R^{7e}$, $R^{7f}$, $R^{7g}$ and $R^{7i}$ are each hydrogen; $R^{7h}$ is —$NO_2$; $R^{7j}$ is halogen (e.g., chlorine); le is attached to linker L*; p, q and r are each 1; $R^{84}$, $R^{85}$, $R^{86}$, $R^{87}$, $R^{88}$ and $R^{89}$ are each hydrogen; W is $NR^{95}R^{96}$; and $R^{95}$ and $R^{96}$ are each alkyl (e.g., ethyl or hydroxyethyl).

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each 0; K is $NR^{90}$; p, is 0; q and r are each 1; $R^{87}$, $R^{88}$, $R^{89}$ and $R^{90}$ are each hydrogen; W is $OR^{100}$; $R^{100}$ is hydrogen; and $R^{86}$ is alkyl (e.g., hydroxymethyl).

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each 0; K is $NR^{90}$; p is 1; q is 1; r is 0; $R^{84}$, $R^{85}$, $R^{86}$, $R^{87}$ and $R^{90}$ are each hydrogen; W is $NR^{95}R^{96}$; $R^{95}$ and $R^{96}$ are each hydrogen or alkyl (e.g., hydroxyethyl).

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each 0; K is $NR^{90}$; p, q and r are each 1; $R^{84}$, $R^{85}$, $R^{87}$, $R^{88}$, $R^{89}$ and $R^{90}$ are hydrogen; $R^{86}$ is hydroxyl; W is $OR^{100}$ and $R^{100}$ is hydrogen.

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each 0; K is $NR^{90}$; p, q and r are each 1; $R^{84}$, $R^{85}$, $R^{86}$, $R^{87}$, $R^{88}$, $R^{89}$ and $R^{90}$ are each hydrogen; W is $NR^{95}R^{96}$; $R^{95}$ and $R^{96}$ are each alkyl (e.g., ethyl or hydroxyethyl).

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each each 0; K is $NR^{90}$; p, q and r are each 1; $R^{84}$, $R^{85}$, $R^{86}$, $R^{87}$, $R^{88}$, $R^{89}$ and $R^{90}$ are each hydrogen; W is $CR^{97}R^{98}R^{99}$; $R^{97}$ is hydrogen; $R^{98}$ and $R^{99}$ are each alkoxy (e.g., ethoxy).

In one embodiment, the dye is of formula Ia; C is of formula IIz; $R^{26b}$, $R^{26e}$ and $R^{26f}$ are each hydrogen; $R^{26d}$ is amino (e.g., arylamino, for example, phenylamino); $R^{26c}$ is $NO_2$; $R^{26a}$ is attached to linker L; a, b, c, and d are each 0; E is $NR^{53}C=A$; A is oxygen; e and f are each 1; $R^{48}$, $R^{49}$, $R^{50}$, $R^{51}$ and $R^{53}$ are each hydrogen; m, n and o are each 0; K is $NR^{90}$; p, q and r are each 1; $R^{84}$, $R^{85}$, $R^{86}$, $R^{87}$, $R^{88}$, $R^{89}$ and $R^{90}$ are each hydrogen; W is $CR^{97}R^{98}R^{99}$; $R^{97}$ and $R^{98}$ are each hydrogen; $R^{99}$ is alkyl (e.g., n-butyl).

In some embodiments, C is of formula Hz; $R^{26a}$ is attached to linker L; $R^{26b}$ is $-NO_2$; $R^{26c}$, $R^{26d}$, $R^{26e}$ and $R^{26f}$ are hydrogen; a, b, c and d are each 0; E is $NR^{52}$; e and f are each 1; $R^{48}$, $R^{49}$, $R^{50}$, $R^{51}$ and $R^{52}$ are each hydrogen; m, n and o are 0; K is $NR^{90}$; p, q and r are each 1; W is $NR^{95}R^{96}$; $R^{95}$ and $R^{96}$ are each alkyl (e.g., methyl, ethyl or hydroxyethyl); and $R^{84}$, $R^{85}$, $R^{86}$, $R^{87}$, $R^{88}$, $R^{89}$ and $R^{90}$ are each hydrogen.

In some embodiments, C is of formula Hz, $R^{26a}$ is attached to linker L; $R^{26b}$ is $-NO_2$; $R^{26c}$, $R^{26e}$ and $R^{26f}$ are hydrogen; $R^{26d}$ is $-NH_2$; a, b, c and d are each 0; E is $NR^{52}$; e and f are each 1; $R^{48}$, $R^{49}$, $R^{50}$, $R^{51}$ and $R^{52}$ are each hydrogen; m, n and o are 0; K is $NR^{90}$; p, q and r are each 1; W is $NR^{95}R^{96}$; $R^{95}$ and $R^{96}$ are each alkyl (e.g., methyl, ethyl or hydroxyethyl); and $R^{84}$, $R^{85}$, $R^{86}$, $R^{87}$, $R^{88}$, $R^{89}$ and $R^{90}$ are each hydrogen.

In some embodiments, C is of formula Hz; $R^{26a}$ is attached to linker L; $R^{26b}$ is $-NO_2$; $R^{26c}$, $R^{26d}$, $R^{26e}$ and $R^{26f}$ are hydrogen; a, b, c and d are each 0; E is $NR^{52}$; e and f are each 1; $R^{48}$, $R^{49}$, $R^{50}$, $R^{51}$ and $R^{52}$ are each hydrogen; m, n and o are 0; K is $NR^{90}$; p, q and r are each 1; W is $NR^{95}R^{96}$; $R^{95}$ and $R^{96}$ are linked to form a 6-membered heterocyclic ring (e.g., a piperidine or morpholine ring); and $R^{84}$, $R^{85}$, $R^{86}$, $R^{87}$; $R^{88}$, $R^{89}$ and $R^{90}$ are each hydrogen.

In some embodiments, C is of formula Hz, $R^{26a}$ is attached to linker L; $R^{26b}$ is $-NO_2$; $R^{26c}$, $R^{26e}$ and $R^{26f}$ are hydrogen; $R^{26d}$ is $-NH_2$; a, b, c and d are each 0; E is $NR^{52}$; e and f are each 1; $R^{48}$, $R^{49}$, $R^{50}$, $R^{51}$ and $R^{52}$ are each hydrogen; m, n and o are 0; K is $NR^{90}$; p, q and r are each 1; W is $NR^{95}R^{96}$; $R^{95}$ and $R^{96}$ are linked to form a 6-membered heterocyclic ring (e.g., a piperidine or morpholine ring); and $R^{84}$, $R^{85}$, $R^{86}$, $R^{87}$; $R^{88}$, $R^{89}$ and $R^{90}$ are each hydrogen.

In some embodiments, the dye is a compound of formula X:

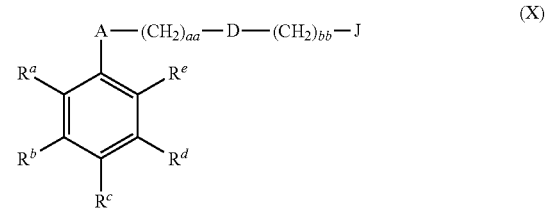

wherein
$R^a$, $R^b$, $R^c$, $R^d$ and $R^e$ are each independently hydrogen, hydroxy, amino, alkoxy, alkyl, $CF_3$, CN, halogen, $NO_2$, $CF_3$, $SO_3H$, CN, aminocarbonyl, carbonyl, alkoxycarbonyl or an aryldiazene moiety;
aa and bb are each an integer from 1-5;
A is O, S, CO, $NR^f$, $NR^fCO$ or $CONR^f$;
D is O, S, CO, O(CO), $NR^g$, $NR^gCO$ or $CONR^g$;
J is $OR^h$, $SR^h$ or $NR^hR^i$;
$R^f$, $R^g$, and $R^h$ are each independently hydrogen or alkyl;
$R^i$ is alkyl; or $R^h$ and $R^i$ are linked together with the atom to which they are attached form a 4-8 membered heterocyclic ring with 1-3 heteroatoms; and cosmetically acceptable salts thereof, and
provided that when A is $NR^f$; D is $NR^g$; J is $OR^h$; $R^a$, $R^b$, $R^e$, $R^f$ and $R^h$ are each hydrogen; $R^c$ is methylamino; $R^d$ is $-NO_2$; aa is 3 and bb is 2, then $R^g$ is not methyl.

In some embodiments, $R^a$ is $-NO_2$, $R^b$, $R^d$ and $R^e$ are each hydrogen; $R^c$ is amino (e.g., $-NH_2$); A is $NR^f$, $R^f$ is hydrogen, aa is 2, D is $NR^g$, $R^g$ is hydrogen; bb is 3; J is $NR^hR^i$ and $R^h$ and $R^i$ are each alkyl (e.g., ethyl).

In some embodiments, $R^a$ is $-NO_2$, $R^b$, $R^c$, $R^d$ and $R^e$ are each hydrogen; A is $NR^f$, $R^f$ is hydrogen, aa is 2, D is $NR^g$, $R^g$ is hydrogen; bb is 3; J is $NR^hR^i$ and $R^h$ and $R^i$ are each alkyl (e.g., ethyl or hydroxyethyl).

In some embodiments, the dye is of formula Xa:

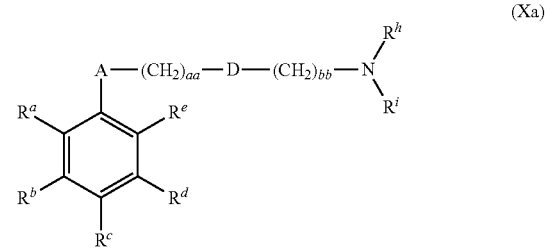

wherein $R^a$, $R^b$, $R^c$, $R^d$ and $R^e$ are each independently hydrogen, hydroxyl, amino, alkoxy, alkyl, $CF_3$, CN, halogen, $NO_2$, $CF_3$, $SO_3H$, CN, aminocarbonyl, carbonyl, alkoxycarbonyl or an aryldiazene moiety;

aa and bb are each an integer from 1-5;

A is $NR^f$ or $NR^fCO$;

D is O(CO), $NR^g$ or $CONR^g$;

$R^f$, $R^g$ and $R^h$ are each independently hydrogen or alkyl;

$R^i$ is alkyl; or $R^h$ and $R^i$ are linked together with the atom to which they are attached form a 4-8 membered heterocyclic ring with 1-3 heteroatoms; or a cosmetically acceptable salt thereof.

In some embodiments, $R^a$ is $-NO_2$.

In some embodiments, $R^b$, $R^d$ and $R^e$ are each hydrogen.

In some embodiments, $R^c$ is hydrogen or $NH_2$.

In some embodiments, A is $NR^f$.

In some embodiments, D is $NR^g$.

In some embodiments, $R^f$ and $R^g$ are each hydrogen.

In some embodiments, $R^h$ and $R^i$ are each alkyl (e.g., methyl, ethyl or hydroxyethyl).

In some embodiments, $R^h$ and $R^i$ are linked to form a 6-membered heterocyclic ring (e.g., a piperidine or morpholine ring).

In some embodiments, the dye is a compound of formula XI:

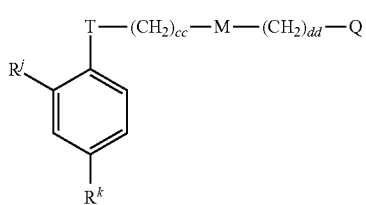

(XI)

$R^j$ and $R^k$ are each independently hydrogen, hydroxyl, amino, alkoxy, alkyl, $CF_3$, CN, halogen, $NO_2$, $CF_3$, $SO_3H$, CN, aminocarbonyl, carbonyl, alkoxycarbonyl or an aryldiazene moiety;

cc and dd are each an integer from 1-5;

T is O, S, CO, $NR^l$, $NR^lCO$ or $CONR^l$;

M is O, S, CO, OC(O), $NR^m$, $NR^mCO$ or $CONR^m$;

Q is $OR^n$, $SR^n$ or $NR^nR^o$;

$R^l$, $R^m$ and $R^n$ are each independently hydrogen or alkyl;

$R^o$ is alkyl; or $R^n$ and $R^o$ are linked together with the atom to which they are attached form a 4-8 membered heterocyclic ring with 1-3 heteroatoms; and cosmetically acceptable salts thereof.

In some embodiments, $R^j$ is $-NO_2$, $R^k$ is hydrogen; T is $NR^l$, $R^l$ is hydrogen; cc is 2; M is $NR^m$, $R^m$ is hydrogen; dd is 3; Q is $NR^nR^o$ and $R^n$ and $R^o$ are each alkyl (e.g., ethyl or hydroxyethyl).

In some embodiments, $R^j$ is $-NO_2$, $R^k$ is amino (e.g., $-NH_2$); T is $NR^l$, $R^l$ is hydrogen; cc is 2; M is $NR^m$, $R^m$ is hydrogen; dd is 3; Q is $NR^nR^o$ and $R^n$ and $R^o$ are each alkyl (e.g., ethyl).

In some embodiments, the dye is of formula XIa:

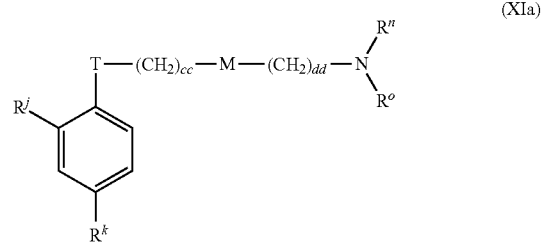

(XIa)

wherein $R^j$ and $R^k$ are each independently hydrogen, hydroxyl, amino, alkoxy, alkyl, CN, halogen, $NO_2$, $CF_3$, $SO_3H$, aminocarbonyl, carbonyl, alkoxycarbonyl or an aryldiazene moiety;

cc and dd are each an integer from 1-5;

T is $NR^l$ or $NR^lCO$;

M is $NR^m$ or $CONR^m$;

Q is $NR^nR^o$;

$R^l$, $R^m$ and $R^n$ are each independently hydrogen or alkyl;

$R^o$ is alkyl; or $R^n$ and $R^o$ are linked together with the atom to which they are attached form a 4-8 membered heterocyclic ring with 1-3 heteroatoms; and cosmetically acceptable salts thereof.

In some embodiments, T is $NR^l$.

In some embodiments, M is $NR^m$.

In some embodiments, $R^l$ and $R^m$ are each hydrogen.

In some embodiments, cc is 2 and dd is 3.

In some embodiments, $R^j$ is $NO_2$.

In some embodiments, $R^k$ is hydrogen or $NH_2$.

In some embodiments, $R^n$ and $R^o$ are each alkyl (e.g., methyl, ethyl or hydroxyethyl).

In some embodiments, $R^n$ and $R^o$ are linked to form a 6-membered heterocyclic ring (e.g., a piperidine or morpholine ring).

In some embodiments, the dye is a compound of formula XII:

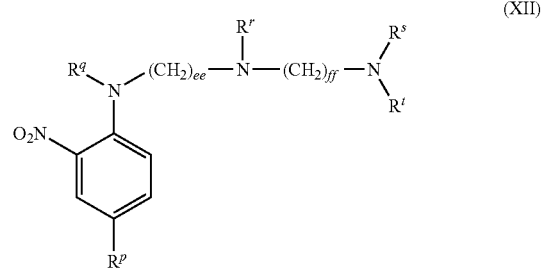

(XII)

wherein $R^p$ is hydrogen or amino;

$R^q$ and $R^r$ are each independently hydrogen or alkyl;

ee and ff are each independently an integer from 1-5; and $R^s$ and $R^t$ are each alkyl or together with the atom to which they are attached form a 4-8 membered heterocyclic ring with 1 or 2 heteroatoms, and cosmetically acceptable salts thereof.

In some embodiments, $R^p$ is amino (e.g., $-NH_2$); $R^q$ and $R^r$ are each hydrogen; ee is 2; ff is 3; and $R^s$ and $R^t$ are each alkyl (e.g., ethyl).

In some embodiments, $R^p$, $R^q$ and $R^r$ are each hydrogen; ee is 2; ff is 3; and $R^s$ and $R^t$ are each alkyl (e.g., ethyl or hydroxyethyl).

In some embodiments, $R^r$ is hydrogen.

In some embodiments, ee is 2.

In some embodiments, ff is 3.

In some embodiments, $R^s$ and $R^t$ are each alkyl (e.g., methyl, ethyl or hydroxyethyl).

In some embodiments, $R^s$ and $R^t$ are linked to form a 6-membered heterocyclic ring (e.g., piperidine or morpholine ring).

In some embodiments, $R^p$ is hydrogen.
In some embodiments, $R^p$ is $NH_2$.
In some embodiments, the dye is a compound of formula XIII:

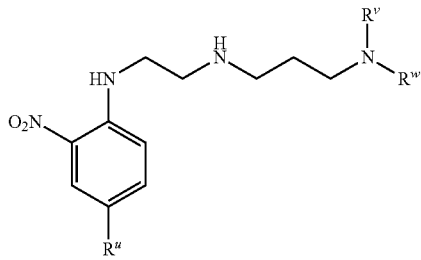

(XIII)

wherein
$R^u$ is hydrogen or $NH_2$ and
$R^v$ and $R^w$ are alkyl, and cosmetically acceptable salts thereof.

In some embodiments, $R^u$ is hydrogen and $R^v$ and $R^w$ are each ethyl. In some embodiments, $R^u$ is amino and $R^v$ and $R^w$ are each ethyl. In some embodiments, $R^u$ is hydrogen, $R^v$ and $R^w$ are methyl. In some embodiments, $R^u$ is $NH_2$, $R^v$ and $R^w$ are methyl. In some embodiments, $R^u$ is hydrogen, $R^v$ and $R^w$ are hydroxyethyl. In some embodiments, $R^u$ is $NH_2$, $R^v$ and $R^w$ are hydroxyethyl.

In some embodiments, the dye is selected from a compound in Table 2:

TABLE 2

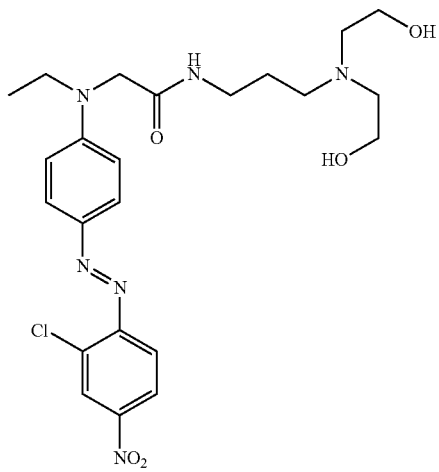

A

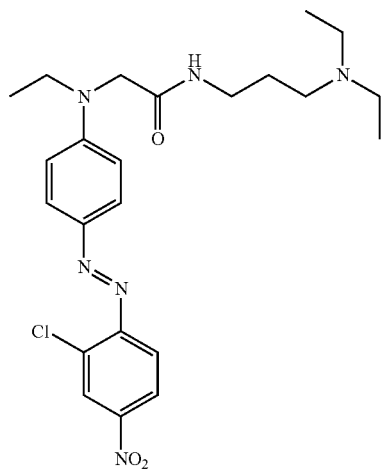

B

TABLE 2-continued
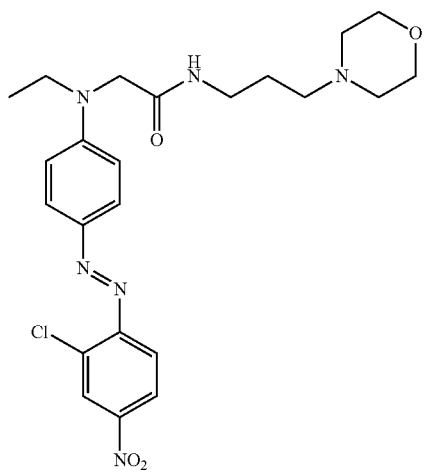
C
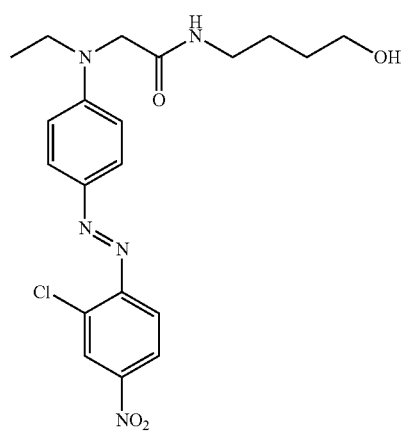
D
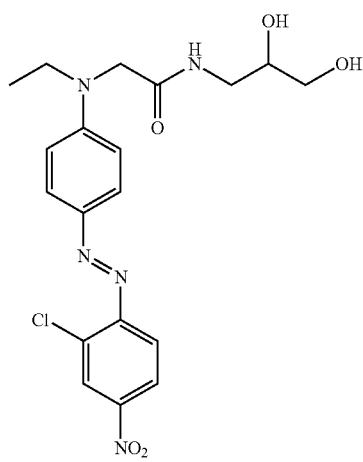
E

TABLE 2-continued
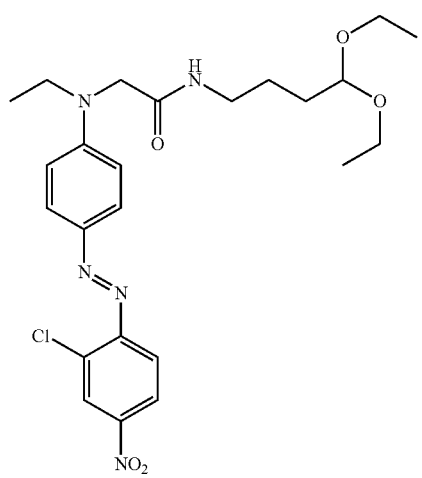
F
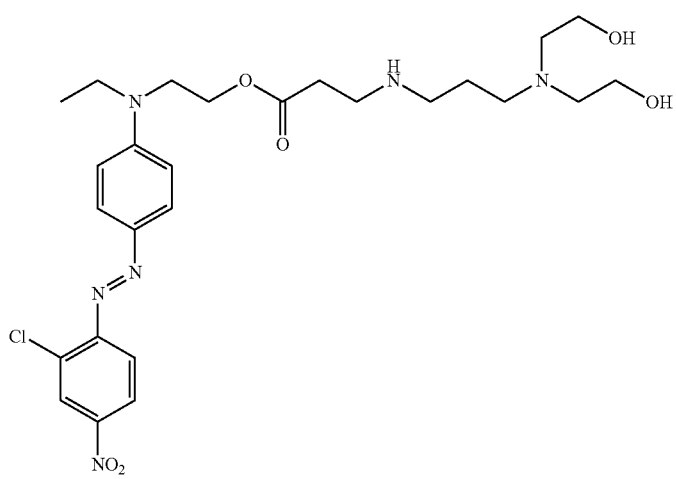
G
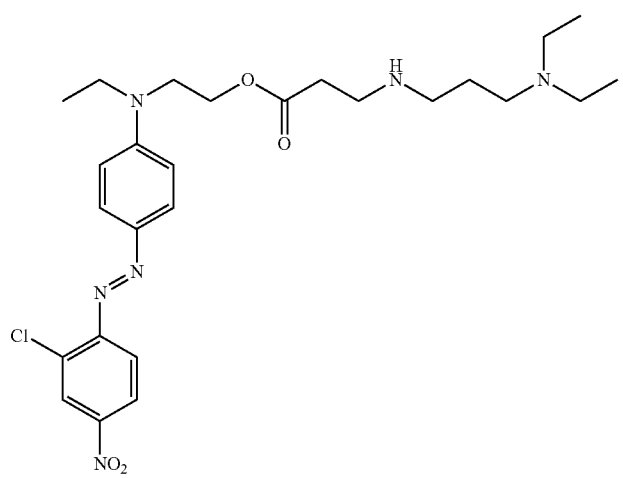
H

TABLE 2-continued
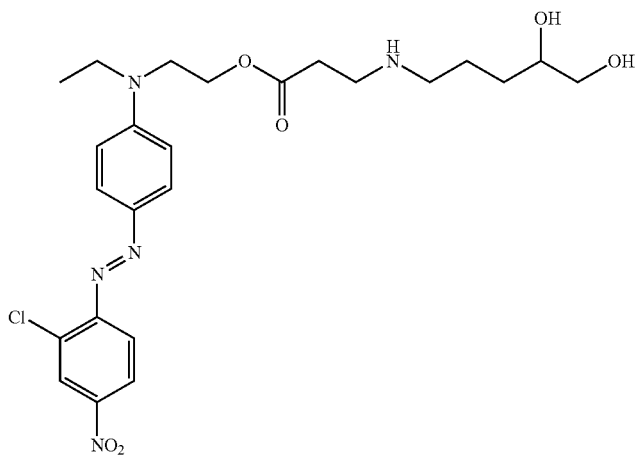
I
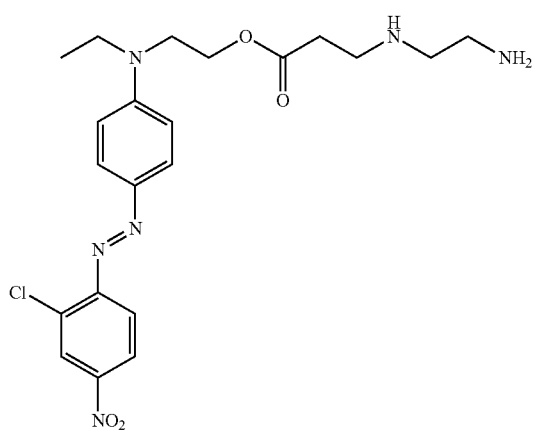
J
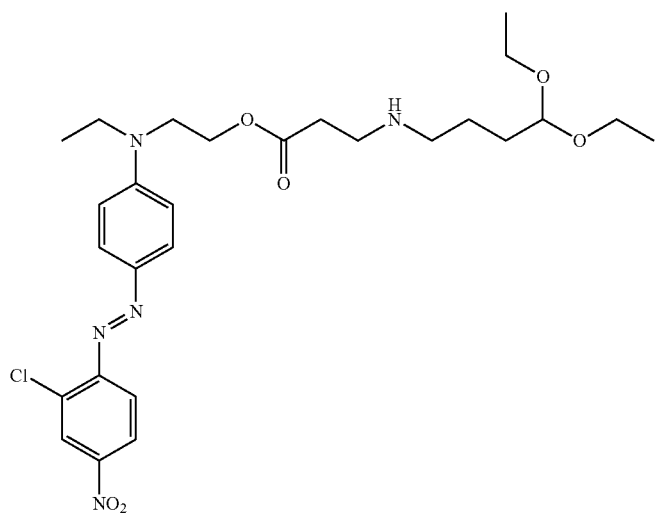
K

TABLE 2-continued
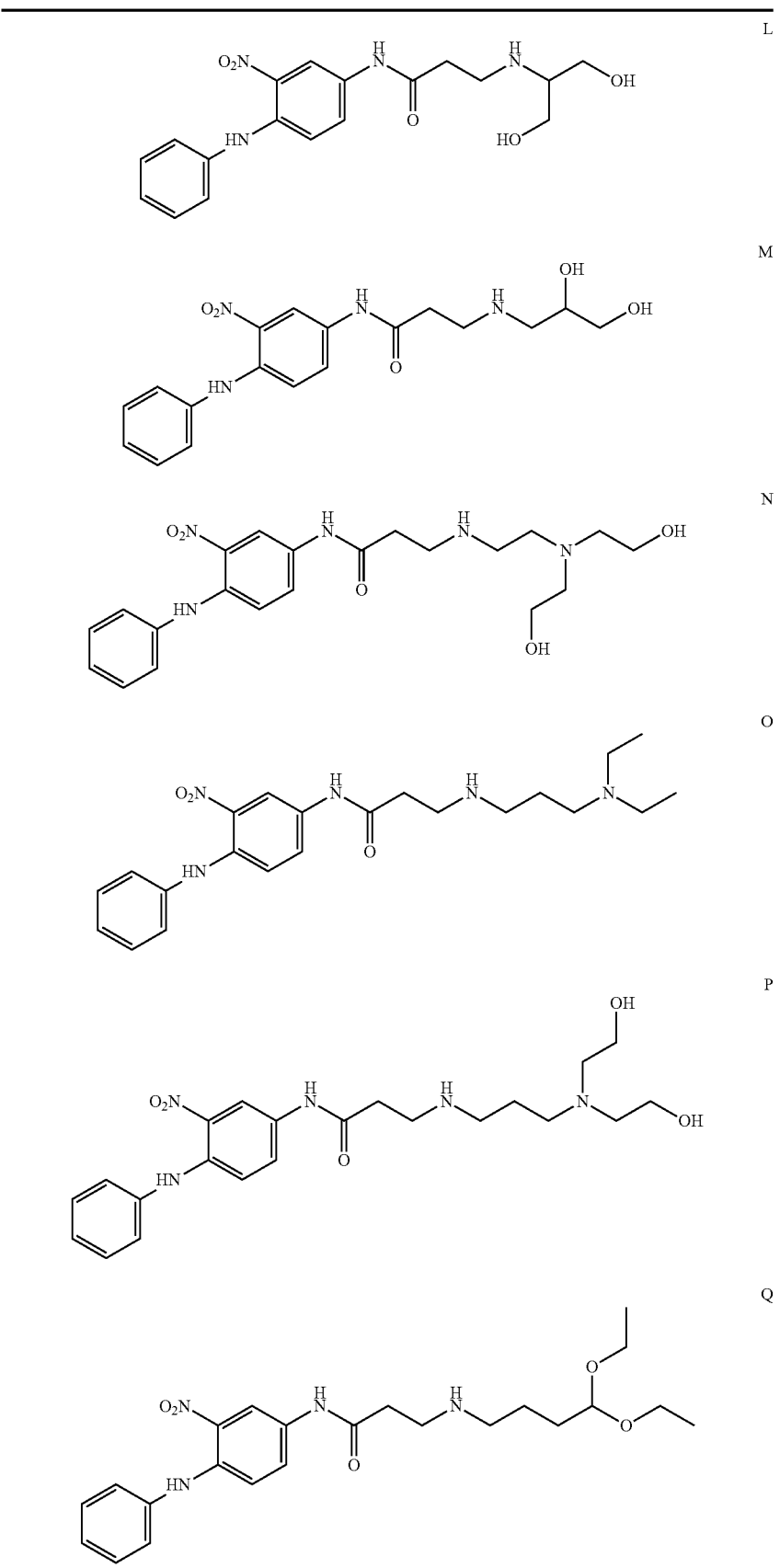

TABLE 2-continued
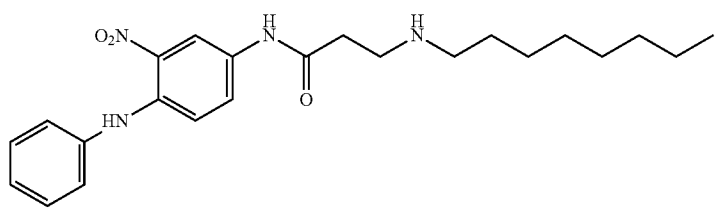
R
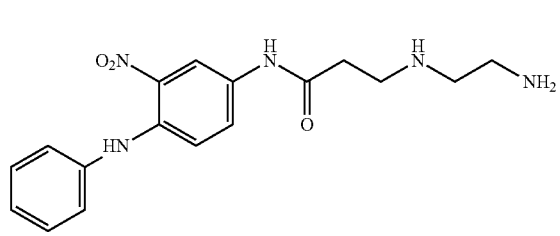
S
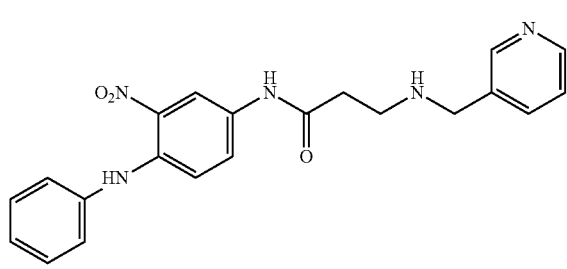
T
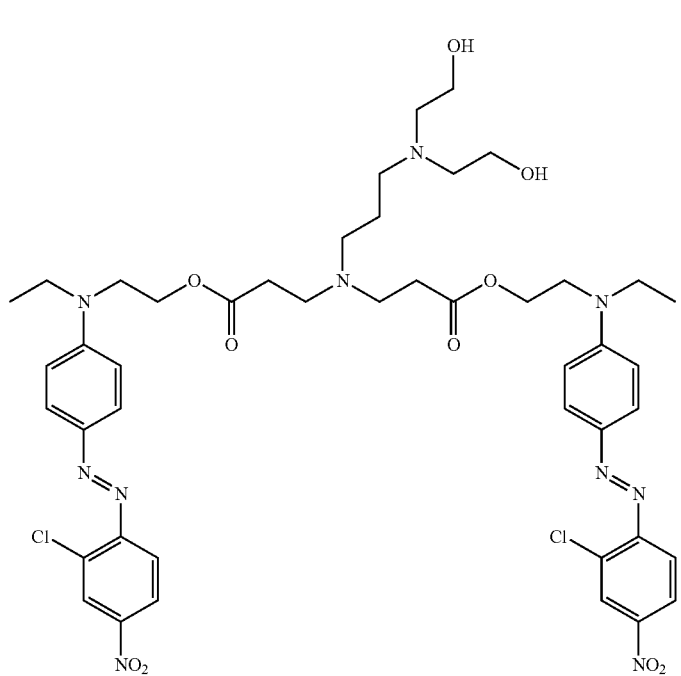
U

TABLE 2-continued
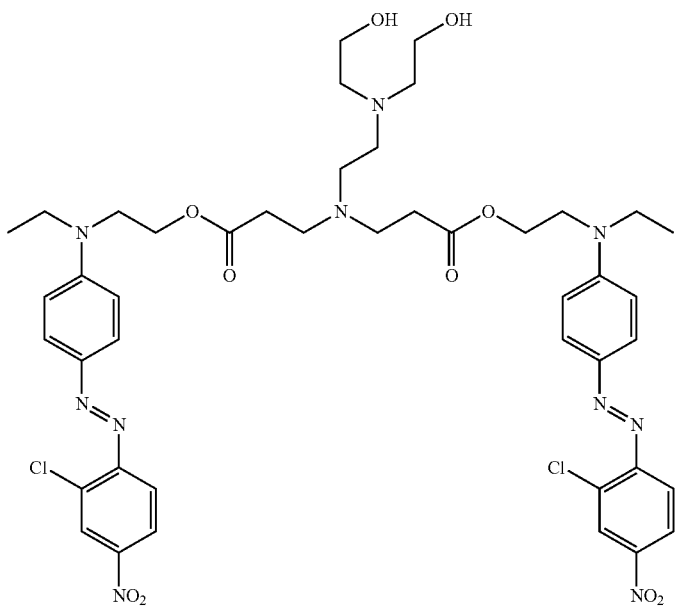
V
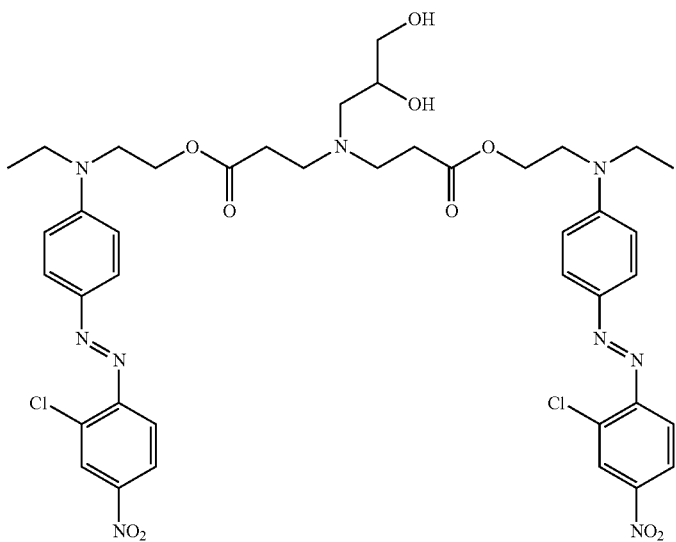
W

TABLE 2-continued
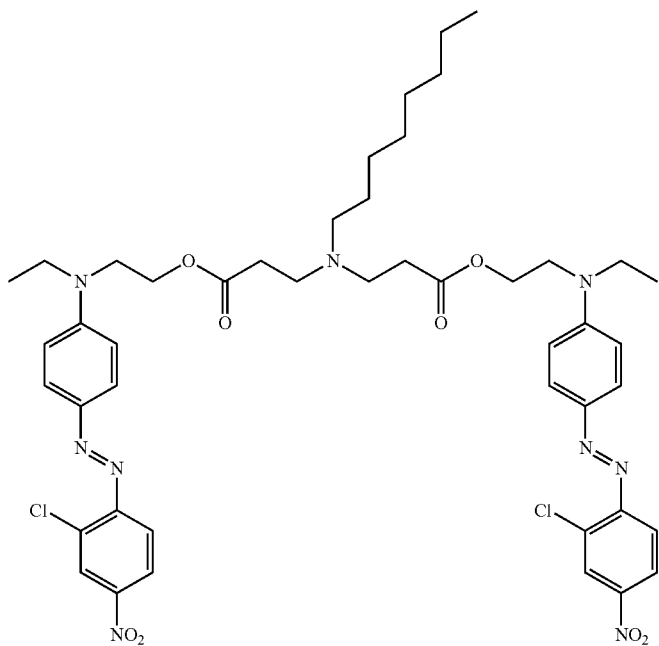
X
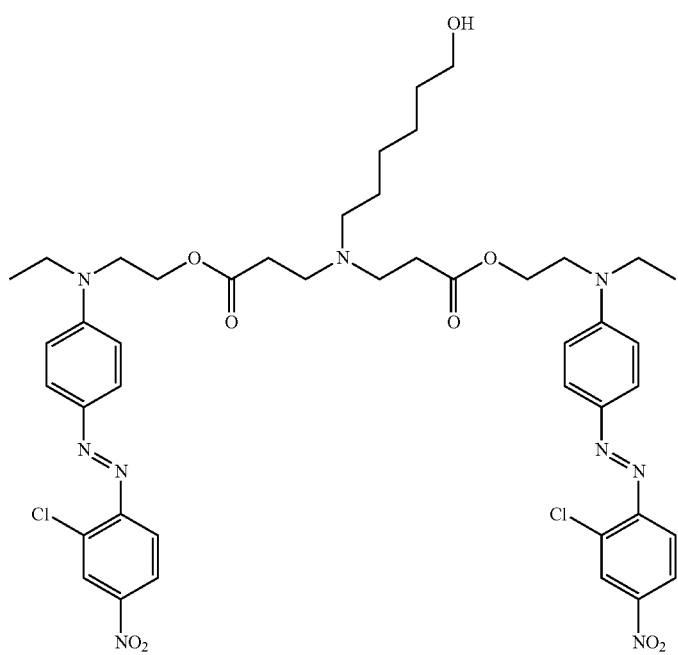
Y

TABLE 2-continued
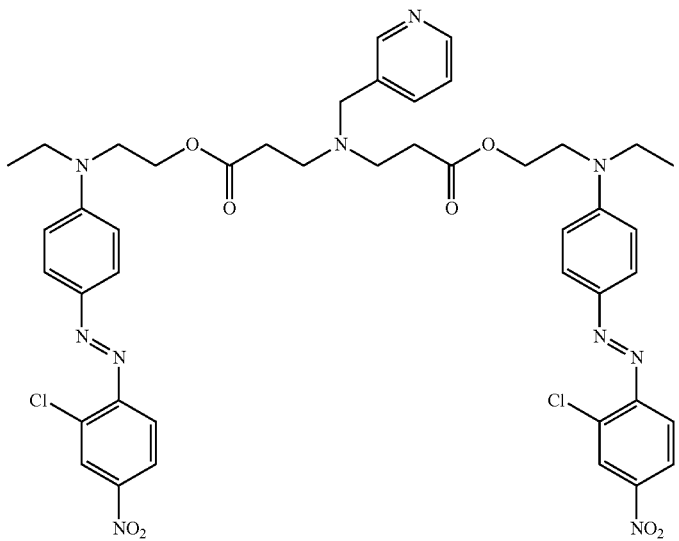
Z
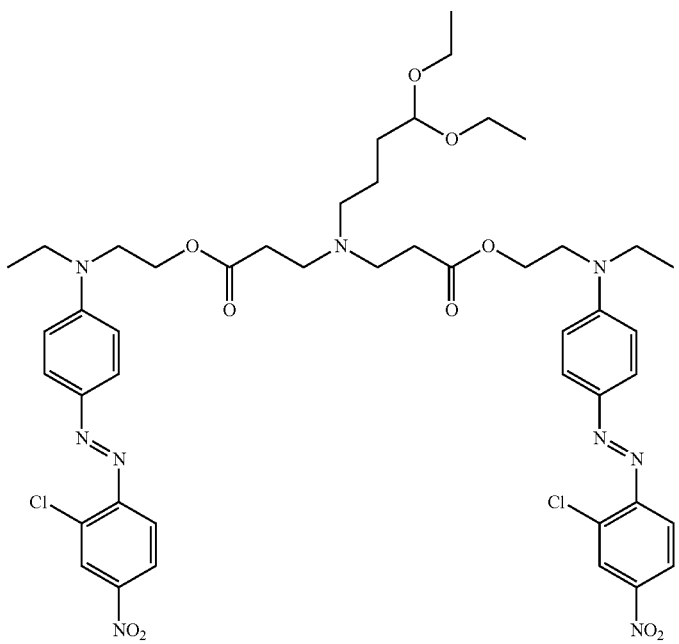
AA
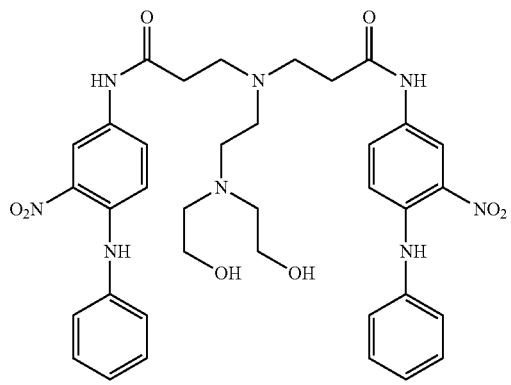
AB

TABLE 2-continued
AC
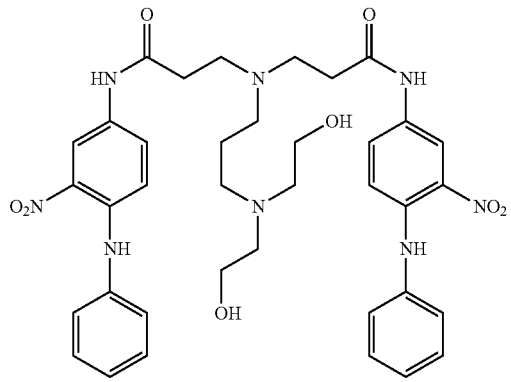
AD
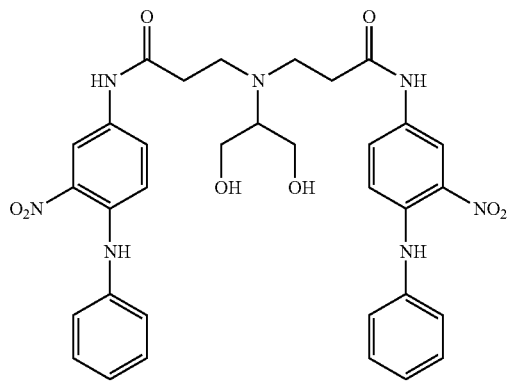
AE
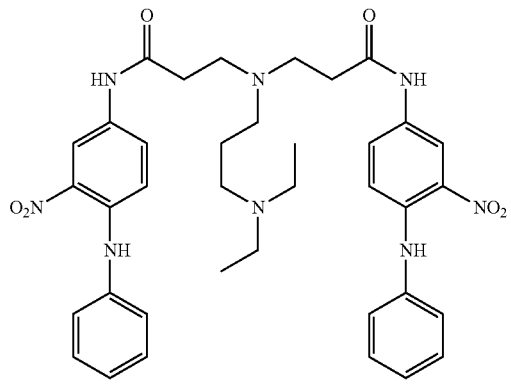
AF
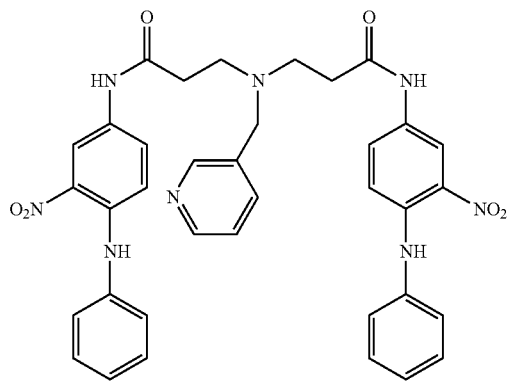

TABLE 2-continued
AG
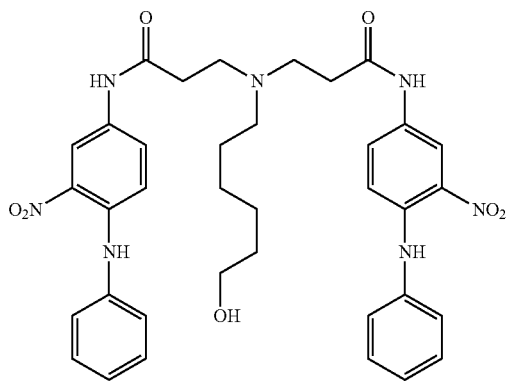
AH
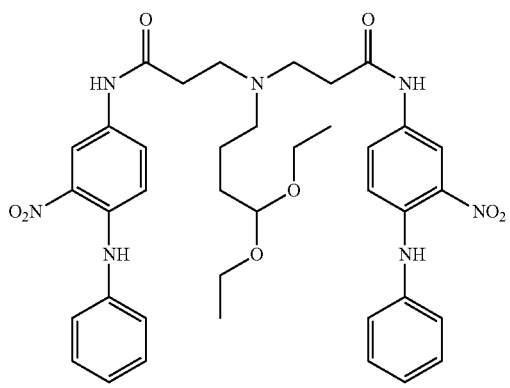
AI
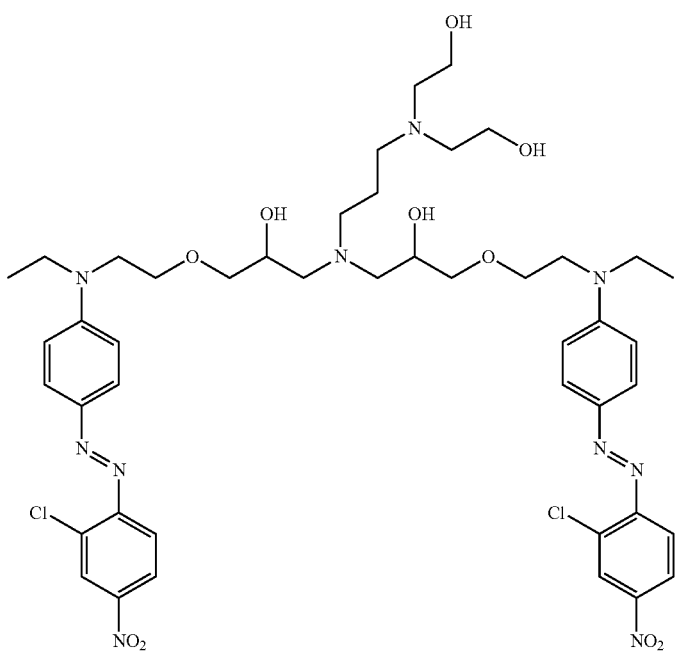

TABLE 2-continued
AJ
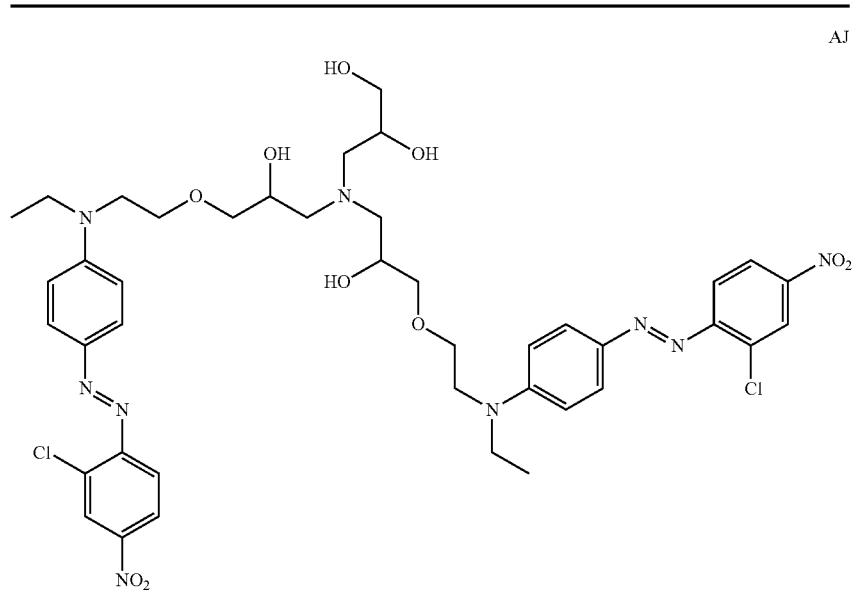
AK
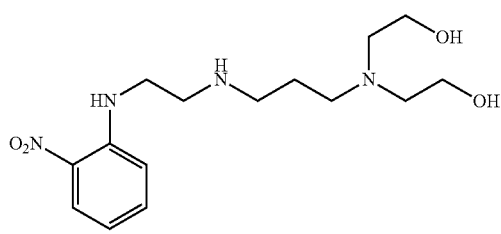
AL
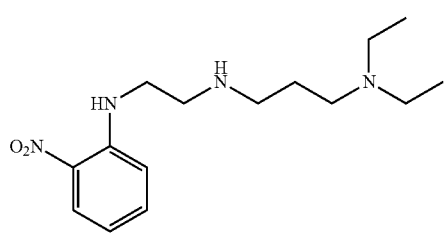
AM
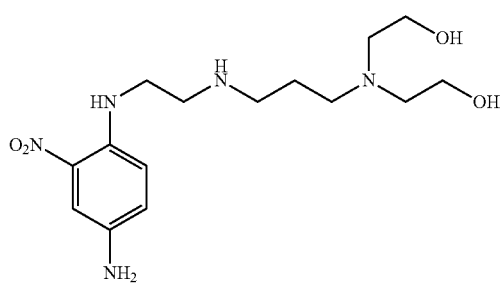

TABLE 2-continued
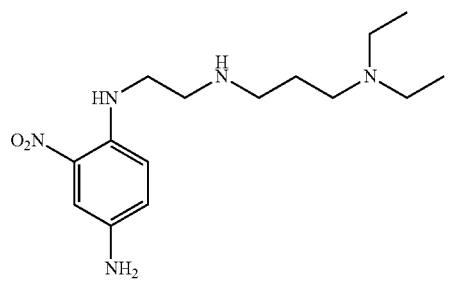 AN
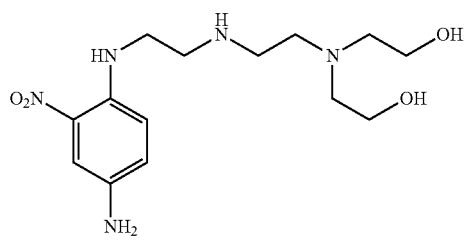 AO
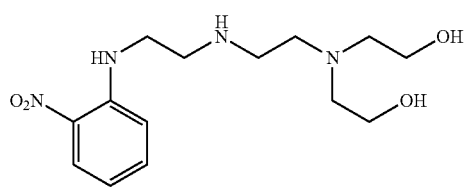 AP
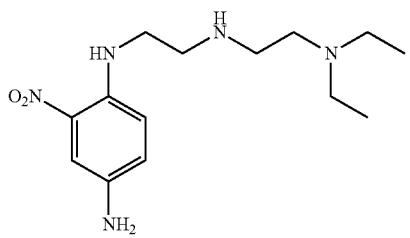 AQ
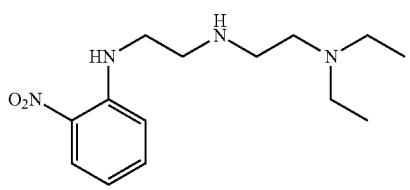 AR
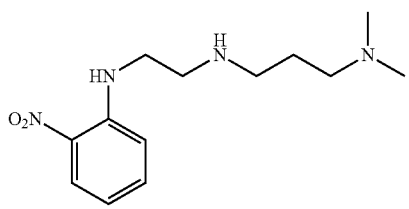 AS TABLE 2-continued
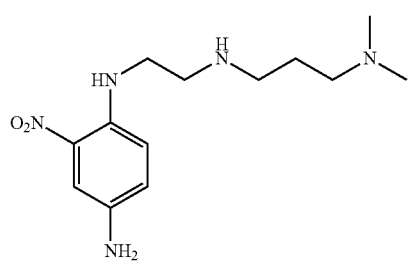
AT
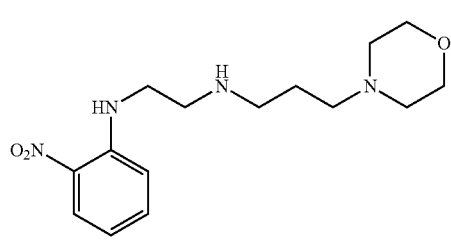
AU
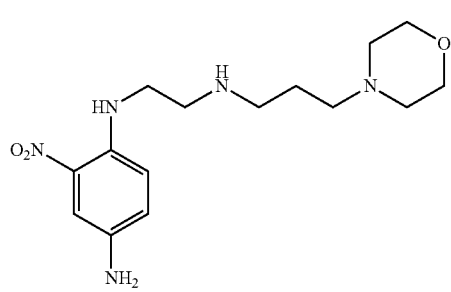
AV
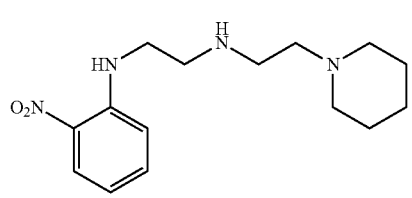
AW
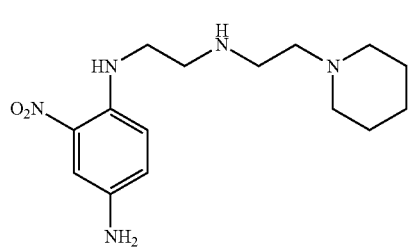
AX
or a cosmetically acceptable salt thereof.
In some embodiments, the dyes of the invention are not:
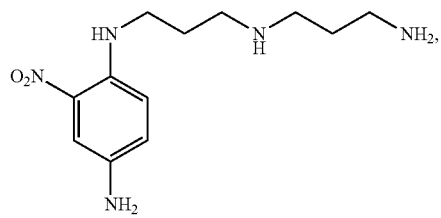
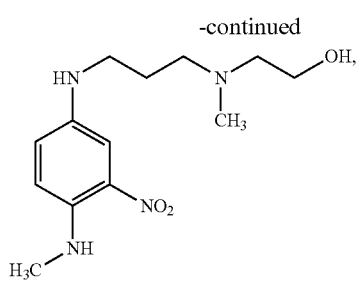
-continued

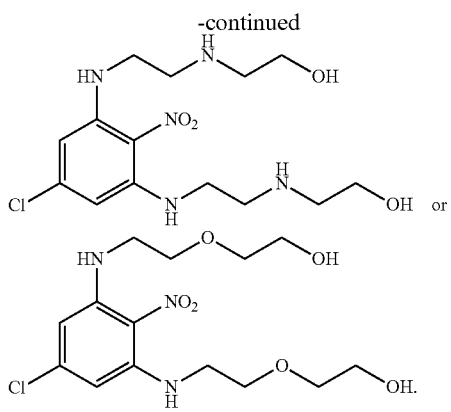

or

In some embodiments, the dyes of the invention are not those compounds disclosed in U.S. Pat. Nos. 2,750,326; 3,632,582; 3,665,036; 3,867,456; 3,904,690; 4,845,293; 4,797,129; French Patent No. 2870727; Netherland Laid Open Patent Application No. 6610759; and Great Britain Patent Publication Nos. 1150445; 1159557; 1164824 and 1164825.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclobutyl, cyclopentyl, cyclohexyl, cycloheptyl, cyclooctyl), alkyl substituted cycloalkyl groups, and cycloalkyl substituted alkyl groups. The term alkyl further includes alkyl groups that may include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain). Likewise, cycloalkyls may have from 3-8 carbon atoms in their ring structure. The term "$C_1$-$C_6$" includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkyl, alkenyl, alkynyl, halogen, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

In one embodiment, an alkyl group may have the structure of formula VI:

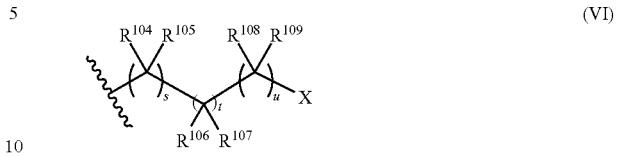

(VI)

$R^{104}$ and $R^{105}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{104}$ and $R^{105}$ are absent when s is 0;

$R^{106}$ and $R^{107}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{106}$ and $R^{107}$ are absent when t is 0;

$R^{108}$ and $R^{109}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{108}$ and $R^{109}$ are absent when u is 0; or $R^{104}$ and $R^{105}$ or $R^{105}$ and $R^{106}$ or $R^{106}$ and $R^{107}$ or $R^{107}$ and $R^{108}$ or $R^{108}$ and $R^{109}$ together with the carbon atoms to which they are attached are linked to form a 3 to 10-membered carbocyclic or heterocyclic ring;

s, t and u are integers from 0 to 5;

X is $NR^{110}R^{111}$, $CR^{112}R^{113}R^{114}$, $OR^{115}$, $SR^{116}$ or halogen;

$R^{110}$ and $R^{111}$ are each independently hydrogen, hydroxy, alkoxy, alkyl, alkenyl, alkynyl, aryl, carbonyl, carboxy, acyl or $NR^{117}R^{118}$ or $R^{109}$ and $R^{110}$ together with the nitrogen to which they are attached are linked to form a 3-10 membered aliphatic, heterocyclic or aromatic ring;

$R^{112}$, $R^{113}$ and $R^{114}$ are each independently hydrogen, hydroxyl, alkyl, alkenyl, alkynyl, aryl, amino, sulfonyl, carbonyl, carboxy, alkoxy, aryloxy, halogen, acyl, oximyl, hydrazinyl, —$NO_2$, —CN, a heterocyclic moiety or thioether, or $R^{112}$ and $R^{113}$ together with the carbon to which they are attached are linked to form a 3-10 membered carbocyclic or heterocyclic ring; or $R^{112}$ is absent and $R^{113}$ and $R^{114}$ together with the carbon to which they are attached are linked to form a 4 to 10 membered aromatic ring;

$R^{115}$ and $R^{116}$ are each independently hydrogen, alkyl, alkenyl, alkynyl, aryl, carbonyl, acyl or a heterocyclic moiety; and $R^{117}$ and $R^{118}$ are each independently hydrogen, alkyl, alkenyl, alkynyl, aryl, carbonyl, acyl or a heterocyclic moiety.

The term "aryl" includes groups, e.g., 5- and 6-membered single-ring aromatic groups, that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, alkyl, alkenyl, alkynyl, halogen, hydroxyl, alkoxy, aryl, alkylcarbonyloxy, arylcarbonyloxy, alkoxycarbonyloxy, aryloxycarbonyloxy, —COOH, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g. , tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

The term "heterocyclic moiety" includes saturated cyclic moieties having a closed ring of atoms in which at least one atom is not a carbon. As used herein, heterocyclic moieties do not include heteroaryl moieties, in which the closed ring of atoms is both heterocyclic and aromatic and/or unsaturated. Examples of heterocyclic moieties include aziridine, ethylene oxide, thiirane, dioxirane, azetidine, oxetane, thietane, dioxetane, dithietane, pyrrolidine, tetrahydrofuran, tetrahydrothiophene, imidazolidine, oxazolidine, thiazolidine, dioxolane, dithiolane, piperidine, tetrahydropyran, thiane, piperzine, pxazine, dithiane, dioxane and trioxane.

The term "heterocyclic moiety" includes both "unsubstituted heterocyclic moieties" and "substituted heterocyclic moieties," the latter of which includes moieties having substituents replacing a hydrogen on one or more of the atoms on the closed ring. Such substituents can include, for example, alkyl, alkenyl, alkynyl, halogens, hydroxyl, aryl alkylcarbonyloxy, arylcarbonyloxy, alkoxycarbonyl oxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropentyl, cyclobutenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ or straight chain, $C_3$-$C_6$ for branched chain). Likewise, cycloalkenyl groups may have from 3-8 carbon atoms in their ring structure. The term $C_2$-$C_6$ includes alkenyl groups containing 2 to 6 carbon atoms.

Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl, alkenyl, alkynyl, halogens, hydroxyl, aryl alkylcarbonyloxy, arylcarbonyloxy, alkoxycarbonyl oxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term "alkynyl" further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl, alkenyl, alkynyl, halogens, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acyl" includes compounds and moieties which contain the acyl radical ($CH_3CO$—). It also includes substituted acyl moieties. The term "substituted acyl" includes acyl groups where one or more of the hydrogen atoms are replaced by for example, alkyl, alkenyl, alkynyl, halogens, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein: an acyl moiety is bonded to an amino group. For example, the term includes alkylcarbonylamino, arylcarbonylamino, carbamoyl and ureido groups.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups.

Examples of substituted alkoxy groups include halogenated alkoxy groups. The alkoxy groups can be substituted with groups such as alkyl, alkenyl, alkynyl, halogen, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes unsubstituted and substituted compounds where a nitrogen atom is covalently bonded to at least one carbon or heteroatom including but not limited to alkyl amino, dialkyl amino, aryl amino, diarylamino, and alkylarylamino. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. The term "arylamino" and "diarylamino" include groups in which the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups, which include aryl or heteroaryl moieties bound to an amino group that is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenyl carbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc. The term "carboxy" further includes the structure of —COOH and —COO$^-$.

The term "oximyl" includes compounds and moieties that contain a carbon connected with a double bond to a nitrogen atom, which is, in turn connected to a hydroxyl or an alkoxyl group. The term "hydrazinyl" includes compounds and moieties that contain a carbon connected with a double bond to a nitrogen atom, which is, in turn, connected to an amino group.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" includes compounds and moieties which contain a sulfur atom bonded to two different carbon or hetero atoms. Examples of thioethers include, but are not limited to, alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyl" refer to compounds or moieties in which an alkyl, alkenyl or alkynyl group is bonded to a sulfur atom that is covalently bonded to an alkenyl or alkynyl group, respectively.

The term "sulfonyl" includes moieties containing a sulfonyl functional group (e.g., $SO_2$) attached to two carbons via a covalent bond to the sulfur atom of the sulfonyl functional group.

The term "sulfonic acid" includes moieties containing a sulfonyl functional group (e.g., $SO_2$) attached to one carbon and one oxygen via covalent bonds.

The term "diazene" and "diazo" include moieties containing two nitrogen atoms covalently double bonded to each other (e.g., N═N). The nitrogen atoms may be covalently bonded to hydrogen, alkyl, alkenyl, alkynyl, hydroxyl or aryl. In some embodiments, the diazene moiety is an aryldiazene, for example, a phenyl diazene, which may be substituted with alkyl, alkenyl, alkynyl, halogens, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "hydroxy" or "hydroxyl" includes groups with an —OH or —O$^-$.

The term "halogen" includes fluorine, bromine, chlorine, iodine, etc.

The term "heteroatom" includes atoms of any element other than carbon or hydrogen. Preferred heteroatoms are nitrogen, oxygen, sulfur and phosphorus.

The language "cosmetically acceptable salts" includes those salts of the dyes of the invention that acceptable for cosmetic application. One of skill in the art would be able to readily ascertain salts that are cosmetically acceptable by referring to, for example, the *International Cosmetic Ingredient Dictionary and Handbook*, Tenth Ed., 2004 (herein incorporated by reference in its entirety).

The dyes of the invention that are basic in nature are capable of forming a wide variety cosmetically acceptable acid addition salts of the dyes of the invention that are basic in nature are those that form non-toxic acid addition salts, i.e., salts containing cosmetically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate (i.e., 1,1'-methylene-bis-(2-hydroxy-3-naphthoate)]salts. The acid addition salts of the base dyes are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other dyes of the invention not specifically described in the experimental section can be accomplished using combinations of the described reactions that will be apparent to those skilled in the art.

The dyes of the invention that are acidic in nature are capable of forming a wide variety of base salts. The chemical bases that may be used as reagents to prepare cosmetically acceptable base salts of the dyes of the invention that are acidic in nature are those that form non-toxic base salts with such compounds. Such non-toxic base salts include, but are not limited to those derived from such cosmetically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammoniums and other base salts of cosmetically acceptable organic amines. The cosmetically acceptable base addition salts of the dyes of the invention that are acidic in nature may be formed with cosmetically acceptable cations by conventional methods. Thus, these salts may be readily prepared by treating the dyes of the invention with an aqueous solution of the desired cosmetically acceptable cation and evaporating the resulting solution to dryness, preferably under reduced pressure. Alternatively, a lower alkyl alcohol solution of the dyes of the invention may be mixed with an alkoxide of the desired metal and the solution subsequently evaporated to dryness.

II. Dye Compositions

In some aspects, the present invention provides dye composition containing at least one dye of the invention and a medium suitable for dyeing keratin fibers (e.g., hair). The language "medium suitable for dyeing keratin fibers" includes mediums that are capable of containing at least one dye of the invention and include, for example, solutions, sprays, rinses, mousses, gels, powders, shampoos and creams.

In some embodiments, the dye compositions contain one or more direct dyes or oxidative dyes in addition to containing at least one dye of the invention. Where the dye composition contains one or more oxidative dyes, the dye or dyes of the invention in the composition may act as a spectator dye. The language "specatator dye" includes the dye of the invention being present in the dye solution or composition but not participating in the oxidative reaction required by the oxidative dyes to provide color.

In other embodiments, the dyes of the invention are formulated as a color booster. The language "color booster" includes dye compositions comprising at least one dye of the invention that may be added to a dye composition containing one or more direct dyes or oxidative dyes in order to enhance the color and/or increase the vibrancy of the dye composition after application to hair. In some embodiments, the color booster may be applied to the hair in the same composition as the dye composition containing one or more direct or oxidative dyes. In other embodiments, the color booster may be applied to the hair in a separate composition from that of the composition containing one or more direct or oxidative dyes, and may be added prior to, at substantially the same time, or after application of the composition containing one or more direct or oxidative dyes.

In other embodiments, the medium is an aqueous medium. The language "aqueous medium" includes a medium that contains about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or about 95% water.

In still other embodiments, the medium further includes one or more of surfactants, thickeners, fragrances, sequestering agents, UV-screening agents, waxes, silicones, preserving agents, ceramides, oils, vitamins, provitamins, opacifiers, couplers, primary intermediates, alkalizing agents, direct dyes, reducing agents, antioxidants, emulsifiers, chelating agents, color retarders, solvents and buffers (e.g., phosphate buffers). Examples of the foregoing agents may be found in the *International Cosmetic Ingredient Dictionary and Handbook*, Tenth Ed., 2004 (herein incorporated by reference in its entirety).

Examples of surfactants include, but are not limited to, oleth 5, oleic acid and sodium lauryl sulfate.

Examples of thickeners include, but are not limited to, fatty alcohols (e.g., oleyl alcohol), ethoxylated phenols (e.g., octoxynol-1, nonoxynol-4, and nonoxynol-9), and polymers (e.g., hydroxyethylcellulose).

Examples of couplers include, but are not limited to, 3-aminophenol, resorcinol, 2-methylresorcinol, 1-naphthol, 2-methyl-5-aminophenol, and 4-amino-2-hydroxytoluene.

An examples of a primary intermediate includes but are not limited to, parapheynylenediamine and 4-aminophenol.

Examples of antioxidants include, but are not limited to, sodium sulfite and erythorbic acid.

Examples of emulsifiers include, but are not limited to, Pluracare L64® and Inconam 30®.

An example of a chelating agent includes, but is not limited to, EDTA.

Examples of solvents include, but are not limited to, water, $C_1$ to $C_4$ lower alcohols (e.g., ethanol, 2-propanol and isopropanol), acetone, methylethylcetone, ethyl acetate, methyl acetate, butyl acetate, diethoxyethane, dimethoxyethane, $C_6$ to $C_{10}$ alkanes, dimethyl isosorbide, ethoxydiglycol and propylene glycol.

Examples of alkalizing agents include, ammonium hydroxide, ammonia, alkylamines (e.g., ethylamine; dipropylamine; triethylamine; n-propylamine, isobutylamine, 2-ethylbutylamine, diethylamine), alkanediamines (e.g., 1,3-diaminopropane; ethylenediamine; 1,2-diaminopropane;

diethylenetriamine; triethylenetriamine; 2,2'-iminodipropylamine; 3,3-iminodipropylamine; and bis-hexamethylenetriamine), alkanolamines (e.g., ethanolamine, diethanolamine, isopropanolamine; di-isopropanolamine; triethanolamine; triisopropanolamine; N-methyldiethanolamine; diisopropylethanolamine; dimethylisopropanolamine; 2-amino-2-methylpropane-1,3-diol; tris(hydroxymethyl)methylamine; N-(2-hydroxyethyl)aniline; N-methyl-N(2-hydroxyethyl) aniline; N,N-bis(2-hydroxyethyl)aniline), polyalkylenepolyamines, (e.g., diethylenetriamine), heterocyclic amines (e.g., morpholine; N-methylmorpholine, N-ethylmorpholine, N-hydroxyethylmorpholine, N-phenylmorpholine, piperidine, N-hydroxyethylpiperidine, and piperazine), alkaline earth hydroxides (e.g., calcium hydroxide or magnesium hydroxide) alkali metal hydroxide (e.g., sodium hydroxide or potassium hydroxide), or carbonates (e.g., sodium carbonate and bicarbonate).

In particular embodiments, the alkalizing agent is present in the composition between about 0.05% to about 10%, between about 0.1% and about 5% or between about 1.5% to about 3.5%.

In some embodiments, the dye composition is formulated in a cosmetically acceptable composition. The language "cosmetically acceptable composition" includes dye compositions that comprise at least one dye of the invention and are suitable for cosmetic application. One of skill in the art would be able to readily ascertain formulations and compositions that are cosmetically acceptable by referring to, for example, the *International Cosmetic Ingredient Dictionary and Handbook*, Tenth Ed., 2004 (herein incorporated by reference in its entirety).

In some embodiments, the dye composition comprises about 3% dye of the invention, about 15% of an emulsifier (e.g., Pluracare L64® or Incronam 30®), about 25% of a solvent (e.g., dimethyl isosorbide) and about 53% aqueous phosphate buffer.

In other embodiments, the dye composition comprises about 0.1% to 3% dye of the invention, about 50% solvent (e.g., ethanol) and the remaining solution of a phosphate buffer.

In still other embodiments, the dye composition comprises about 0.1-3% dye of the invention, between about 1.5% to about 3.5% ammonia, about 0.05% stabilizer (e.g., EDTA), about 0.4% antioxidant (e.g., sodium sulfite and/or isoascorbic acid), between about 20% and about 25% of solvent (e.g., ethoxydiglycol) and about 30% surfactant (e.g., oleth-5 and/or oleic acid) with the remaining solution comprising water.

In still other embodiments, the dye composition comprises about 0.1-3% dye of the invention, between about 1.5% to about 3.5% ammonia, about 0.05% stabilizer (e.g., EDTA), about 0.2% antioxidant (e.g., sodium sulfite), between about 8% and about 25% solvent (e.g., propylene glycol and/or 2-propanol), about 2% surfactant (e.g., sodium lauryl sulfate), about 21% buffer (e.g., oleic acid), about 10% thickener (e.g., oleyl alcohol) with the remaining solution comprising water.

In some embodiments, the dyes of the invention are formulated in an after-coloring conditioner (e.g., L'Oréal Superior Preference Care Suprême Color-Saving Conditioner) and similar formulations for application during conditioning.

III. Methods

In some aspects, the present invention provides methods for coloring keratin fibers by applying to the keratin fibers a dye composition comprising at least one dye of the invention. The term "keratin fibers" includes human hair and animal fur.

In some aspects, the present invention provides methods for coloring synthetic hair by applying to the synthetic hair a dye composition comprising at least one dye of the invention. The term "synthetic hair" includes hair or fur made from non-natural fibers, for example, fake or "faux" fur and synthetic hair wigs.

In some aspects, the present invention provides methods for coloring hair by applying to hair a dye composition comprising at least one dye of the invention. The language "coloring hair" includes treating substantially all of the hair on a person's head or some of the hair on a person's head In some aspects, the present invention provides methods for coloring damaged hair by applying to hair a dye composition comprising at least one dye of the invention. The language "coloring damaged hair" includes treating all of the hair on a person's head or some of the hair on a person's head, where the hair is more porous than normal hair.

In some aspects, the present invention provides methods for highlighting hair by applying to hair a dye composition comprising at least one dye of the invention. The language "highlighting hair" includes treating some of the hair on a person's head.

In other aspects, the present invention provides methods for touching up hair roots by applying to the roots a dye composition comprising at least one dye of the invention. The language "touching up hair roots" includes treating the hair on a person's head that is closest to the scalp.

In some embodiments, the dye composition comprising at least one dye of the invention is applied to wet or dry hair.

In other embodiments, the methods include the step of leaving the composition comprising at least one dye of the invention on the hair for between about 1 and 60 minutes.

In some other embodiments, the methods include the steps of a) treating the hair with an oxidative dye in the presence of ammonia and optionally hydrogen peroxide for between about 1 and about 60 minutes; b) optionally rinsing the hair; and optionally partially drying the hair; c) treating the hair with a dye composition comprising at least one dye of the invention for between about 1 and about 60 minutes; and d) rinsing the hair. The methods may also include the steps of e) washing the hair with shampoo and/or conditioning the hair with conditioner after rinsing the hair; f) rinsing the hair; and g) optionally drying the hair.

In some embodiments, the methods further comprises the steps of a) treating the hair with a dye composition comprising at least one dye of the invention optionally containing one or more oxidative dye precursors and/or one or more direct dyes with one or more alkalizing agents and, optionally, hydrogen peroxide for between about 1 and about 60 minutes; b) rinsing the hair; c) washing the hair with shampoo and/or conditioning the hair with conditioner; d) rinsing the hair; and e) optionally drying the hair.

IV. Kits

In some aspects, the present invention provides for kits comprising a dye composition comprising at least one dye of the invention instructions for use. In some embodiments, the dye is formulated as a cosmetically acceptable formulation. In some embodiments, the cosmetically acceptable formulation may further comprise ammonia.

In other embodiments, the kit may contain, for example, a developer bottle, gloves or a conditioning rinse. In some other embodiments, the developer bottle contain may contain a solution comprising hydrogen peroxide. In yet other embodiments, one or more dyes of the invention are packaged separately from the dye composition.

EXEMPLIFICATION OF THE INVENTION

The methods of this invention can be understood further by the following examples. It will be appreciated, however, that these examples do not limit the invention. Variations of the invention, now known or further developed, are considered to fall within the scope of the present invention as described herein and as hereinafter claimed.

Example 1

Synthesis of Selected Dyes of the Inventions

Synthesis of Compounds A-F: The synthesis of compounds A-F were synthesized as shown below in Scheme 1.

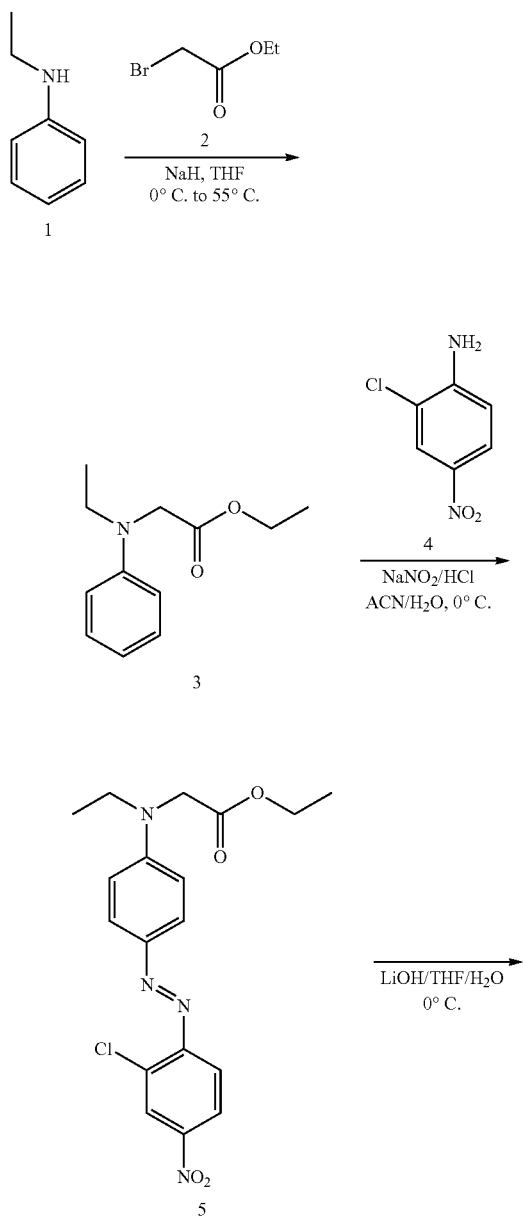

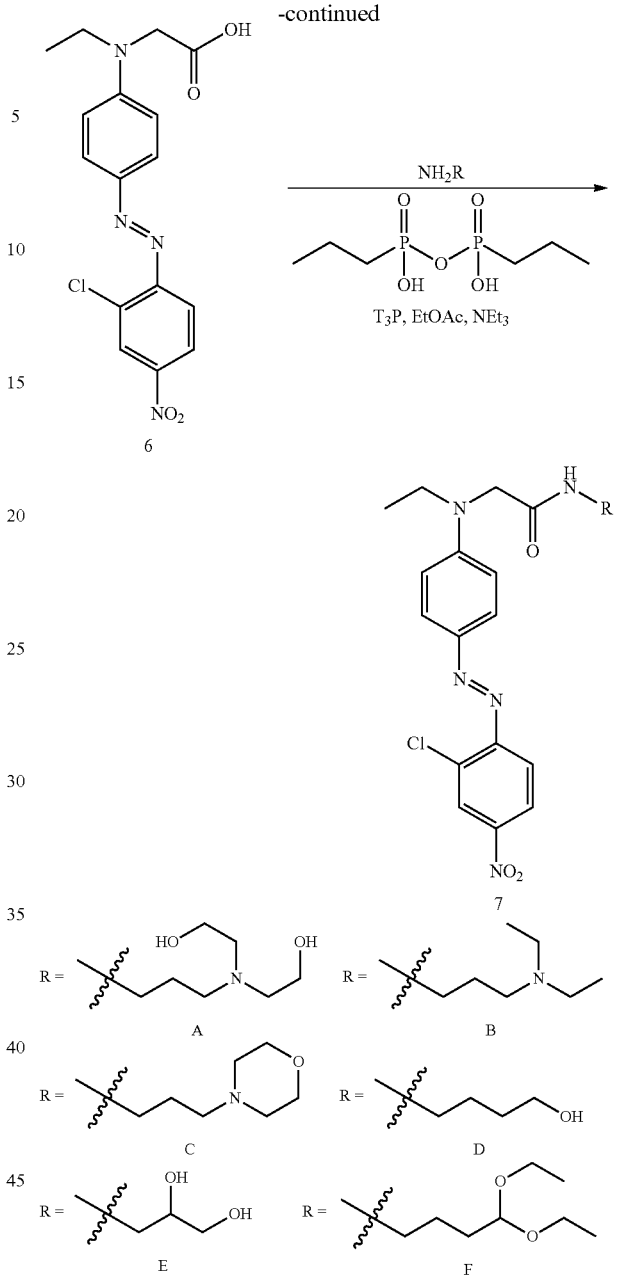

N-Ethylaniline (1, 50.00 g, 0.412 mol) was added to a stirred solution of NaH (1.2 eq, 11.86 g, 0.495 mol) in THF (300 mL) at 0° C. followed by ethyl bromoacetate (2, 1.2 eq, 82.69 g, 0.495 mol). The reaction mixture was warmed to room temperature and continued stirring for 30 minutes. The reaction mixture temperature was increased to 55° C. and stirred for 14 hours. The reaction mixture was brought to room temperature, quenched with ice-water and extracted with EtOAc (3×300 mL). The resultant extracted EtOAc was washed with water (2×300 ml), dried over $Na_2SO_4$, and concentrated. The concentrated product was purified through column chromatography using 5% EtOAc in petroleum ether to afford compound 3 as brown liquid (80 g, 93.5%). Rf: 0.8 (petroleum ether: EtOAc, 9:1). $^1H$ NMR (300 MHz, $CDCl_3$): δ 7.27-7.20 (m, 2H), 6.75-6.65 (m, 3H), 4.21 (q, J=7.1 Hz, 2H), 4.02 (s, 2H), 3.99 (q, J=7.1 Hz, 2H), 1.27 (t, J=7.1 Hz, 3H), 1.22 (t, J=7.1 Hz, 3H). LCMS, single peak, 4.188 min, ES-APCI: m/z 208.2 [M+H]+.

To a stirred solution of 2-chloro-4-nitroaniline (4, 1.5 eq, 50.00 g, 0.289 mol) in acetonitrile (715 mL) and 1N HCl (1.285 L) was added dropwise NaNO$_2$ (1.5 eq, 20.00 g, 0.289 mol) in water (150 mL) at 0° C. over a period of 30 minutes and continued stirring for 1.5 hour. The resultant reaction mixture was added to 3 (1.0 eq, 38.25 g, 0.185 mol) with sulfamic acid (0.1 eq, 1.80 g, 18.5 mmol) in acetonitrile (1.150 L) and 1 M HCl (1.150 L) at 0° C. over a period of 45 minutes with continued stirring for 60 minutes. Saturated sodium bicarbonate was then added to the resultant reaction mixture at 0° C. to adjust to a pH of about 1 and the mixture was stirred for 1.2 hours at the same temperature. Next, the reaction mixture was extracted with dichloromethane (4×1 L), dried over Na$_2$SO$_4$, and concentrated. The concentrated product was stirred with methyl t-butyl ether (500 ml) for 30 minutes and filtered to afford 5 as dark red solid (35 g, 48.5%). Rf: 0.6(pet. ether: EtOAc, 9:1). $^1$H NMR (400 MHz, DMSO-d6): δ 8.46 (bs, 1H), 8.28-8.25 (m, 1H), 7.88 (d, J=9.0 Hz, 2H), 7.79 (d, J=8.9 Hz, 1H), 6.84 (d, J=9.0 Hz, 2H), 4.38 (s, 2H), 4.16 (q, J=7.1 Hz, 2H), 3.58 (q, J=7.1 Hz, 2H), 1.22 (t, J=7.1 Hz, 3H), 1.82 (t, J=7.1 Hz, 3H). LCMS, single peak, 4.965 min, ES-APCI: m/z 390.9 [M+H]+.

Lithium hydroxide (2.6 eq, 3.23 g, 0.135 mol) in H$_2$O (20 mL) was added to a stirred solution of 5 (1.0 eq, 20.00 g, 0.051 mol) in tetrahydrofuran (120 mL) and water (120 mL) at 0° C., which was allowed to stir at room temperature for 1.5 hours. The tetrahydrofuran was evaporated under vacuum and the pH adjusted to approximately 7 using a citric acid solution. The resultant reaction mixture was extracted with ethyl acetate (2×200 mL). The organic layer was dried over Na$_2$SO$_4$ and concentrated. The concentrated product was triturated with 100 mL Et$_2$O-EtOAc (8:2) to afford 6 as a dark pink solid (14 g, 75.4%). Rf 0.2 (CHCl$_3$:MeOH, 9:1). $^1$H NMR (300 MHz, CDCl$_3$): δ 8.35 (s, 1H), 8.12 (d, J=9.0 Hz, 1H), 7.90 (d, J=9.3 Hz), 7.73 (d, J=9.0 Hz, 1H), 6.70 (d, J=9.3 Hz, 2H), 4.10 (s, 2H), 3.55 (q, J=7.1 Hz, 2H), 1.26 (t, J=7.2 Hz, 3H). LCMS, single peak, 4.729 min, ES-APCI: m/z 362.9 [M+H]+. HPLC purity: 97.6%.

Compound A: N-(3-aminopropyl)diethanolamine (1 eq, 298 mg, 1.84 mmol, CAS #4985-85-7) was dissolved in 10 mL of 9:1 CH$_2$Cl$_2$:DMF. An amount of 1-ethyl-3-(3-dimethylaminopropyl)carbodiimide hydrochloride (EDC, 2.0 eq, 571 mg, 3.68 mmol), 1-hydroxybenzotriazole hydrate (HOBt, 1.5 eq, 422 mg, 2.76 mmol), and N,N-diisopropylethylamine (DIPEA, 2.0 eq, 640 μL, 3.68 mmol) were added to a stirring solution of amine. Compound 6 (1.2 eq, 1.00 g, 2.76 mmol) was dissolved in 5 mL of 9:1 CH$_2$Cl$_2$:DMF and added to the reaction vessel. The mixture was stirred at room temperature overnight and was subsequently diluted with 30 mL of CH$_2$Cl$_2$ and washed with saturated sodium bicarbonate (2×30 mL) and brine (1×30mL), dried over Na$_2$SO$_4$ and concentrated by rotary evaporation. After column chromatography (2×), the yield was 47%. $^1$H NMR (300 MHz, CDCl$_3$): δ 8.25 (s, 1H), 8.04 (d, J=9.0 Hz, 1H), 7.85 (d, J=9.0 Hz, 2H), 7.67 (d, J=9.0 Hz, 1H), 6.89 (bt, J=5.9 Hz, 1H, NH), 6.72 (d, J=9.0 Hz, 2H), 3.98 (s, 2H), 3.54 (m, 6H), 3.40 (q, J=6.7 Hz, 2H), 2.53 (t, J=5.0 Hz, 4H), 2.46 (t, J=6.2 Hz, 2H), 1.65 (quintet, J=6.3 Hz, 2H), 1.27 (t, J=6.7 Hz, 3H). LCMS, single peak, 2.554 min, ES-APCI: m/z 507.2 [M+H]+.

Compound B: Using a similar procedure as outlined for compound A, an amount of 6 (1.2 eq, 435 mg, 1.20 mmol) was reacted with and 3-(diethylamino)polyamine (1.0 eq, 130 mg, 158 μL, 1.00 mmol, CAS#104-78-9). In addition to the washes, the organic fractions were taken up in CH$_2$Cl$_2$ and loaded onto a Thermo Scientific 5 g HyperSep SCX cartridge. The cartridge was washed with 25 mL each of CH$_2$Cl$_2$ then MeOH and was then eluted with 2 M NH$_3$ in MeOH to yield a dark red/purple solid. Yield: 78%. $^1$H NMR (300 MHz, CDCl$_3$): δ 8.40 (s, 1H), 8.16 (d, J=9.0 Hz, 1H), 7.95 (d, J=9.0 Hz, 2H), 7.78 (d, J=9.0 Hz, 1H), 7.67 (bt, 1H, NH), 6.77 (d, J=9.0 Hz, 2H), 3.99 (s, 2H), 3.57 (q, J=7.1 Hz, 2H), 3.38 (q, J=6.1 Hz, 2H), 2.41 (t, J=6.1 Hz, 2H), 2.34 (q, J=7.1 Hz, 4H), 1.59 (quintet, J=6.1 Hz, 2H), 1.27 (t, J=7.1 Hz, 3H), 0.84 (t, J=7.1 Hz, 6H). LCMS, single peak, 3.257 min, ES-APCI: m/z 475.2 [M+H]+.

Compound C: Compound C was synthesized in a similar manner as compound A, above. Starting with compound 6 (1.2 eq, 268 mg, 0.739 mmol) and reacting with N-(3-aminopropyl)morpholine (1.0 eq, 88.8 mg, 89.7 μL, 0.616 mmol, CAS#123-00-2) yielded a dark red/purple residue. Yield: 90%. $^1$H NMR (400 MHz, CDCl$_3$): δ 8.41 (d, 1H, J=2.4 Hz), 8.17 (dd, 1H, J=2.4 Hz, and 8.9 Hz), 7.97 (d, 2H, J=9.1 Hz), 7.78 (d, 1H, J=8.9 Hz), 7.0 (brs, 1H), 6.81 (d, 2H, J=9.1Hz), 4.01 (s, 2H), 3.62-3.59 (m, 6H), 3.38 (q, 2H, J=6.3 Hz), 2.36 (brs, 6H), 1.70 (t, 2H, J=6.4 Hz), 1.30 (t, 3H, J=7.0 Hz). LCMS, single peak, 3.935 min, ES-APCI: m/z 489.2 [M+H]+.

Synthesis of Compounds G and J: Compounds G and J were synthesized as shown in Scheme 2.

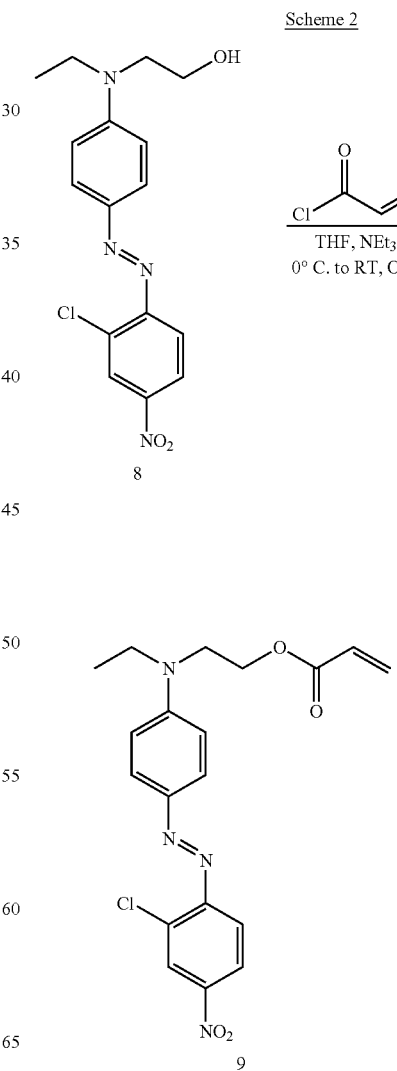

Scheme 2

Synthesis of Compounds U-AA: Compounds U-AA were synthesized as shown in Scheme 3.

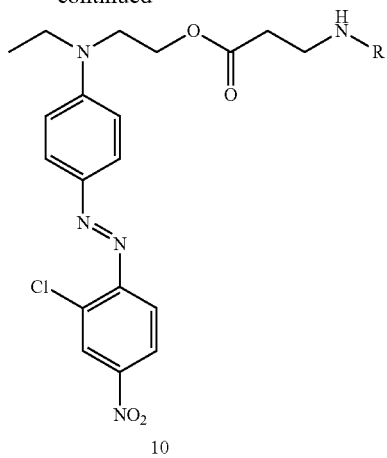

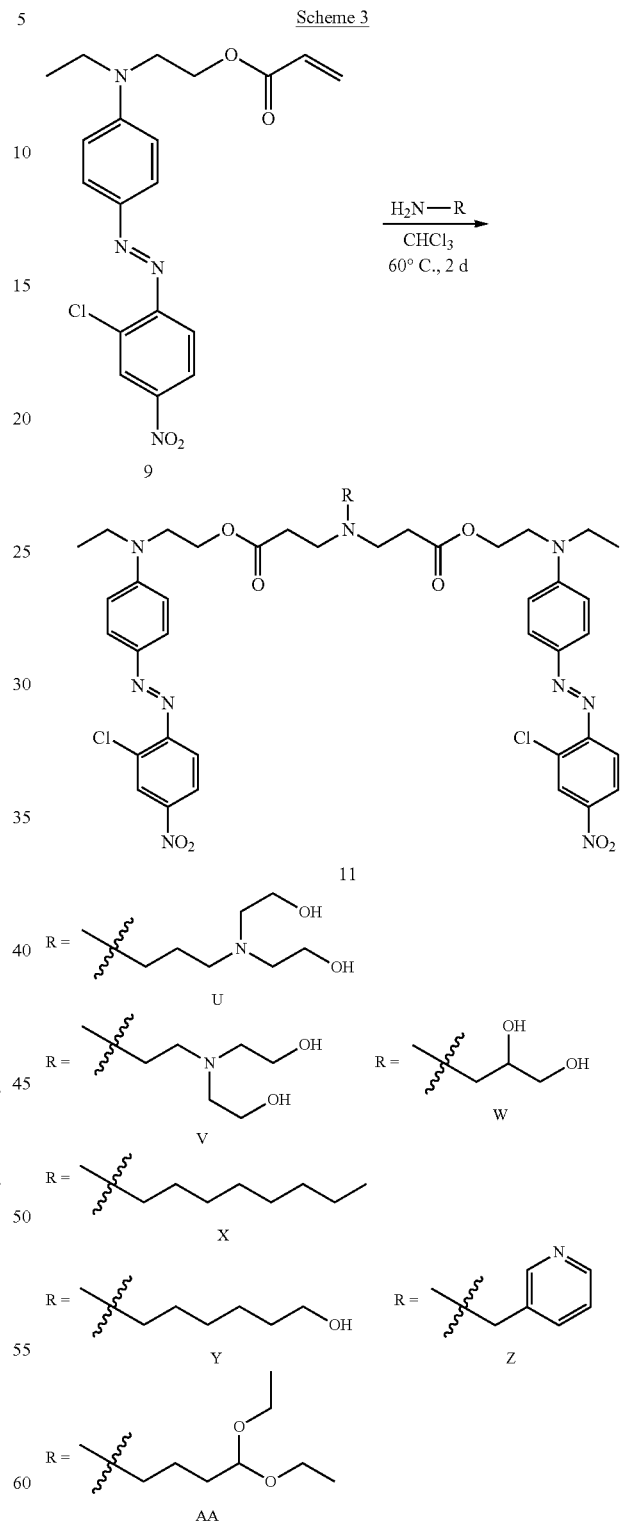

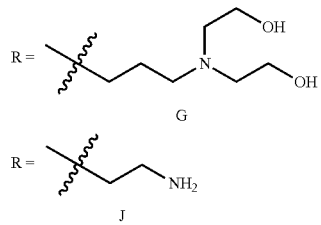

Compound 9 was either purchased from Polymer Source, Inc. or synthesized as follows: Disperse red 13 dye (8, 13.14 g, 37.68 mmol, 1.0 eq) was dissolved in 250 mL of tetrahydrofuran (THF) and triethylamine ($NEt_3$, 33.62 mL, 241 mmol, 6.4 eq), and the mixture was cooled in an ice bath. Acryloyl chloride (5.70 g, 5.36 mL, 65.95 mmol, 1.75 eq) was added in 55 mL of THF dropwise with an addition funnel to the reaction mixture with stiffing. The mixture was then allowed to warm to room temperature and was stirred overnight. Excess acryloyl chloride was quenched with the addition of 200 mL of saturated sodium bicarbonate, and the product was extracted with 1×200 mL and 2×100 mL of $CHCl_3$. The organic portion was dried over $Na_2SO_4$ and concentrated by rotary evaporation to yield a dark red/purple residue. Co-evaporation with a 125 mL of a 3:2 mixture of acetone and MeOH led to the isolation of a dark purple solid (9). Yield: 96%. $^1$H NMR ($CDCl_3$, 300 MHz, 25° C.): δ 8.38 (s, 1H), 8.14 (d, J=9.0 Hz, 1H), 7.94 (d, J=9.2 Hz, 2H), 7.77 (d, J=9.0 Hz, 1H), 6.81 (d, J=9.2 Hz, 2H), 6.42 (d, J=17.5 Hz, 1H), 6.12 (dd, J=17.5, 10.4 Hz, 1H), 5.87 (d, J=10.4 Hz, 1H), 4.36 (t, J=6.2 Hz, 2H), 3.74 (t, J=6.2 Hz, 2H), 3.54 (q, J=7.1 Hz, 2H), 1.27 (t, J=7.1 Hz, 3H).

Compound J: Ethylene diamine (323 mg, 360 µL, 5.37 mmol, 1.0 eq) was dissolved in 10 mL of $CHCl_3$ and cooled on ice. Compound 9 (2.16 g, 5.37 mmol) was dissolved in 15 mL of $CHCl_3$ and added dropwise via syringe to the stiffing, cooled mixture. The mixture was stirred at 50-60° C. for 2 days. $^1$H NMR ($CDCl_3$, 400 MHz, 25° C.): δ 8.37 (s, 1H), 8.14 (d, J=9.0 Hz, 1H), 7.92 (d, 2H), 7.77 (d, J=9.0 Hz, 1H), 6.79 (d, 2H), 4.31 (m, 2H), 3.69 (t, 2H), 3.53 (t, 2H), 2.87 (m, 2H), 2.75 (m, 2H), 2.65 (m, 2H), 2.51 (m, 2H), 1.26 (t, 3H).

Compounds U-AA were prepared by dissolving compound 9 in $CHCl_3$ and adding compound 9 dropwise to 0.5 eq of amine dissolved in $CHCl_3$ and cooled on ice. The mixture was stirred at 50-60° C. for 2 days.

Synthesis of Compounds AB-AH: Compounds AB-AH were synthesized as shown in Scheme 4.

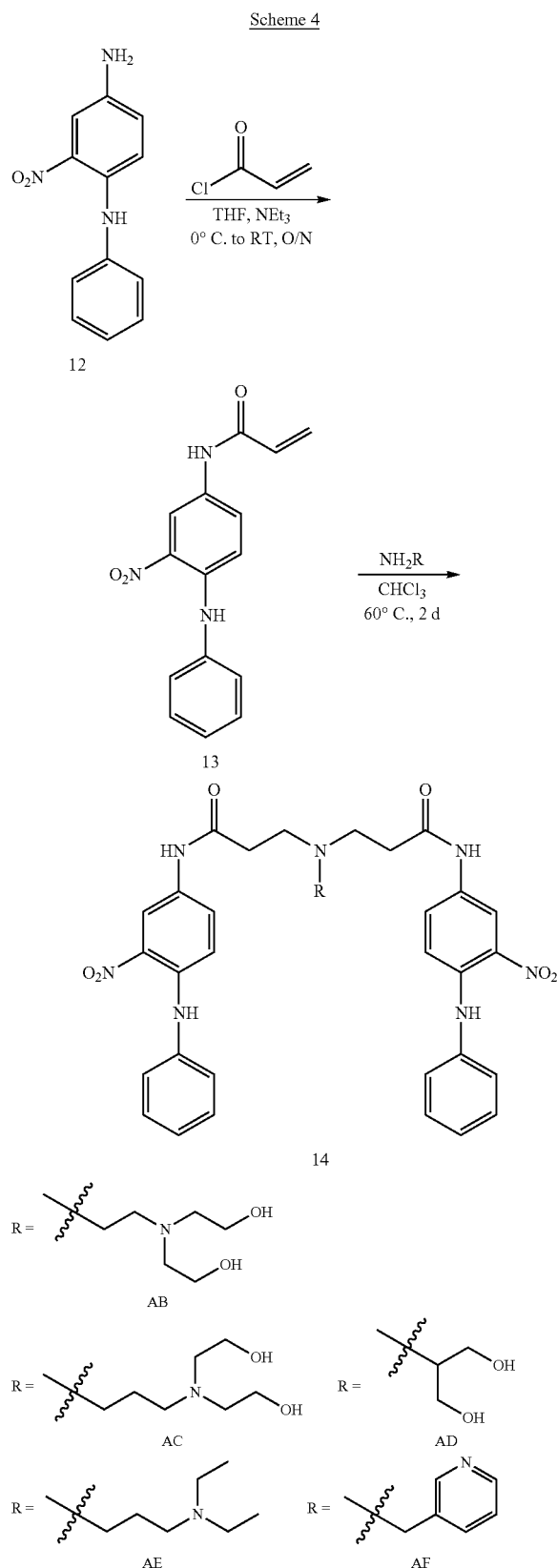

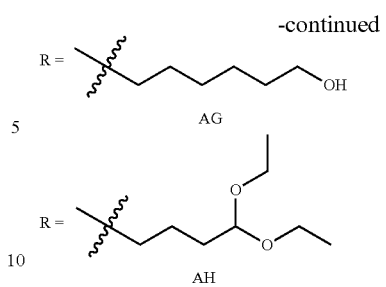

Using a similar procedure as outlined immediately above, compounds AB-AH were synthesized. Compound 13 is synthesized as follows: Compound 12 (1.0 eq) is dissolved in 250 mL of tetrahydrofuran (THF) and triethylamine (NEt$_3$, 6.4 eq), and the mixture is cooled in an ice bath. Acryloyl chloride (1.75 eq) is added in 55 mL of THF dropwise with an addition funnel to the reaction mixture with stirring. The mixture is then allowed to warm to room and is stirred overnight. Excess acryloyl chloride is quenched with the addition of 200 mL of saturated sodium bicarbonate, and the product is extracted with 1×200 mL and 2×100 mL of CHCl$_3$. The organic portion is dried over Na$_2$SO$_4$ and concentrated by rotary evaporation. Co-evaporation with a 125 mL of a 3:2 mixture of acetone and MeOH leads to the isolation of compound 13.

Synthesis of Compounds AI and AJ: Compounds AI and AJ were synthesized as shown in Scheme 5.

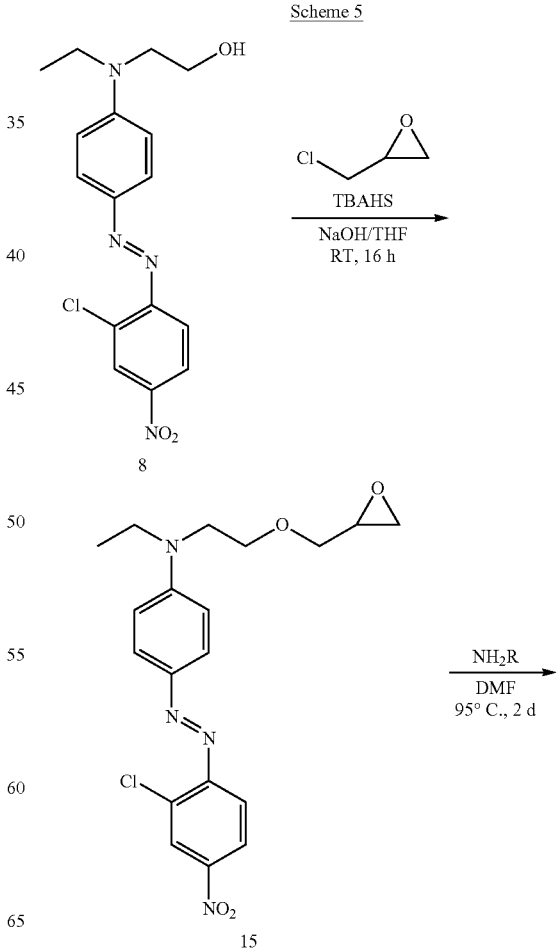

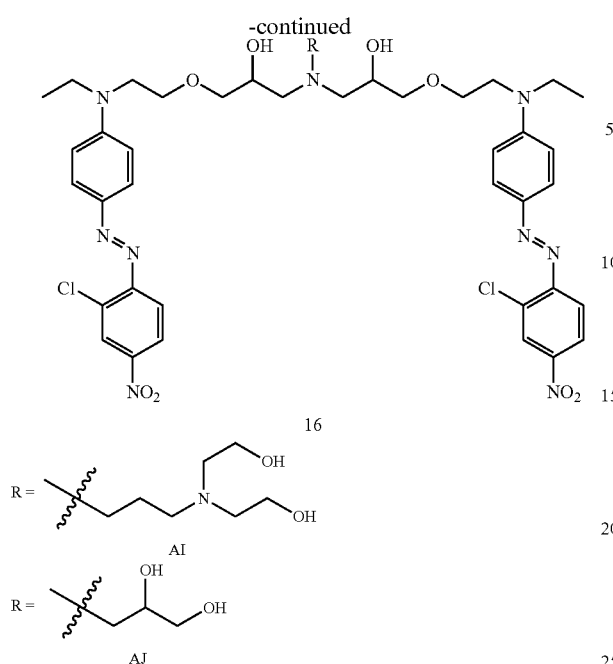

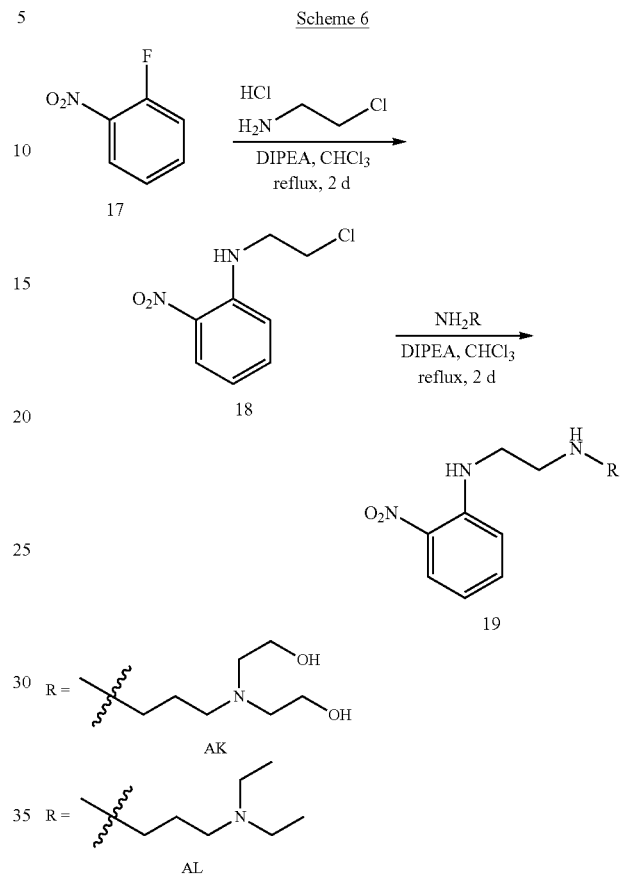

Synthesis of Compounds AK and AL: Compounds AK and AL were synthesized as shown in Scheme 6.

Compound 8 (5.00 g, 14.34 mmol) was added to a stirred solution of epichlorohydrin (2.0 eq, 2.65 g, 28.65 mmol) in 50% aq. sodium hydroxide (25 g of NaOH in 50 ml of $H_2O$) and THF (10 ml) followed by addition of tetrabutylammoniumhydrogen sulfate (0.1 eq, 470 mg, 1.41 mmol) at room temperature. The resultant reaction mixture was stirred vigorously using a mechanical stirrer for 16 hours at room temperature. After completion of the reaction, water (20 ml) was added to reaction mixture, and the product was extracted with dichloromethane (2×200 ml). The extracted dichloromethane was dried over $Na_2SO_4$ and concentrated by rotary evaporation. The resulting concentrated product was purified through column chromatography using 80% dichloromethane in pet ether to afford pure product 15 as a dark purple/black viscous liquid (3.5 g, 60%). Rf 0.4 (pet ether:ethyl acetate, 7:3). $^1$H NMR (400 MHz, $CDCl_3$): δ 8.41 (s, 1H), 8.16 (d, J=8.9 Hz, 1H), 7.96-7.93 (d, J=9.2 Hz, 2H), 7.79 (d, J=8.9 Hz, 1H), 6.79 (d, J=9.2 Hz, 2H), 3.74-3.71 (m, 1H), 3.80-3.72 (m, 2H), 3.68-3.62 (m, 2H), 3.58 (q, J=7.1 Hz, 2H), 3.39 (dd, J=11.6, 6.0 Hz, 2H), 3.18-3.14 (m, 1H), 2.83-2.81(m, 1H), 2.63-2.61 (m, 1H), 1.27 (t, J=7.1 Hz, 3H). $^{13}$C NMR (100 MHz, $CDCl_3$): δ 153.2, 152.0, 147.0, 144.2, 133.9, 127.1, 126.1, 122.7, 118.0, 111.5, 72.1, 69.0, 50.9, 50.4, 46.2, 44.1, 12.3. LCMS, single peak, 4.130 min, ES-APCI: m/z 404.9 [M+H]+.

Compound AJ: Epoxide 15 (1.00 g, 2.47 mmol) was dissolved in 900 μL of DMF. Neat (±)-3-amino-1,2-propanediol (0.5 eq, 113 mg, 1.24 mmol) was added to the stirring reaction mixture. The mixture was stirred at 95° C. overnight. The mixture was diluted into 20 mL of EtOAc and washed saturated sodium bicarbonate (2×15 mL) and brine (1×10 mL), dried over $Na_2SO_4$ and concentrated by rotary evaporation to yield a dark red purple residue. The yield was quantitative. $^1$H NMR (400 MHz, $CDCl_3$): δ 8.37 (s, 2H), 8.15 (d, J=8.9 Hz, 2H), 7.92 (d, J=9.2 Hz, 4H), 7.78 (d, J=8.9 Hz, 2H), 6.77 (d, J=9.2 Hz, 4H), 3.83 (m, 2H), 3.67 (m, 4H), 3.63 (m, 5H), 3.53 (m, 5H), 3.45 (m, 3H), 3.38 (m, 2H), 2.65 (m, 1H), 2.60 (m, 4H), 2.44 (m, 1H), 1.62 (s, 3H, —OH), 1.23 (t, J=7.1 Hz, 6H).

2-Chloroethylamine hydrochloride (14.32 g, 123.5 mmol, 3.3 eq) was dissolved in 100 mL of chloroform and N,N-diisopropylethylamine (DIPEA, 32.59 mL, 24.18 g, 187.1 mmol, 5.0 eq). 1-Fluoro-2-nitrobenzene (17, 5.28 g, 3.97 mL, 37.42 mmol, 1.0 eq) was slowly added to the stiffing mixture at room temperature. The mixture was then heated to reflux under a condenser for 2 days. The reaction mixture was diluted with 100 mL of water, and the product was extracted with 1×50 mL and 1×25 mL of $CHCl_3$. The organic portion was washed with 1×100 mL and 1×50 mL of brine, dried over $Na_2SO_4$, and concentrated by rotary evaporation to yield the product 18 as an orange residue. Yield: 22%. $^1$H NMR ($CDCl_3$, 400 MHz, 25° C.): δ 8.25 (s, 1H, NH), 8.19 (dd, J=8.6, 1.5 Hz, 1H), 7.50-7.43 (m, 1H), 6.86 (d, J=8.6 Hz, 1H), 6.70 (ddd, J=10.6, 5.9, 2.4 Hz, 1H), 3.80-3.74 (m, 2H), 3.74-3.67 (m, 2H).

Compound AK: Compound 18 (1.26 g, 6.28 mmol) was dissolved in 15 mL of $CHCl_3$ and DIPEA (5.47 mL, 4.06 g, 31.40 mmol, 5.0 eq). N-(3-aminopropyl)diethanolamine (3.06 g, 3.70 mL, 18.84 mmol, 3.0 eq) was dissolved in 10 mL of $CHCl_3$ and was added to the stiffing reaction mixture along with approximately 5 mL of $CHCl_3$ rinse. The mixture was heated to reflux for 2 days. The product was purified through column chromatography eluting with 0.5% triethylamine and 4% methanol in chloroform. Yield: 23%. $^1$H NMR ($CDCl_3$, 400 MHz, 25° C.): δ 8.15 (bs, 1H, NH), 8.12 (dd, J=8.6, 1.6 Hz, 1H), 7.41 (ddd, J=8.5, 7.0, 1.2 Hz, 1H), 6.85 (dd, J=6.7, 1.9 Hz, 1H), 6.61 (ddd, J=8.4, 5.6, 1.2 Hz, 1H), 3.63 (dd, J=6.8, 3.7 Hz, 4H), 3.45 (s, 1H, NH), 3.38 (dd, J=12.1, 6.7 Hz, 2H), 3.10-2.46 (m, 10H), 1.88 (p, J=6.8 Hz, 2H).

Synthesis of Compound AN: Compound AN was synthesized as shown in Scheme 7.

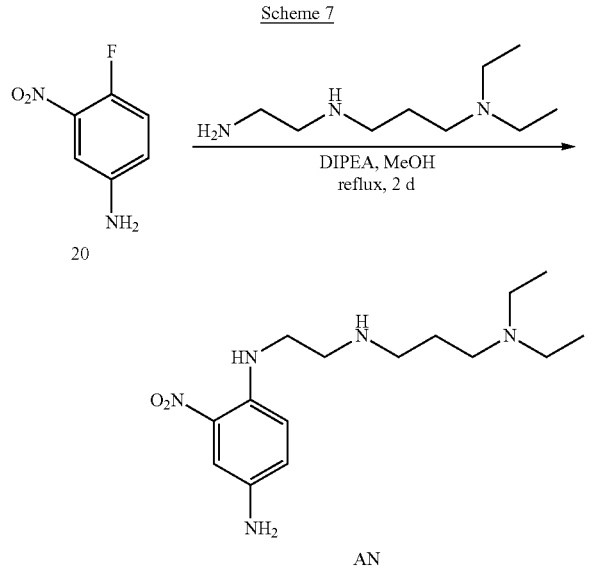

Scheme 7

AN

Compound AN: 4-Fluoro-2-nitroaniline (20, 1.08 g, 6.91 mmol) was dissolved in 8 mL of methanol and DIPEA (4.61 mL, 3.42 g, 26.48 mmol, 3.8 eq). $N^3$-(2-aminoethyl)-$N^1$,$N^1$-diethyl-1,3-propanediamine (1.73 g, 10.00 mmol, 1.4 eq) was dissolved in 5 mL of methanol and was added to the stiffing reaction mixture along with approximately 5 mL of methanol rinse. The mixture was heated to reflux for 2 days. The product was purified through column chromatography eluting with 1% triethylamine and 4% methanol in chloroform. Yield: 3.8%. $^1$H NMR (400 MHz, MeOD) δ 7.50 (d, J=2.7 Hz, 1H), 7.09 (dd, J=9.1, 2.8 Hz, 1H), 6.92 (d, J=9.1 Hz, 1H), 3.45 (t, J=6.3 Hz, 2H), 2.87 (t, J=6.3 Hz, 2H), 2.65 (t, J=7.0 Hz, 2H), 2.63-2.49 (m, 6H), 1.76-1.63 (m, 2H), 1.11-0.99 (t, J=7.2 Hz, 6H).

Example 2

Exemplary Formulations

The formulations set forth below were prepared for testing certain dyes of the invention. One of skill in the art would be able to determine the appropriate amounts or ranges of the formulation components with no more than routine experimentation.

Formulation 1

| Ingredients | % w/w |
|---|---|
| Phosphate Buffer w/DI water | q.s. |
| Dimethyl Isosorbide (Solvent) | 25% |
| Pluracare L64 (Emulsifier) | 15% |
| Compound G (Dye) | 3% |

Formulation 2

| Ingredients | % w/w |
|---|---|
| Phosphate Buffer w/DI water | q.s. |
| Dimethyl Isosorbide (Solvent) | 24% |
| Incronam 30 (Emulsifier) | 15% |
| Compound U (Dye) | 3% |

Formulation 3

| Ingredients | % w/w |
|---|---|
| Phosphate Buffer w/DI water | q.s. |
| Ethanol (Solvent) | 50% |
| Compound AC (Dye) | 0.1-3% |

Formulation 4

| Ingredients | % w/w |
|---|---|
| Water | q.s. |
| EDTA (stabilizer) | 0.05% |
| Sodium sulfite (antioxidant) | 0.2% |
| Isoascorbic acid (aka erythorbic acid, antioxidant) | 0.2% |
| Ethoxydiglycol (aka transcutol, solvent) | 20-25% |
| Oleth-5 (tradename Volpo 5, surfactant) | 10% |
| Oleic acid (surfactant/buffer) | 20% |
| Ammonia | 1.68-3.36% |
| Compound B (Dye) | 0.1-3% |

Formulation 5

| Ingredients | % w/w |
|---|---|
| Water | q.s. |
| EDTA (stabilizer) | 0.05% |
| Sodium sulfite (antioxidant) | 0.2% |
| Propylene glycol (solvent) | 3-5% |
| 2-propanol (solvent) | 5-20% |
| Sodium lauryl sulfate (surfactant) | 2% |
| Oleic acid (surfactant/buffer) | 21% |
| Oleyl alcohol (tradename Lipocol O/95, thickener) | 10% |
| Ammonia | 1.68-3.36% |
| Compound B (Dye) | 0.1-3% |

Formulation 6

| Ingredients | % w/w |
|---|---|
| Water | q.s. |
| EDTA (stabilizer) | 0.2% |
| Sodium sulfite (antioxidant) | 1.0% |
| Ethoxydiglycol (tradename Transcutol CG, solvent) | 5-10% |
| Paraphenylenediamine (PPD, primary intermediate) | 0.3% |

-continued

| Ingredients | % w/w |
|---|---|
| 3-Aminophenol (MAP, coupler) | 0.06% |
| Resorcinol (coupler) | 0.24% |
| Cetyl alcohol (tradename Lanette 16, fatty alcohol) | 2% |
| Emulium Delta (fatty alcohol blend) | 8% |
| Neopentyl glycol diheptanate (tradename Lexfeel 7) | 5% |
| Aminomethylpropylamine (AMP, base) | 0.2-1% |
| Compound AK (Dye) | 0.1-3% |

Formulation 7

| Ingredients | % w/w |
|---|---|
| Water | q.s. |
| EDTA (stabilizer) | 0.05% |
| Sodium sulfite (antioxidant) | 0.1% |
| Erythorbic acid (antioxidant) | 0.4% |
| Ethoxydiglycol (tradename Transcutol CG, solvent) | 5-10% |
| Paraphenylenediamine (PPD, primary intermediate) | 0.21% |
| 4-Aminophenol (PAP, primary intermediate) | 0.37% |
| Resorcinol (coupler) | 0.08% |
| 2-Methylresorcinol (coupler) | 0.39% |
| 1-Naphthol (coupler) | 0.02% |
| 4-Amino-2-hydroxytoluene (AHT, coupler) | 0.06% |
| Oleth-5 (tradename Brij ™ O5-LQ-(MH), surfactant) | 10-15% |
| Oleic acid (surfactant/buffer) | 20% |
| Ammonia (base) | 1.68-3.36% |
| Compound AK (Dye) | 0.1-3% |

Example 3

Colorimetry Evaluation of Exemplary Dyes of the Invention

Materials: Virgin light blond, virgin light brown, virgin medium brown, and single bleached medium brown hair were purchased from International Hair Importers (Glendale, N.Y.). BW 2000 Ultra Concentrated bleaching powder, 20V Hydrogen Peroxide Pure White, and 40V Hydrogen Peroxide Pure White were purchased from Clairol Professional (Stamford, Conn.). Shampoo was a solution of 7.5% (w/w) sodium lauryl sulfate (SLS, Spectrum Chemical, Gardena, Calif.) in deionized water.

Bleaching: An amount of 1 gram of virgin hair tresses from International Hair Importers was used, which had enough thickness that when laid flat on a surface the background was not seen. The bleach paste was freshly made prior to use by mixing 5.57 gram per tress of the BW 2000 Ultra Concentrated bleaching powder with 10 mL per tress of Pure White 20 V hydrogen peroxide solution. The thick, lumpy white paste was spread quickly over both sides of the hair tresses, and then, the timer was started. The paste was then spread uniformly with the fingers (gloves) into the tress so that the latter was well saturated. The tress was wrapped in aluminum foil and left to stand for a total of 30 minutes at room temperature after which the tress was thoroughly rinsed with water. It was shampooed with a 7.5% SLS solution, rinsed and dried. For quick drying, the tresses were left in the humidity chamber at 20% Relative Humidity, 50° C. for 20 minutes. Blow drying was avoided so as not to entangle the hair and induce damage. The hair was also sometimes air-dried for at least 3-4 hours. The procedure was repeated up to 3 times if triple bleached hair was desired.

Color treatment: The dye bath/paste should be enough to overwhelm the hair and saturate the hair (about 5 gram paste for 1 gram hair). When several tresses were dyed at the same time, there were delay times between the application of the dyes or shampoos that may cause the tones and shades of the dyes to be different for each tress. To minimize any discrepancy in color, the dye mix was quickly spread over both sides of the tress, and the timer started. The dye was then worked through each tress and sealed in foil as quickly as possible. After the color was developed (usually for 30 minutes), the tress was thoroughly rinsed. Tresses that had dye worked through them first were rinsed first to minimize timing differences.

Color lastingness: The lastingness of the color was determined through shampooing. Multiple shampoos may be done in a row without drying in between. The wash-out experiments were done in a consistent manner. The shampoo cycles involved the hair being lathered in a controlled manner with a 7.5% (w/w) SLS solution for 15 seconds and rinsed for 15 seconds under warm water at 35(±5)° C. This process was done 15-25 times to simulate the number of shampoos during 4-6 weeks after a consumer has dyed his/her hair.

Performance Evaluation: One gram single bleached hair tresses from International Hair Importers were (a) dyed with a leading commercial red dye or (b) treated with a non-red based commercially available kit for 30 minutes at room temperature to "lift" the hair (e.g., make the hair more porous), followed by soaking in a 0.6% (w/w) solution of compound A in a 1:1 mixture of EtOH:phosphate buffer, pH 4.5 for 10 minutes at room temperature.

Upon conclusion of the color treatment process, the tresses were rinsed until water runs clear and shampooed and rinsed once. The tresses were then shampooed, as described above. The results, shown in FIG. 1, demonstrate that tresses dyed with compound A (FIG. 1*b*) significantly resist fading, have a greater color fastness and are brighter than the tresses dyed with the leading commercial red dye (FIG. 1*a*) after the same number of washings.

Figure 2:
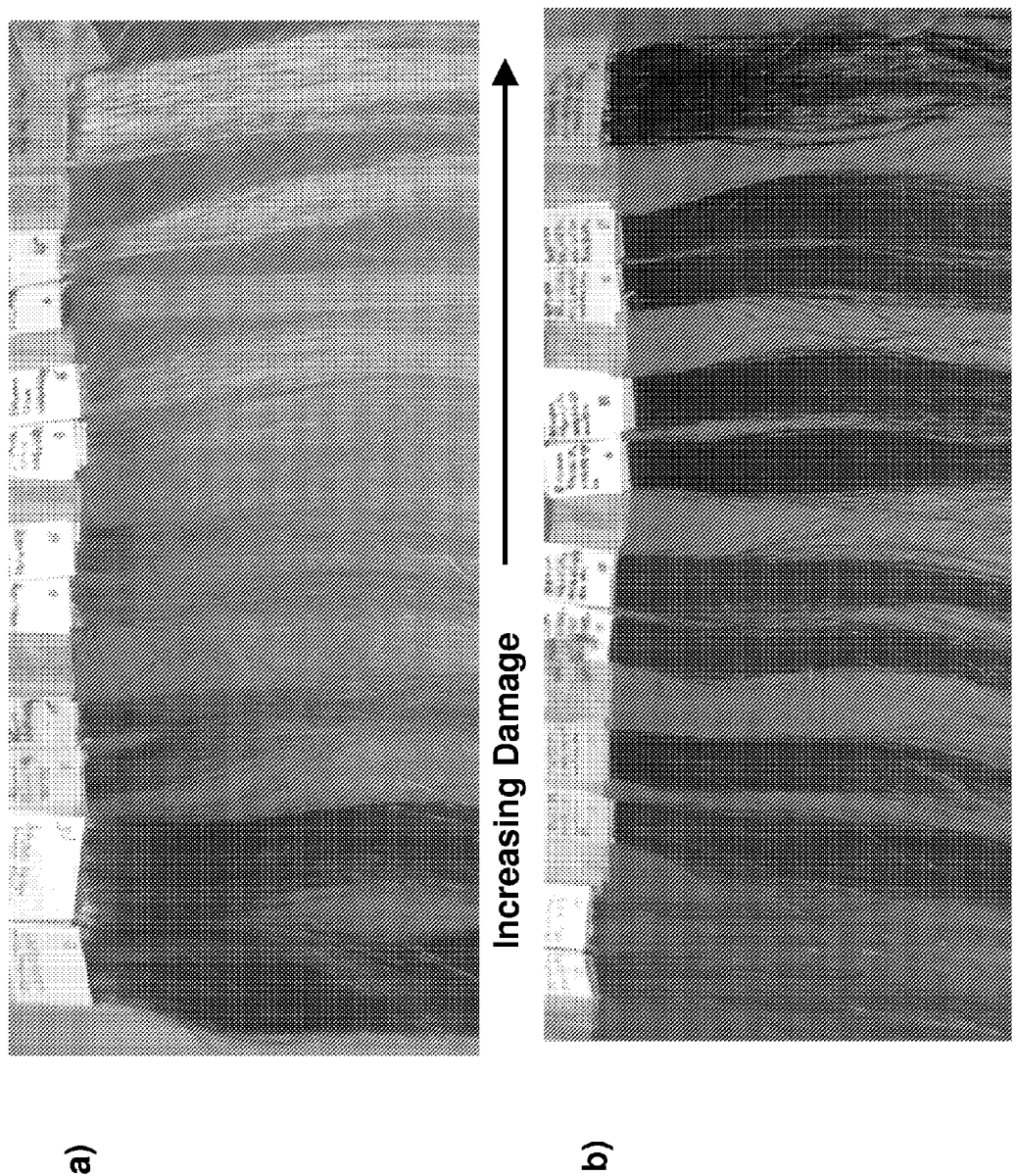
FIGS. 2a and 2b compare the color fastness of a commercially available red dye applied to increasingly damaged hair (FIG. 2a) with the color fastness of compound A applied to tresses having the same damage (FIG. 2b) immediately after application to hair and after 15 shampoo cycles. The left tress of each pair is the initial color while the right tress of each pair is the result after shampooing. The last tress in both 2a and b does not have a shampooing pair (only the initial color was examined).

In a second assay to determine the effect of the dyes of the invention on damaged hair, virgin medium blond, single bleached (commercial), 3×40 V from virgin medium brown, platinum (commercial double bleached), 6×40 V from Virgin medium brown, and 9×40 V from virgin medium brown were (a) dyed with either the leading commercially available red dye (1 g of dye cream to 1 mL of 20V peroxide) for 30 minutes at room temperature or (b) treated with a blond commercially available kit such as L'Oréal Superior Preference 9½ NB or with a dyeless base prepared on site for 30 minutes at room temperature to "lift" the hair (e.g., make the hair more porous), followed by soaking in a 0.6% (w/w) solution of compound A in a 1:1 mixture of EtOH:phosphate buffer, pH 4.5 for 10 minutes at room temperature. The results, shown in FIG. 2, demonstrate that with increasing damage (moving from left to right across FIG. 2), the leading commercial red dye exhibits significant fading and color loss (FIG. 2*a*). In contrast, the tresses dyed with compound A demonstrated an inverse color fastness to porosity property. That is, with increased damage to hair, compound A provided greater deposits of color and a greater color fastness compared to the leading commercially available red dye on similarly damaged hair.

Example 4

Visual Inspection of Exemplary Dyes of the Invention

To determine the extent of color fastness and vibrancy, a number of tresses are prepared as described above in Example 3. After the tresses are dried, a visual inspection comparing the tresses with control tresses is performed to evaluate vibrancy and color fastness of the dyes. A scale from 1 to 4 is then used to rank the vibrancy and color fastness compared to the control tresses, as shown below. Additionally, compounds of the present invention were analyzed for color fastness on hair tresses using a Konica Minolta Chroma Meter CR-400 with the SpectraMagic™ NX Lite CM-S100w 1.91.0002 software package and were found to retain color after multiple shampoo cycles.

| Vibrancy Scale |
| --- |
| 1 = no vibrancy when compared to control |
| 2 = little vibrancy when compared to control |
| 3 = some vibrancy when compared to control |
| 4 = substantially the same vibrancy when compared to control |
| 5 = greater vibrancy when compared to control |

| Color Fastness Scale |
| --- |
| 1 = no no color when compared to control |
| 2 = little color when compared to control |
| 3 = some color when compared to control |
| 4 = substantially the same color when compared to control |
| 5 = greater color when compared to control |

Equivalents

Those skilled in the art will recognize, or be able to ascertain using no more than routine experimentation, many equivalents to the specific embodiments of the invention described herein. Such equivalents are intended to be encompassed by the following claims.

Incorporation by Reference

The contents of all references, patents and patent applications cited throughout this application are hereby incorporated by reference.

The invention claimed is:

1. A functionalized dye comprising at least one chromophore and a color fastness moiety, wherein the chromophore is bound to the color fastness moiety by a linker, wherein said dye is a compound of formula Ia:

C-L-F   (Ia), wherein

C is a chromophore of formula IIg:

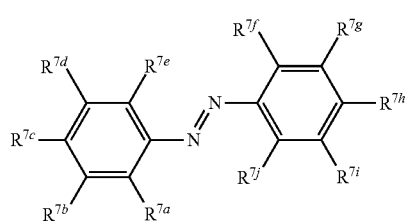

(IIg)

or

C is a chromophore represented by the following structural formula:

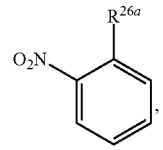

wherein $R^{7c}$ is attached to linker L;

$R^{7a}$, $R^{7b}$, $R^{7d}$, $R^{7e}$, $R^{7f}$, $R^{7g}$, $R^{7h}$, $R^{7i}$ and $R^{7j}$ are each independently hydrogen, hydroxyl, alkyl, alkenyl, alkynyl, aryl, amino, alkylammonium, sulfonyl, carbonyl, carboxy, alkoxy, aryloxy, halogen, acyl, oximyl, hydrazinyl, —$NO_2$, —CN, a heterocyclic moiety or thioether;

$R^{26a}$ is attached to linker L;

L is a linker of formula (III):

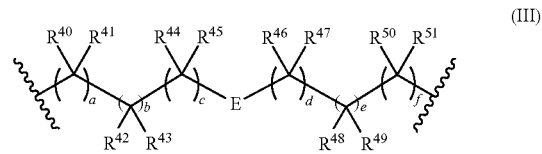

(III)

wherein

L covalently links the chromophore C via the left hand side of formula III to the color fastness moiety F via the right hand side of formula III;

a, b, c, d, e, and f are each independently an integer from 0-2, provided that at least one of a, b, c, d, e and f is not 0;

$R^{40}$, $R^{41}$, $R^{42}$, $R^{43}$, $R^{44}$, $R^{45}$, $R^{46}$, $R^{47}$, $R^{48}$, $R^{49}$, $R^{50}$ and $R^{51}$ are each independently absent or hydrogen;

E is $NR^{52}$ or $NR^{53}C$=O;

$R^{52}$ and $R^{53}$ are each independently hydrogen or alkyl;

the color fastness moiety is of formula (Va):

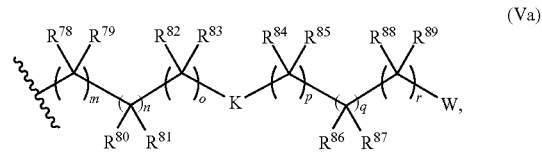

(Va)

wherein m, n, o, p, q and r are each independently an integer from 0-2, provided that at least one of m, n, o, p, q and r is not 0;

$R^{78}$, $R^{79}$, $R^{80}$, $R^{81}$, $R^{82}$, $R^{83}$, $R^{84}$, $R^{85}$, $R^{87}$, $R^{88}$ and $R^{89}$ are each independently hydrogen or absent;

$R^{86}$ is absent, hydrogen or hydroxyl;

K is $NR^{90}$, C(=O)$NR^{92}$ or OC=O;

W is $NR^{95}R^{96}$, $CR^{97}R^{98}R^{99}$ or $OR^{100}$;

$R^{90}$ and $R^{92}$ are each independently hydrogen or alkyl;

$R^{95}$ is alkyl and $R^{96}$ is hydrogen or alkyl, or $R^{95}$ and $R^{96}$, together with the nitrogen to which they are attached are linked to form a 4-8-membered heterocyclic ring comprising 1-3 heteroatoms;

$R^{97}$, $R^{98}$ and $R^{99}$ are hydrogen, alkyl, alkoxy or heteroaryl; and $R^{100}$ is hydrogen or alkyl, and or a cosmetically acceptable salt thereof.

2. The dye of claim 1, wherein a, b, c and d are each 0, e and f are each 1, E is $NR^{52}$ and $R^{52}$ is hydrogen.

3. The dye of claim 1 wherein m, n and o are 0, p, q and r are each 1, $R^{84}$, $R^{85}$, $R^{86}$, $R^{87}$; $R^{88}$ and $R^{89}$ are each hydrogen, K is $NR^{90}$ and $R^{90}$ is hydrogen.

4. The dye of claim 1 wherein m, n, o and p are 0, q and r are each 1, $R^{86}$, $R^{87}$; $R^{88}$ and $R^{89}$ are each hydrogen, K is $NR^{90}$ and $R^{90}$ is hydrogen.

5. The dye of claim 1, wherein the dye is a compound of represented by the following structural formula:

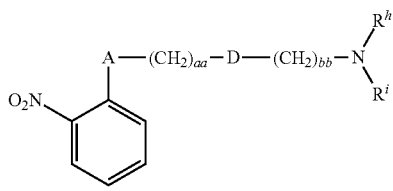

wherein
aa and bb are each an integer from 1-5;
A is $NR^f$ or $NR^fCO$;
D is O(CO), $NR^g$ or $CONR^g$;
$R^f$, $R^g$ and $R^h$ are each independently hydrogen or alkyl;
$R^i$ is alkyl; or $R^h$ and $R^i$ are linked together with the atom to which they are attached form a 4-8 membered heterocyclic ring with 1-3 heteroatoms; or a cosmetically acceptable salt thereof.

6. The dye of claim 5, wherein A is $NR^f$, D is $NR^g$ and $R^f$ and $R^g$ are each hydrogen.

7. The dye of claim 6, wherein $R^h$ and $R^i$ are each alkyl.

8. The dye of claim 7, wherein said alkyl is methyl, ethyl or hydroxyethyl.

9. The dye of claim 6, wherein $R^h$ and $R^i$ are linked to form a 6-membered heterocyclic ring.

10. The dye of claim 9, wherein said ring is a piperidine or morpholine ring.

11. The dye of claim 5, wherein the dye is a compound represented by the following structural formula:

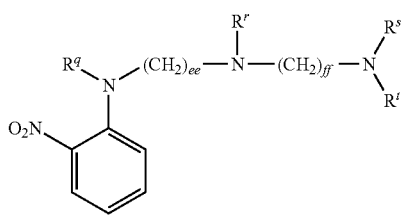

wherein
$R^q$ and $R^r$ are each independently hydrogen or alkyl;
ee and ff are each independently an integer from 1-5; and
$R^s$ and $R^t$ are each alkyl or together with the atom to which they are attached form a 4-8 membered heterocyclic ring with 1 or 2 heteroatoms, and cosmetically acceptable salts thereof.

12. The dye of claim 11, wherein $R^q$ and $R^r$ are each hydrogen, and ee is 2 and ff is 3.

13. The dye of claim 12, wherein $R^s$ and $R^t$ are each alkyl.

14. The dye of claim 13, wherein said alkyl is methyl, ethyl or hydroxyethyl.

15. The dye of claim 11, wherein $R^S$ and $R^t$ are linked to form a 6-membered heterocyclic ring.

16. The dye of claim 15, wherein said ring is a piperidine or morpholine ring.

17. The dye of claim 11, wherein the dye is a compound represented by the following structural formula:

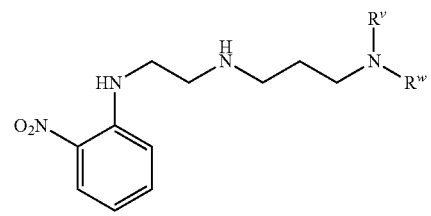

wherein $R^v$ and $R^w$ are alkyl, and cosmetically acceptable salts thereof.

18. The dye of claim 17, wherein $R^v$ and $R^w$ are each methyl, ethyl or hydroxyethyl.

19. The dye of claim 1, wherein
C is a chromophore of formula IIg:

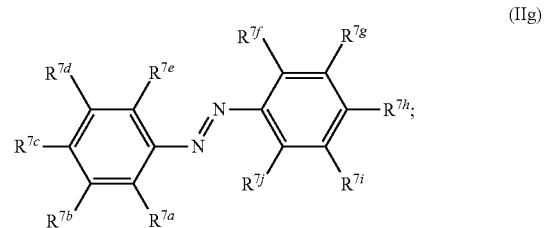

L is a linker formula (III):

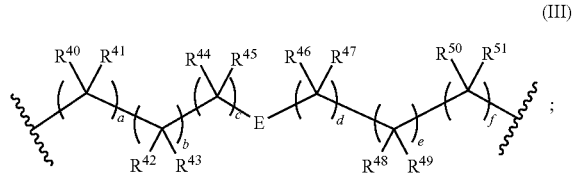

and
F is a color fastness moiety is of formula (Va)

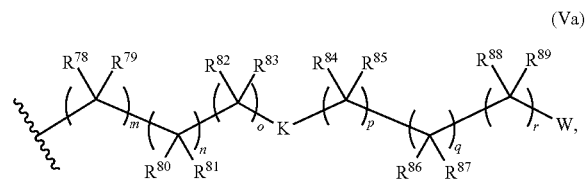

wherein
$R^{7a}$, $R^{7b}$, $R^{7d}$, $R^{7e}$, $R^{7f}$, $R^{7g}$ and $R^{7i}$ are each hydrogen;
$R^{7h}$ is $-NO_2$;
$R^{7j}$ is halogen;
$R^{7c}$ is attached to L;
a, b, c, d and e are each 0;
E is $NR^{52}$;
$R^{52}$ is alkyl;
f is 1;
$R^{50}$ and $R^{51}$ are each hydrogen;

m, n and, o are each 0;
K is C(=O)NR$^{92}$;
p, q and r are each 1;
R$^{84}$, R$^{85}$, R$^{87}$, R$^{88}$, R$^{89}$ and R$^{92}$ are each hydrogen;
R$^{86}$ is hydrogen or hydroxyl;
W is NR$^{95}$R$^{96}$, CR$^{97}$R$^{98}$R$^{99}$, or OR$^{100}$
R$^{95}$ and R$^{96}$ are each alkyl or linked to form a ring;
R$^{97}$ is hydrogen;
R$^{98}$ is hydrogen or alkoxy;
R$^{99}$ is alkoxy or hydroxyl; and
R$^{100}$ is hydrogen;
or a cosmetically acceptable salt thereof.

20. The dye of claim 19, wherein R$^{84}$, R$^{85}$, R$^{86}$, R$^{87}$, R$^{88}$, R$^{89}$ and R$^{92}$ are each hydrogen; W is NR$^{95}$R$^{96}$; and R$^{95}$ and R$^{96}$ are each alkyl.

21. The dye of claim 19, wherein R$^{84}$, R$^{85}$, R$^{86}$, R$^{87}$, R$^{88}$, R$^{89}$ and R$^{92}$ are each hydrogen; W is NR$^{95}$R$^{96}$; and R$^{95}$ and R$^{96}$ are linked to form a ring.

22. The dye of claim 19, wherein R$^{84}$, R$^{85}$, R$^{86}$, R$^{87}$, R$^{88}$, R$^{89}$ and R$^{92}$ are each hydrogen; W is CR$^{97}$R$^{98}$R$^{99}$; R$^{97}$ is hydrogen; and R$^{98}$ and R$^{99}$ are each alkoxy.

23. The dye of claim 19, wherein R$^{84}$, R$^{85}$, R$^{86}$, R$^{87}$, R$^{88}$, R$^{89}$ and R$^{92}$ are each hydrogen; W is CR$^{97}$R$^{98}$R$^{99}$; R$^{97}$ and R$^{98}$ are each hydrogen; and R$^{99}$ is hydroxyl.

24. The dye of claim 19, wherein R$^{84}$, R$^{85}$, R$^{87}$, R$^{88}$, R$^{89}$ and R$^{92}$ are each hydrogen; R$^{86}$ is hydroxyl; W is OR$^{100}$; and R$^{100}$ is hydrogen.

25. A dye selected from:

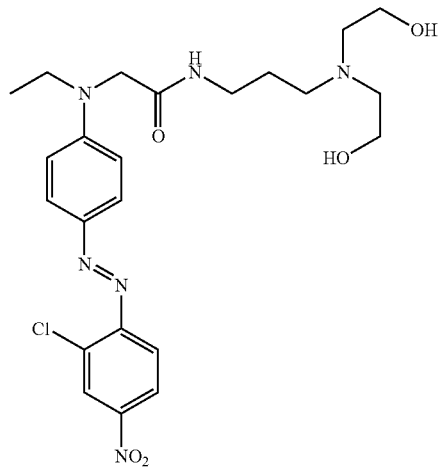

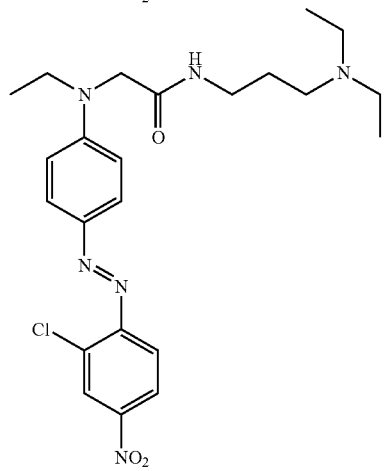

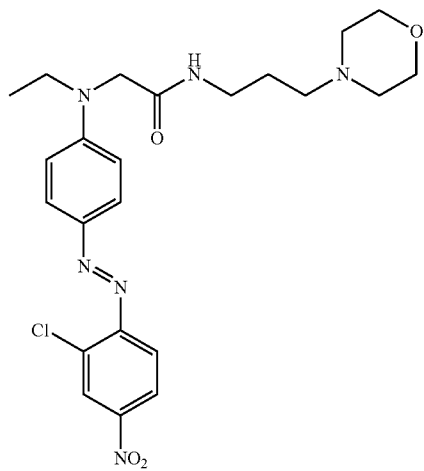

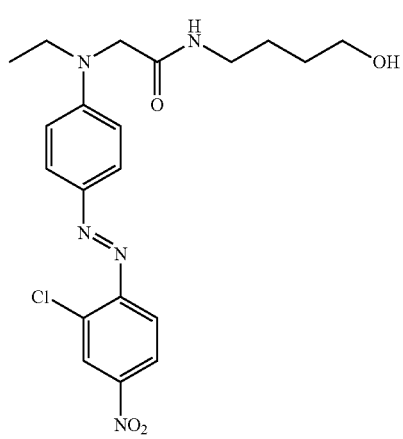

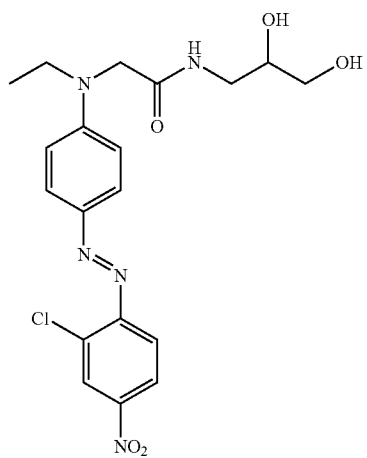

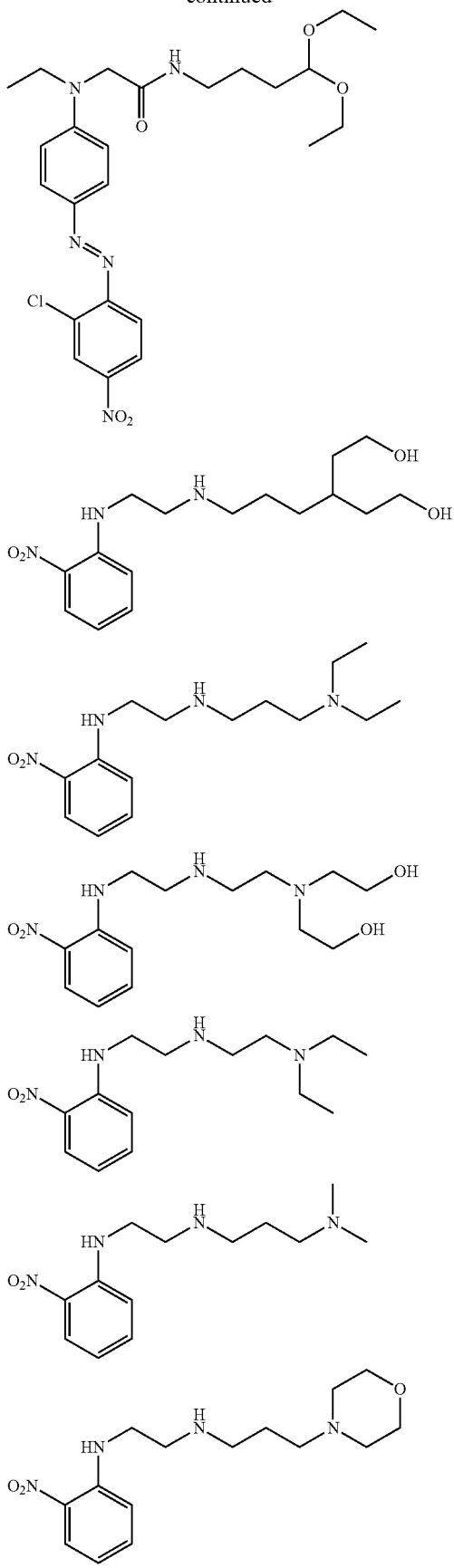
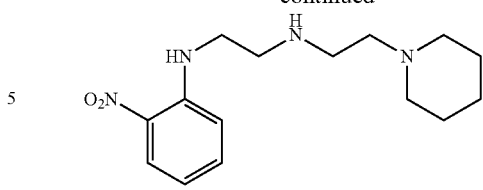
and cosmetically acceptable salts thereof.
26. A dye represented by the following structural formula:
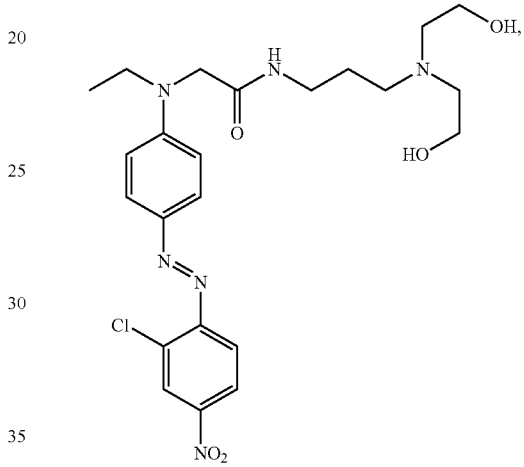
or a cosmetically acceptable salt thereof.
27. A dye represented by the following structural formula:
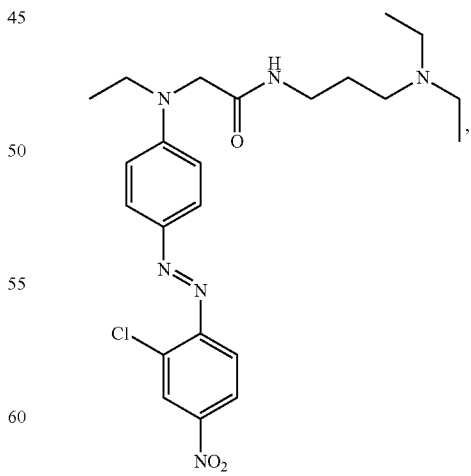
or a cosmetically acceptable salt thereof.

28. A dye represented by the following structural formula:

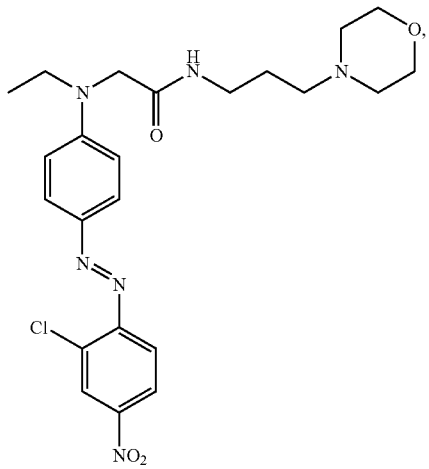

or a cosmetically acceptable salt thereof.

29. A dye represented by the following structural formula:

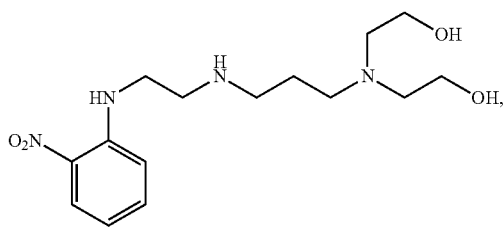

or a cosmetically acceptable salt thereof.

30. A dye represented by the following structural formula:

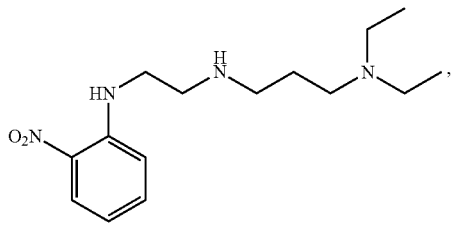

or a cosmetically acceptable salt thereof.

31. The dye of claim 1, wherein the dye is a non-oxidative dye.

32. The dye of claim 1, wherein the functionalized dye has greater color fastness compared to a non-functionalized direct dye.

33. A dye composition comprising at least one dye of claim 1 and a medium suitable for dyeing keratin fibers.

34. The composition of claim 33, wherein said medium further includes one or more of surfactants, thickeners, fragrances, sequestering agents, UV-screening agents, waxes, silicones, preserving agents, couplers, primary intermediates, alkalizing agents, direct dyes, ceramides, oils, vitamins, provitamins, opacifiers, reducing agents, antioxidants, emulsifiers, stabilizers, solvents, and buffers.

35. A method for coloring hair comprising applying to said hair a dye composition comprising at least one dye of claim 1, such that said hair is colored.

36. The method of claim 35, wherein said coloring hair is highlighting hair or touching up roots.

37. A kit comprising a dye composition comprising at least one dye of claim 1 and instructions for use.

38. A method for coloring hair comprising the steps of
   a) treating the hair with an oxidative dye in the presence of ammonia and optionally hydrogen peroxide for between about 1 and about 60 minutes;
   b) optionally rinsing the hair; and optionally partially drying the hair;
   c) treating the hair with a dye composition comprising at least one dye of claim 1 for between about 1 and about 60 minutes; and
   d) rinsing the hair.

39. The method of claim 38 further comprising one or more of the following steps:
   e) washing the hair with shampoo; and/or conditioning the hair with conditioner after rinsing the hair;
   f) rinsing the hair; and
   g) optionally drying the hair.

* * * * *

UNITED STATES PATENT AND TRADEMARK OFFICE
CERTIFICATE OF CORRECTION

PATENT NO.       : 8,187,340 B2                                         Page 1 of 1
APPLICATION NO.  : 12/975007
DATED            : May 29, 2012
INVENTOR(S)      : Lewis et al.

It is certified that error appears in the above-identified patent and that said Letters Patent is hereby corrected as shown below:

| | |
|---|---|
| Column 138, Line 42 | replace the phrase "the color fastness moiety is of formula (Va):" with "F is a color fastness moiety of formula (Va):" |
| Column 138, Line 66 | delete the word "and" |
| Column 139, Line 7 | replace "$R^{88}$" with "$R^{88}$" |
| Column 139, Lines 59-60 | replace the phrase "and cosmetically acceptable salts thereof." with "or a cosmetically acceptable salt thereof." |
| Column 140, Lines 16-17 | replace the phrase "and cosmetically acceptable salts thereof." with "or a cosmetically acceptable salt thereof." |
| Column 140, Line 35 | insert --of-- between the words "linker" and "formula (III)" |
| Column 140, Line 47 | delete "is" between the words "moiety" and "of formula (Va)" |

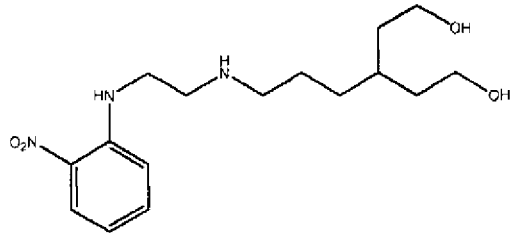

Column 143, Lines 20-25      replace the structure

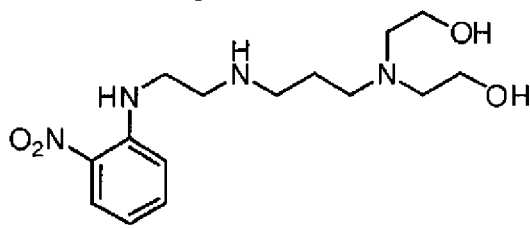

with the structure

| | |
|---|---|
| Column 144, Line 13 | replace the phrase "and cosmetically acceptable salts thereof." with "or a cosmetically acceptable salt thereof." |

Signed and Sealed this
Fourth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,187,340 B2
APPLICATION NO. : 12/975007
DATED : May 29, 2012
INVENTOR(S) : Lewis et al.

It is certified that error appears in the above-identified patent and that said Letters Patent is hereby corrected as shown below:

In the Claims

Claim 21, Column 141, Line 10     delete "or hydroxyl"
Claim 21, Column 141, Line 25     delete "; and $R^{99}$ is hydroxyl"

Signed and Sealed this
Twenty-ninth Day of October, 2013

Teresa Stanek Rea
*Deputy Director of the United States Patent and Trademark Office*